United States Patent [19]
Greenlee et al.

[11] Patent Number: 5,183,810
[45] Date of Patent: Feb. 2, 1993

[54] IMIDAZOLE ANGIOTENSIN II ANTAGONISTS INCORPORATING A SUBSTITUTED BENZYL ELEMENT

[75] Inventors: William J. Greenlee, Teaneck; Arthur A. Patchett, Westfield, both of N.J.; David Hangauer, East Amherst, N.Y.; Thomas F. Walsh, Westfield, N.J.; Kenneth J. Fitch, Cranford, N.J.; Ralph A. Rivero, Eatontown, N.J.; Daljit S. Dhanoa, Tinton Falls, N.J.

[73] Assignee: Merck & Co., Inc., Rahway, N.J.

[21] Appl. No.: 744,565

[22] Filed: Aug. 13, 1991

Related U.S. Application Data

[63] Continuation of Ser. No. 671,593, Mar. 19, 1991, abandoned, which is a continuation of Ser. No. 479,780, Feb. 13, 1990, abandoned.

[51] Int. Cl.$^5$ .............. A61K 31/415; C07D 403/04; C07D 403/06; C07D 403/10
[52] U.S. Cl. ...................... 514/63; 514/381; 514/383; 514/384; 514/397; 514/398; 514/399; 514/400; 548/323.1; 548/340.1; 548/341.5; 548/343.1; 548/252; 548/253; 548/254; 548/251; 548/110; 548/312.7; 548/311.1; 548/313.1; 548/311.4; 548/337.1; 548/335.5; 548/322.5; 548/343.5; 548/321.5
[58] Field of Search ............ 548/336, 339, 340, 341, 548/342, 343, 252, 253, 254, 110, 251; 514/63, 381, 383, 384, 397, 398, 399, 400

[56] References Cited

U.S. PATENT DOCUMENTS

| | | | |
|---|---|---|---|
| 4,481,211 | 11/1982 | Dockner et al. | 548/340 |
| 4,582,847 | 3/1983 | Furukawa et al. | 548/340 |
| 4,859,779 | 1/1989 | Finkelstein et al. | 548/340 |
| 4,880,804 | 11/1989 | Carini et al. | 514/234.5 |
| 4,882,348 | 12/1987 | Kruse et al. | 548/340 |
| 4,935,438 | 12/1987 | Kruse et al. | 548/340 |
| 4,992,459 | 3/1988 | Finkelstein et al. | 548/340 |

FOREIGN PATENT DOCUMENTS

| | | |
|---|---|---|
| 0324377 | 7/1989 | European Pat. Off. |
| 429257 | 5/1991 | European Pat. Off. |
| 430709 | 6/1991 | European Pat. Off. |
| 434249 | 6/1992 | European Pat. Off. |
| WO91/11909 | 8/1991 | PCT Int'l Appl. |
| WO91/11999 | 8/1991 | PCT Int'l Appl. |
| WO91/12001 | 8/1991 | PCT Int'l Appl. |
| WO91/12002 | 8/1991 | PCT Int'l Appl. |

*Primary Examiner*—Johann Richter
*Attorney, Agent, or Firm*—Valerie J. Camara; Joseph F. DiPrima; William H. Nicholson

[57] ABSTRACT

Substituted imidazoles attached through a methylene bridge to novel substituted phenyl derivatives of the Formula I, are useful as angiotensin II antagonists.

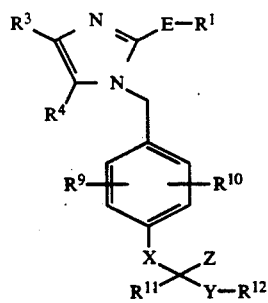

FORMULA I

8 Claims, No Drawings

IMIDAZOLE ANGIOTENSIN II ANTAGONISTS INCORPORATING A SUBSTITUTED BENZYL ELEMENT

The present invention is a continuation in part of copending application Ser. No. 671,593 filed on Mar. 19, 1991 now abandoned, which is a continuation in part application of copending Ser. No. 479,780 filed Feb. 13, 1990 (now abandoned).

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally phenyl bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed within this application have been claimed or disclosed in any U.S. Patent, European Applications or articles.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of Formula I:

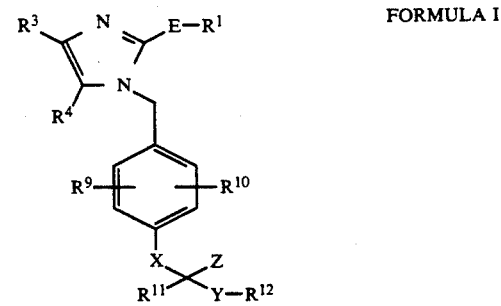

FORMULA I or a pharmaceutically acceptable salt thereof wherein:
$R^1$ is:
- (a) $(C_1-C_6)$-alkyl, $(C_2-C_6)$-alkenyl or $(C_2-C_6)$-alkynyl each of which is unsubstituted or substituted with a substituent selected from the group consisting of:
  - i) aryl as defined below,
  - ii) $(C_3-C_7)$-cycloalkyl,
  - iii) Cl, Br, I, F,
  - iv) $COOR^2$,
  - vii) $N[((C_1-C_4)\text{-alkyl})]_2$,
  - viii) $NHSO_2R^2$,
  - ix) $CF_3$,
  - x) $COOR^2$, or
  - xi) $SO_2NHR^{2a}$; and
- (b) aryl, wherein aryl is defined as phenyl or naphthyl, unsubstituted or substituted with 1 or 2 substituents selected from the group consisting of:
  - i) Cl, Br, F, I,
  - ii) $(C_1-C_4)$-alkyl,
  - iii) $(C_1-C_4)$-alkoxy,
  - iv) $NO_2$
  - v) $CF_3$
  - vi) $SO_2NR^{2a}R^{2a}$,
  - vii) $(C_1-C_4)$-alkylthio,
  - viii) hydroxy,
  - ix) amino,
  - x) $(C_3-C_7)$-cycloalkyl,
  - xi) $(C_3-C_{10})$-alkenyl; and
- (c) heteroaryl, wherein heteroaryl is defined as an unsubstituted, monosubstituted or disubstituted heteroaromatic 5- or 6-membered cyclic moiety, which can contain one or two members selected from the group consisting of N, O, S and wherein the substituents are members selected from the group consisting of:
  - i) Cl, Br, F, I,
  - ii) OH,
  - iii) SH,
  - iv) $NO_2$,
  - v) $(C_1-C_4)$-alkyl,
  - vi) $(C_2-C_4)$-alkenyl,
  - vii) $(C_2-C_4)$-alkynyl,
  - viii) $(C_1-C_4)$-alkoxy, or
  - ix) $CF_3$, or
- (d) $(C_1-C_4)$-perfluoroalkyl; and E is:
- (a) a single bond, (b) —S(O)$_x$(CH$_2$)$_s$—, or
(c) —O—; and
x is 0 to 2,
s is 0 to 5;
m is 1 to 5;
p is 0 to 3;
n is 1 to 10;
R$^2$ is:
  (a) H, or
  (b) (C$_1$–C$_6$)-alkyl, and
R$^{2a}$ is:
  (a) R$^2$,
  (b) CH$_2$-aryl, or
  (c) aryl; and
R$^3$ is:
  (a) H,
  (b) (C$_1$–C$_6$)-alkyl, (C$_2$–C$_6$)-alkenyl or (C$_2$–C$_6$)-alkynyl,
  (c) Cl, Br, I, F,
  (d) NO$_2$,
  (e) (C$_1$–C$_8$)-perfluoroalkyl,
  (f) C$_6$F$_5$,
  (g) CN,
  (h) NH$_2$,
  (i) NH[(C$_1$–C$_4$)-alkyl],
  (j) N[(C$_1$–C$_4$)-alkyl]$_2$,
  (k) NH[CO(C$_1$–C$_4$)-alkyl],
  (l) N[(C$_1$–C$_4$)-alkyl)-(CO(C$_1$–C$_4$)-alkyl)],
  (m) N(C$_1$–C$_4$)-alkyl-COaryl,
  (n) N(C$_1$–C$_4$)alkyl-SO$_2$aryl,
  (o) CO$_2$H,
  (p) CO$_2$R$^{2a}$,
  (q) phenyl,
  (r) phenyl-(C$_1$–C$_3$)-alkyl,
  (s) phenyl and phenyl-(C$_1$–C$_3$)-alkyl substituted on the phenyl ring with one or two substituents selected from:
    i) (C$_1$–C$_4$)-alkyl,
    ii) (C$_1$–C$_4$)-alkoxyl,
    iii) F, Cl, Br, I,
    iv) hydroxyl,
    v) methoxyl,
    vi) CF$_3$,
    vii) CO$_2$R$^{2a}$, or
    viii) NO$_2$; and
R$^4$ is:
  (a) H,
  (b) CN,
  (c) (C$_1$–C$_8$)-alkyl,
  (d) (C$_3$–C$_6$)-alkenyl,
  (e) (C$_1$–C$_8$)-perfluoroalkyl,
  (f) (C$_1$–C$_8$)-perfluoroalkenyl,
  (g) NH$_2$,
  (h) NH(C$_1$–C$_4$)-alkyl,
  (i) N[(C$_1$–C$_4$)-alkyl]$_2$,
  (j) NH(C$_1$–C$_4$)-acyl,
  (k) N[((C$_1$–C$_4$)-acyl)((C$_1$–C$_4$)-alkyl)],
  (l) CO$_2$H,
  (m) CO$_2$R$^{24}$,
  (n) phenyl,
  (o) phenyl-(C$_2$–C$_6$)-alkenyl, (p) $\overset{O}{\overset{\|}{C}}$—R$^{16}$, (q) (CH$_2$)$_{n-1}$$\overset{OR^{17}}{\overset{|}{CH}}$—R$^{17}$, (r) (CH$_2$)$_n$O$\overset{O}{\overset{\|}{C}}$R$^{14}$, (s) (CH$_2$)$_n$SR$^{15}$, (t) CH=CH(CH$_2$)$_2$O$\overset{O}{\overset{\|}{C}}$R$^{15}$, (u) CH=CH(CH$_2$)$_s$$\overset{O}{\overset{\|}{C}}$R$^{17}$, (v) (CH$_2$)$_s$—$\overset{CH_3}{\overset{|}{CH}}$—$\overset{}{\underset{O}{\overset{\|}{C}}}$R$^{15}$ (w) (CH$_2$)$_n$$\overset{O}{\overset{\|}{C}}$R$^{15}$, (x) (CH$_2$)$_n$O$\overset{O}{\overset{\|}{C}}$NHR$^{16}$, (y) (CH$_2$)$_n$O$\overset{S}{\overset{\|}{C}}$NHR$^{16}$, (z) (CH$_2$)$_n$NHSO$_2$R$^{16}$,
  (aa) (CH$_2$)$_n$F,
  (ab) (CH$_2$)$_m$-imidazol-1-yl,
  (ac) (CH$_2$)$_m$-1,2,3-triazolyl, unsubstituted or substituted with one or two substituents selected from:
    i) CO$_2$CH$_3$,
    ii) (C$_1$–C$_4$)-alkyl,
  (ad) tetrazol-5-yl,
  (ae) —CONHSO$_2$-aryl,
  (af) —CONHSO$_2$—(C$_1$–C$_8$)-alkyl, wherein the alkyl group is unsubstituted or substituted with a substituent selected from the group consisting of: —OH, —SH, —O(C$_1$–C$_4$)-alkyl, —S—(C$_1$–C$_4$)-alkyl, —CF$_3$, Cl, Br, F, I, —NO$_2$, —CO$_2$H, —CO$_2$—(C$_1$–C$_4$)-alkyl, —NH$_2$, —NH[(C$_1$–C$_4$)-alkyl], —N[(C$_1$–C$_4$)-alkyl]$_2$; and
  (ag) —CONHSO$_2$—(C$_1$–C$_4$)-perfluoroalkyl,
  (ah) —CONHSO$_2$NR$^{2a}$R$^{2a}$; and (ag) —(CH$_2$)$_s$— [triazole ring with N=N, NH, R$^5$ substituent], (ah) —(CH$_2$)$_s$— [ring with N, N, NH, CF$_3$], or (ai) —CH=N—NH— [imidazole ring with N, NH]; and R$^5$ is:
  (a) CN,
  (b) NO$_2$, or (c) $CO_2R^{2a}$; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form an phenyl ring,
(h) $(C_1-C_6)$-perfluoroalkyl,
(i) $(C_3-C_7)$-cycloalkyl, unsubstituted or substituted with $(C_1-C_6)$-alkyl,
(j) aryl,
(k) $(C_1-C_6)$-alkyl-$S(O)_x$—$(CH_2)_n$—,
(l) hydroxy-$(C_1-C_6)$-alkyl,
(m) —$CF_3$,
(n) —$CO_2R^{2a}$,
(o) —OH,
(p) —$NR^2R^{21}$,
(q) —$[(C_1-C_6)$-alkyl$]NR^2R^{21}$,
(r) —$NO_2$,
(s) —$(CH_2)_n$—$SO_2$—$N(R^2)_2$,
(t) —$NR^2CO$—$(C_1-C_4)$-alkyl, or
(u) —$CON(R^2)_2$; and X is:
(a) —O—,
(b) —$S(O)_x$—,
(c) —$NR^{13}$—
(d) —$CH_2O$—,
(e) —$CH_2S(O)_x$,
(f) —$CH_2NR^{13}$—,
(g) —$OCH_2$—,
(h) —$NR^{13}CH_2$—,
(i) —$S(O)_xCH_2$—,
(j) —$CH_2$—,
(k) —$(CH_2)_2$—,
(l) single bond, or
(m) —CH=, wherein Y and $R^{12}$ are absent forming a —C=C— bridge to the carbon bearing Z and $R^{11}$; and Y is:
(a) single bond,
(b) —O—,
(c) —$S(O)_x$—,
(d) —$NR^{13}$—, or
(e) —$CH_2$—; and
except that X and Y are not defined in such a way that the carbon atom to which Z is attached also simultaneously is bonded to two heteroatoms (O, N, S, SO, $SO_2$);

$R^{11}$ and $R^{12}$ are independently:
(a) H,
(b) $(C_1-C_6)$-alkyl, unsubstituted or substituted with a substituent selected from the group consisting of:
(i) aryl,
(ii) $(C_3-C_7)$-cycloalkyl,
(iii) $NR^2R^{21}$,
(iv) morpholin-4-yl,
(v) OH,
(vi) $CO_2R^{2a}$, or
(vii) $CON(R^2)_2$,
(c) aryl or aryl-$(C_1-C_2)$-alkyl, unsubstituted or substituted with 1 to 3 substitutents selected from the group consisting of:
(i) Cl, Br, I, F,
(ii) $(C_1-C_6)$-alkyl,
(iii) $[(C_1-C_5)$-alkenyl$]CH_2$—,
(iv) $[(C_1-C_5)$-alkynyl$]CH_2$—,
(v) $(C_1-C_6)$-alkyl-$S(O)_n$—$(CH_2)_n$—,
(vi) —$CF_3$,
(vii) —$CO_2R^{2a}$,
(viii) —OH,
(ix) —$NR^2R^{21}$,
(x) —$NO_2$,
(xi) —$NR^2COR^2$,
(xii) —$CON(R^2)_2$,
(xiii) —G—$[(C_1-C_6)$-alkyl$]$—$R^{23}$,
(xiv) —$N[CH_2CH_2]_2Q$, or
(xv) —$P(O)[O$—$(C_1-C_4)$-alkyl$]_2$,
and can additionally be substituted with 1 or 2 substituents selected from the group consisting of: Br, Cl or F,
(d) $(C_3-C_7)$-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_x$ and $NR^{22}$; and G is: a single bond, O, $S(O)_x$ or $NR^{23}$; and
Q is: O, $S(O)_x$ or $NR^{22}$; and $R^{13}$ is:
(a) H,
(b) $(C_1-C_6)$-alkyl,
(c) aryl,
(d) aryl-$(C_1-C_6)$-alkyl—(C=O)—,
(e) $(C_1-C_6)$-alkyl—(C=O)—,
(f) $[(C_2-C_5)$-alkenyl$]CH_2$—,
(g) $[(C_2-C_5)$-alkynyl$]CH_2$—, or
(h) aryl-$CH_2$—; and Z is:
(a) —$CO_2H$,
(b) —$CO_2R^{24}$,
(c) —tetrazol-5-yl,
(d) —CONH(tetrazol-5-yl)
(e) —$CONHSO_2$-aryl,
(f) —$CONHSO_2$—$(C_1-C_8)$-alkyl, wherein the alkyl group is unsubstituted or substituted with a substitutent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH$[(C_1-C_4)$-alkyl$]$, —N$[(C_1-C_4)$-alkyl$]_2$; and
(g) —$CONHSO_2$—$(C_1-C_4)$-perfluoroalkyl,
(h) —$CONHSO_2$-heteroaryl, or
(i) —$CONHSO_2NR^{2a}R^{2a}$; and
(j) —$SO_2NHCO$-aryl,
(k) —$SO_2NHCO$—$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH$[(C_1-C_4)$-alkyl$]$, —N$[(C_1-C_4)$-alkyl$]_2$; and
(l) —$SO_2NHCO$—$(C_1-C_4)$-perfluoroalkyl,
(m) —$SO_2NHCO$-heteroaryl,
(n) —$SO_2NHCONR^{2a}R^{2a}$;
(o) —$PO(OH)_2$,
(p) —$PO(OR^2)_2$, or
(q) —$PO(OH)(OR^2)$; and $R^{14}$ is:
(a) H,
(b) $(C_1-C_8)$-alkyl,
(c) $(C_1-C_8)$-perfluoroalkyl,
(d) $(C_3-C_6)$-cycloalkyl, (e) phenyl, or
(f) benzyl; and $R^{15}$ is:
(a) H,
(b) $(C_1-C_6)$-alkyl,
(c) $(C_3-C_6)$-cycloalkyl,
(d) $(CH_2)_p$-phenyl,
(e) $OR^{17}$,
(f) morpholin-4-yl, or
(g) $NR^{18}R^{19}$; and $R^{16}$ is:
(a) $(C_1-C_8)$-alkyl,
(b) $(C_1-C_8)$-perfluoroalkyl,
(c) 1-adamantyl,
(d) 1-naphthyl,
(e) (1-naphthyl)ethyl, or
(f) $-(CH_2)_p$-phenyl; and $R^{17}$ is:
(a) H,
(b) $(C_1-C_6)$-alkyl,
(c) $(C_3-C_6)$-cycloalkyl,
(d) phenyl, or
(e) benzyl; and $R^{18}$ and $R^{19}$ are independently:
(a) H,
(b) $(C_1-C_4)$-alkyl,
(c) phenyl,
(d) benzyl, or
(e) α-methylbenzyl; and $R^{20}$ is:
(a) aryl, or
(b) heteroaryl, unsubstituted or substituted with one or two substituents selected from the group consisting of:
 (i) $(C_1-C_4)$-alkyl,
 (ii) $(C_1-C_4)$-alkoxyl,
 (iii) Br, Cl, I, F, or
 (iv) $CH_2$-aryl; and $R^{21}$ is:
(a) H, or
(b) $(C_1-C_4)$-alkyl, is unsubstituted or substituted with:
 i) $NH_2$,
 ii) $NH[(C_1-C_4)$-alkyl],
 iii) $N[(C_1-C_4)$-alkyl]$_2$,
 iv) $CO_2H$,
 v) $CO_2(C_1-C_4)$-alkyl,
 vi) OH,
 vii) $SO_3H$, or
 viii) $SO_2NH_2$; and $R^{22}$ is:
(a) H,
(b) $(C_1-C_4)$-alkyl,
(c) $(C_1-C_4)$-alkoxyl,
(d) aryl,
(e) aryl-$(C_1-C_4)$-alkyl,
(f) $CO_2R^{2a}$,
(g) $CON(R^2)_2$,
(h) $SO_2R^{2a}$,
(i) $SO_2N(R^2)_2$,
(j) $P(O)[(C_1-C_4)$-alkoxyl]$_2$, or
(k) imidazol-2-yl or imidazol-4-yl, in which the imidazole can be substituted with $(C_1-C_4)$-alkyl; and $R^{23}$ is:
(a) OH,
(b) $NR^2R^{21}$,
(c) $CO_2R^{2a}$,
(d) $CON(R^2)_2$,
(e) $S(O)_x-(C_1-C_4)$-alkyl, or
(f) $N(CH_2CH_2)_2Q$; and $R^{24}$ is:
(a) $(C_1-C_4)$-alkyl,
(b) $CHR^{25}-O-COR^{26}$,
(c) $CH_2CH_2-N[(C_1-C_2)$-alkyl]$_2$,
(d) $CH_2CH_2-N[CH_2CH_2]_2O$,
(e) $(CH_2CH_2O)_y-O-[(C_1-C_4)$-alkyl], wherein y is 1 or 2,
(f) aryl, or $-CH_2$-aryl, where aryl is as defined above or optionally substituted with $-CO_2-(C_1-C_4)$-alkyl, (g) 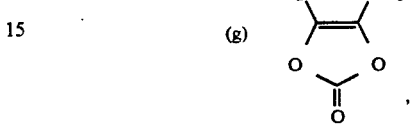

(h) 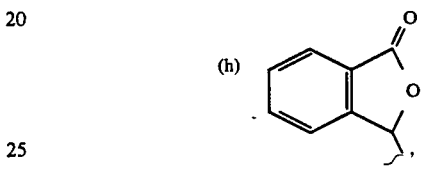

(i) 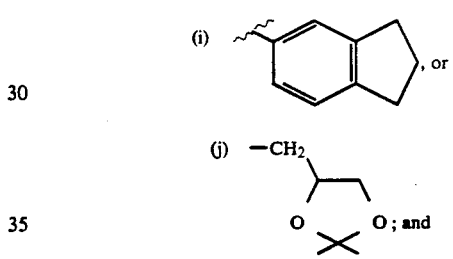, or (j) $-CH_2$
$\phantom{xxx}$ (dioxolane structure); and $R^{25}$ and $R^{26}$ independently are $(C_1-C_6)$-alkyl or phenyl.

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which ar modified so that each contains a carbon to carbon double bond or triple bond, respectively, such as vinyl, allyl and 2-butenyl.

Cycloalkyl denotes rings composed of 3 to 8 methlene groups, each which may be substituted or unsubstitued with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

Preferred Imidazoles

2-Butyl-1-[4-(1-carboxy-1-phenyl)methoxyphenyl]-methyl-4-chloro-5-hydroxymethylimidazole;

1-[4-(1-Carboxy-1-phenyl)methoxyphenyl]methyl-4-chloro-5-hydroxymethyl-2-propylimidazole;

2-Butyl-5-carboxy-1-[4-(1-carboxy-1-phenyl)methoxyphenyl]methyl-4-chloroimidazole;

2-Butyl-5-carbomethoxy-1-[4-(1-carboxy-1-phenyl)methoxyphenyl]methyl-4-chloroimidazole;

2-Butyl-5-carboxy-1-[4-(1-carboxy-1-phenyl)methoxyphenyl]methyl-4-pentafluoroethylimidazole;
2-Butyl-5-carboxy-1-[4-(1-carboxy-1-phenyl)methoxyphenyl]methyl-4-trifluoromethylimidazole;
2-Butyl-5-carboxy-1-[4-(1-carboxy-1-phenyl)methoxyphenyl]methyl-4-nitroimidazole;
2-Butyl-1-[4-(1-carboxy-1-phenyl)methoxyphenyl]methyl-5-hydroxymethyl-4-nitroimidazole;
2-Butyl-5-carbomethoxy-1-[4-(1-carboxy-1-phenyl)methoxyphenyl]methyl-4-nitroimidazole;
5-Carboxy-1-[4-(1-carboxy-1-(2-chloro)phenyl)methoxyphenyl]methyl-2-propyl-4-trifluoromethylimidazole;
5-Carboxy-2-propyl-1-[4-(1-carboxy-1-(2-methyl)phenyl)methoxyphenyl]methyl-4-trifluoromethylimidazole;
5-Carboxy-1-[4-(1-carboxy-1-(2,6-dichloro)phenyl)methoxyphenyl]methyl-2-propyl-4-trifluoromethylimidazole;
5-Carboxy-1-[4-(1-carboxy-1-(2-trifluoromethyl)phenyl)methoxyphenyl]methyl-2-propyl-4-trifluoromethylimidazole;
5-Carboxy-1-[4-(1-carboxy-1-(2-methoxy)phenyl)methoxyphenyl]methyl-2-propyl-4-trifluoromethylimidazole;
5-Carboxy-2-propyl-1-[4-(1-carboxy-1-(2-chloro)phenyl)methoxy-3-chlorophenyl]methyl-4-trifluoromethylimidazole;
5-Carboxy-1-[4-(1-carboxy-1-(2-chloro)phenyl)methoxy-3,5-dichlorophenyl]methyl-2-propyl-4-trifluoromethylimidazole;
5-Carboxy-1-[4-(1-carboxy-1-(2-chloro)phenyl)methoxyphenyl]methyl-4-chloro-2-propylimidazole;
5-Carboxy-1-[4-(1-carboxy-1-(2-methyl)phenyl)methoxyphenyl]methyl-4-chloro-2-propylimidazole;
5-Carboxy-1-[4-(1-carboxy-1-(2,6-dichloro)phenyl)methoxyphenyl]methyl-4-chloro-2-propylimidazole;
5-Carboxy-1-[4-(1-carboxy-1-(2-trifluoromethyl)phenyl)methoxyphenyl]methyl-4-chloro-2-propylimidazole;
5-Carboxy-1-[4-(1-carboxy-1-(2-methoxy)phenyl)methoxyphenyl]methyl-4-chloro-2-propylimidazole;
5-Carboxy-1-[4-(1-carboxy-1-(2-chloro)phenyl)methoxy-3-chlorophenyl]methyl-4-chloro-2-propylimidazole;
5-Carboxy-1-[4-(1-carboxy-1-(2-chloro)phenyl)methoxy-3,5-dichlorophenyl]methyl-4-chloro-2-propylimidazole;
2-Butyl-4-chloro-5-hydroxymethyl-1-[4-(1-(tetrazol-5-yl)-1-phenyl)methoxyphenyl]methylimidazole;
4-Chloro-5-hydroxymethyl-2-propyl-1-[4-(1-(tetrazol-5-yl)-1-phenyl)methoxyphenyl]methylimidazole;
2-Butyl-4-chloro-5-carboxy-1-[4-(1-(tetrazol-5-yl)-1-phenyl)methoxyphenyl]methylimidazole;
2-Butyl-4-chloro-5-carbomethoxy-1-[4-(1-(tetrazol-5-yl)-1-phenyl)methoxyphenyl]methylimidazole;
2-Butyl-5-carboxy-4-pentafluoroethyl-1-[4-(1-(tetrazol-5-yl)-1-phenyl)methoxyphenyl]methylimidazole;
2-Butyl-5-carboxy-1-[4-(1-(tetrazol-5-yl)-1-phenyl)methoxyphenyl]methyl-4-trifluoromethylimidazole;
2-Butyl-5-carboxy-4-nitro-1-[4-(1-(tetrazol-5-yl)-1-phenyl)methoxyphenyl]methylimidazole;
2-Butyl-5-hydroxymethyl-4-nitro-1-[4-(1-(tetrazol-5-yl)-1-phenyl)methoxyphenyl]methylimidazole;
2-Butyl-5-hydroxymethyl-4-nitro-1-[4-(1-(tetrazol-5-yl)-1-phenyl)methoxyphenyl]methylimidazole;
5-Carboxy-4-pentafluoroethyl-2-propyl-1-[4-(1-(tetrazol-5-yl)-1-(2-chloro)phenyl)methoxyphenyl]methylimidazole;
5-Carboxy-4-pentafluoroethyl-2-propyl-1-[4-(1-(tetrazol-5-yl)-1-(2-methyl)phenyl)methoxyphenyl]methylimidazole;
5-Carboxy-2-propyl-1-[4-(1-(tetrazol-5-yl)-1-(2,6-dichloro)phenyl)methoxyphenyl]methyl-4-pentafluoroethylimidazole;
5-Carboxy-4-pentafluoroethyl-2-propyl-1-[4-(1-(tetrazol-5-yl)-1-(2-trifluoromethyl)phenyl)methoxyphenyl]methylimidazole;
5-Carboxy-4-pentafluoroethyl-2-propyl-1-[4-(1-(tetrazol-5-yl)-1-(2-methoxy)phenyl)methoxyphenyl]methylimidazole;
5-Carboxy-4-pentafluoroethyl-2-propyl-1-[4-(1-(tetrazol-5-yl)-1-(2-chloro)phenyl)methoxy-3-chlorophenyl]methylimidazole;
5-Carboxy-4-pentafluoroethyl-2-propyl-1-[4-(1-(tetrazol-5-yl)-1-(2-chloro)phenyl)methoxy-3,5-dichlorophenyl]methylimidazole;
5-Carboxy-4-chloro-2-propyl-1-[4-(1-(tetrazol-5-yl)-1-(2-chloro)phenyl)methoxyphenyl]methylimidazole;
5-Carboxy-4-chloro-2-propyl-1-[4-(1-(tetrazol-5-yl)-1-(2-methyl)phenyl)methoxyphenyl]methylimidazole;
5-Carboxy-4-chloro-2-propyl-1-[4-(1-(tetrazol-5-yl)-1-(2,6-dichloro)phenyl)methoxyphenyl]methylimidazole;
5-Carboxy-4-chloro-2-propyl-1-[4-(1-(tetrazol-5-yl)-1-(2-trifluoromethyl)phenyl)methoxyphenyl]methylimidazole;
5-Carboxy-4-chloro-2-propyl-1-[4-(1-(tetrazol-5-yl)-1-(2-methoxy)phenyl)methoxyphenyl]methylimidazole;
5-carboxy-4-chloro-2-propyl-1-[4-(1-(tetrazol-5-yl)-1-(2-chloro)phenyl)methoxy-3-chlorophenyl]methylimidazole;
5-carboxy-4-chloro-2-propyl-1-[4-(1-(tetrazol-5-yl)-1-(2-chloro)phenyl)methoxy-3,5-dichlorophenyl]methylimidazole;
5-Carboxy-4-chloro-1-[4-(1-((N-phenylsulfonyl)carboxamido)-1-(2-chloro)phenyl)methoxyphenyl]methyl-2-propylimidazole;
5-Carboxy-1-[4-(1-((N-phenylsulfonyl)carboxamido-1-(2-chloro)phenyl)methoxyphenyl]methyl)-2-propyl-4-trifluoromethylimidazole;
5-Carboxy-1-[4-(1-carboxy-1-(2-chloro)phenyl)methoxyphenyl]methyl-2-propylimidazole;
5-Carboxy-1-[4-(1-carboxy-1-(2-methyl)phenyl)methoxyphenyl]methyl-2-propylimidazole;
5-Carboxy-1-[4-(1-carboxy-1-(2-trifluoromethyl)phenyl)methoxyphenyl]methyl-2-propylimidazole;
5-Carboxy-1-[4-(1-carboxy-1-(2-ethyl)phenyl)methoxyphenyl]methyl-2-propylimidazole;
5-Carbomethoxy-1-[4-(1-carboxy-1-(2-chloro)phenyl)methoxyphenyl]methyl-2-propylimidazole;
5-Carbomethoxy-1-[4-(1-carboxy-1-(2-methyl)phenyl)methoxyphenyl]methyl-2-propylimidazole;
5-Carbomethoxy-1-[4-(1-carboxy-1-(2-trifluoromethyl)phenyl)methoxyphenyl]methyl-2-propylimidazole;
5-Carbomethoxy-1-[4-(1-carboxy-1-(2-ethyl)phenyl)methoxyphenyl]methyl-2-propylimidazole;
5-Carboxy-1-[4-(1-carbomethoxy-1-(2-chloro)phenyl)methoxyphenyl]methyl-2-propylimidazole;
5-Carboxy-1-[4-(1-carbomethoxy-1-(2-methyl)phenyl)methoxyphenyl]methyl-2-propylimidazole;
5-Carboxy-1-[4-(1-carbomethoxy-1-(2-trifluoromethyl)phenyl)methoxyphenyl]methyl-2-propylimidazole;

5-Carboxy-1-[4-(1-carbomethoxy-1-(2-ethyl)phenyl)methoxyphenyl]methyl-2-propylimidazole;

5-Carboxy-1-[4-(1-(tetrazol-5-yl)-1-(2-chloro)phenyl)methoxyphenyl]methyl-2-propylimidazole;

5-Carboxy-1-[4-(1-(tetrazol-5-yl)-1-(2-methyl)phenyl)methoxyphenyl]methyl-2-propylimidazole;

5-Carboxy-1-[4-(1-(tetrazol-5-yl)-1-(2-trifluoromethyl)phenyl)methoxyphenyl]methyl-2-propylimidazole;

5-Carboxy-1-[4-(1-(tetrazol-5-yl)-1-(2-ethyl)phenyl)methoxyphenyl]methyl-2-propylimidazole;

5-Carboxy-1-[4-(1-(N-methylsulfonylcarboxamido)-1-(2-chloro)phenyl)methoxyphenyl]methyl-2-propylimidazole;

5-Carboxy-1-[4-(1-(N-methylsulfonylcarboxamido)-1-(2-methyl)phenyl)methoxyphenyl]methyl-2-propylimidazole;

5-Carboxy-1-[4-(1-(N-methylsulfonylcarboxamido)-1-(2-trifluoromethyl)phenyl)methoxyphenyl]methyl-2-propylimidazole;

5-Carboxy-1-[4-(1-(N-methylsulfonylcarboxamido)-1-(2-ethyl)phenyl)methoxyphenyl]methyl-2-propylimidazole;

5-Carbomethoxy-1-[4-(1-(N-methylsulfonylcarboxamido)-1-(2-chloro)phenyl)methoxyphenyl]methyl-2-propylimidazole;

5-Carbomethoxy-1-[4-(1-(N-methylsulfonylcarboxamido)-1-(2-methyl)phenyl)methoxyphenyl]methyl-2-propylimidazole;

5-Carbomethoxy-1-[4-(1-(N-methylsulfonylcarboxamido)-1-(2-trifluoromethyl)phenyl)methoxyphenyl]methyl-2-propylimidazole;

5-Carbomethoxy-1-[4-(1-(N-methylsulfonylcarboxamido)-1-(2-ethyl)phenyl)methoxyphenyl]methyl-2-propylimidazole;

4-Acetamido-2-butyl-5-carboxy-1-[4-(1-carboxy-1-(2-chloro)phenyl)methoxyphenyl]methylimidazole;

4-Acetamido-2-butyl-5-carboxy-1-[4-(1-carboxy-1-(2-methyl)phenyl)methoxyphenyl]methylimidazole;

4-Acetamido-2-butyl-5-carboxy-1-[4-(1-carboxy-1-(2-trifluoromethyl)phenyl)methoxyphenyl]methylimidazole;

4-Acetamido-2-butyl-5-carboxy-1-[4-(1-carboxy-1-(2-ethyl)phenyl)methoxyphenyl]methylimidazole;

4-(N-Acetyl-N-methyl)amino-2-butyl-5-carboxy-1-[4-(1-carboxy-1-(2-chloro)phenyl)methoxyphenyl]methylimidazole;

4-(N-Acetyl-N-methyl)amino-2-butyl-5-carboxy-1-[4-(1-carboxy-1-(2-methyl)phenyl)methoxyphenyl]methylimidazole;

4-(N-Acetyl-N-methyl)amino-2-butyl-5-carboxy-1-[4-(1-carboxy-1-(2-trifluoromethyl)phenyl)methoxyphenyl]methylimidazole;

4-(N-Acetyl-N-methyl)amino-2-butyl-5-carboxy-1-[4-(1-carboxy-1-(2-ethyl)phenyl)methoxyphenyl]methylimidazole;

4-(N-Acetyl-N-methyl)amino-2-butyl-5-carboxy-1-[4-(1-carbomethoxy-1-(2-chloro)phenyl)methoxyphenyl]methylimidazole;

4-(N-Acetyl-N-methyl)amino-2-butyl-5-carboxy-1-[4-(1-carbomethoxy-1-(2-methyl)phenyl)methoxyphenyl]methylimidazole;

4-(N-Acetyl-N-methyl)amino-2-butyl-5-carboxy-1-[4-(1-carbomethoxy-1-(2-trifluoromethyl)phenyl)methoxyphenyl]methylimidazole;

4-(N-Acetyl-N-methyl)amino-2-butyl-5-carboxy-1-[4-(1-carbomethoxy-1-(2-ethyl)phenyl)methoxyphenyl]methylimidazole;

5-Carboxy-4-chloro-1-[4-(1-(N-(2-chloro)phenylsulfonyl)carboxamido-1-(2-chloro)phenyl)methoxyphenyl]methyl-2-propylimidazole;

5-Carboxy-4-chloro-1-[4-(1-(N-phenylsulfonyl)carboxamido-1-(2-chloro)phenyl)methoxyphenyl]methyl-2-pentafluoroethylimidazole;

5-Carboxy-4-chloro-1-[4-(1-(N-methylsulfonyl)carboxamido-1-(2-chloro)phenyl)methoxyphenyl]methyl-2-propylimidazole;

5-Carboxy-4-chloro-1-[4-(1-(N-methylsulfonyl)carboxamido-1-(2-chloro)phenyl)methoxyphenyl]methyl-4-chloro-2-pentafluoroethylimidazole;

5-Carboxy-4-chloro-2-propyl-1-[4-(1-(N-trifluoromethylsulfonyl)carboxamido-1-(2-chloro)phenyl)methoxyphenyl]methylimidazole;

5-Carboxy-4-chloro-2-pentafluoroethyl-1-[4-(1-(N-trifluoromethylsulfonyl)carboxamido-1-(2-chloro)phenyl)methoxyphenyl]methylimidazole;

5-Carboxy-4-chloro-2-propyl-1-[4-(1-(N-(pyridin-4-yl)sulfonyl)carboxamido-1-(2-chloro)phenyl)methoxyphenyl]methylimidazole;

5-Carboxy-4-chloro-2-pentafluoroethyl-1-[4-(1-(N-(pyridin-4-yl)sulfonyl)carboxamido-1-(2-chloro)phenyl)methoxyphenyl]methylimidazole.

GENERAL METHODS FOR PREPARATION OF COMPOUNDS OF GENERAL FORMULA I

The methods described below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by Formula I and a substituted benzyl substitutent which is attached to the heterocyclic component at a nitrogen atom. Thus, two generally applicable approaches to antagonists of formula I are these:

1. A substituted imidazole is prepared as described below. Then the imidazole is alkylated at a nitrogen atom with a substituted benzyl halide or pseudohalide giving an alkylated imidazole in the Schemes below, this alkylating agent is often designated as "ArCH$_2$—Q where Q is a halide (—Cl,Br,I) or pseudoliaide (—OMs, OTs, OTf). In some cases, alkylation may take place at both nitrogen atoms of the imidazole, and in these cases, separation by fractional crystallization or by chromotographic methods may be necessary for isolation of the desired product. In some cases, the alkylation step produces a fully-assembled antagonist of Formula I, except that functional groups in the alkylating agent or in the imidazole may be present in protected form and require deprotection steps to be carried out to complete the synthesis. In other cases, the alkylation is carried out with a substituted benzylic halide or pseudohalide ("ArCH$_2$—Q"), but here the alkylation step is followed by subsequent steps which are required to assemble the substituted benzyl element of the antagonist of Formula I. The alkylation steps and subsequent steps used to prepare antagonists of formula I, are described below.

2. In another approach to antagonists of formula I, a substituted benzyl element is introduced at the beginning of, or during the preparation of the imidazole.

Routes of this type are illustrated below. In most cases where this general approach is used, the substituted benzyl component which is introduced during the synthesis of the heterocycle must be subjected to further synthetic transformations in order to complete the synthesis of the antagonist of Formula I. In the Schemes shown below, this substituted benzyl component is designated as "—CH$_2$Ar," and is usually introduced by an alkylation step with a substituted benzyl halide or pseudohalide designated ArCH$_2$—Q (where Q is, for example, Cl, Br, I, F, OTs, or OMs), or is introduced by a route which starts with a substituted benzylamine, designated "ArCH$_2$NH$_2$". The required substituted benzylamine derivatives may be prepared by standard methods, for example from the substituted benzylic halides or pseudohalides ("Ar—CH$_2$Q"). Substituted benzyl halides or pseudohalides which are useful in the preparation of alkylated imidazoles described are illustrated by those listed below in Table 1. Substituted benzyl amines which are useful in the preparation of the alkylated heterocycles described are illustrated by those listed below in Table 2. In cases where these benzylic halides, pseudohalides and amines are not commercially available, they are prepared as described below or by standard methods of organic synthesis. Subsequent steps which may be required to complete the synthesis of antagonists of Formula I are described below.

The compounds of this invention maybe resolved using the techniques known in the art. The diastereomeric salts and esters of the enantiomers are separated and the desired compound is the more active stereoisomer. The compounds of this invention, their pharmaceutically acceptable salts and their prodrug forms are included within the scope of this invention.

TABLE 1

[Structures of substituted benzyl bromides: CH$_2$Br-substituted benzenes with various substituents including OCH$_2$Ph, OCH$_3$, CH$_3$, Cl, CN, CO$_2$CH$_3$, CH$_2$OTBDMS, SCH$_2$Ph, NO$_2$, CH$_2$OTs]

TABLE 2

[Structures of substituted benzylamines: CH$_2$NH$_2$-substituted benzenes with various substituents including NO$_2$, OCH$_2$Ph, CO$_2$CH$_3$, CN, CH$_3$, CH$_2$OTBDMS, SCH$_2$Ph, Cl]

Abbreviations used in schemes and examples are listed in Table 3.

TABLE 3

| Reagents | |
|---|---|
| NBS | N-bromosuccinimide |
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| DIPEA | Diisopropylethylamine |
| TBS-Cl | Tributylsilyl chloride |
| TBAF | tetrabutylammonium fluoride |
| TMSCN | trimethylsilyl cyanide |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| HMPA | hexamethylphosphoramide |
| Others: | |
| Phe | phenylalanine |
| rt | room temperature |
| TBDMS | t-butyldimethylsilyl |
| OTf | OSO$_2$CF$_3$ |
| Ph | phenyl |
| FAB-MS (FSBMS) | Fast atom bombardment mass spectroscopy |
| NOE | Nuclear Overhauser Effect |
| SiO$_2$ | silica gel |
| trityl | triphenylmethyl |
| Bn | benzyl |

PART I

Preparation of the Imidazoles of Formula I

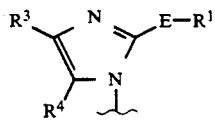

The imidazoles required in for alkylation to the substituted benzyl element can be prepared by a number of methods well known in the literature including those described in EPO publications 253,310 and 324,377 by DuPont and EPO publication by Merck 401,030.

PART II

Preparation of Substituted Benzyl Derivatives of the General Formula I

The synthesis of Angiotensin II Antagonists incorporating a substituted benzyl group as shown in Formula I may be accomplished by reactions in the presence of a base of an imidazole with a benzylic compound bearing a good leaving group, and the appropriate substituents $R^9$, $R^{10}$, $R^{11}$, $R^{12}$, X, Y and Z as shown in Formula I. Alternatively, compounds with structures according to Formula I may also be synthesized in stages from a benzyl-substituted imidazole which contains the substituents $R^9$, $R^{10}$ and X, followed by reaction with an intermediate (such as a substituted alpha-bromophenylacetic ester) which introduces the substituents at $R^{11}$, $R^{12}$ and Z. Examples of this latter methodology in which a benzyl-substituted heterocyclic intermediate is prepared first, and then elaborated to afford compounds with structures described by Formula I, are shown in the Schemes II-1, II-2 and II-3. The preparation of compound 5 of Formula I wherein: E=a single bond, $R^9$, $R^{10}$ and $R^{11}$ are H, X=O, Y=a single bond, Z=CO$_2$H and $R^{12}$=phenyl appears in Scheme II-1. Deprotonation of a substituted imidazole with strong bases such as sodium hydride or potassium tert-butoxide in DMF for a period of 1-24 hours at temperatures of 20°-100° C., followed by alkylation with 4-benzyloxybenzyl chloride affords the protected ether 2. The benzyl ether is next removed by hydrogenolysis using hydrogen and an appropriate catalyst such as Pd/C, Pd(OH)$_2$/C or Pt/C which affords the intermediate phenol 3. The phenolic proton is then abstracted, and the phenolate is alkylated with methyl 2-bromophenylacetate to furnish ester 4. Finally, the ester is hydrolyzed and the free acid 5 is obtained.

SCHEME II-1

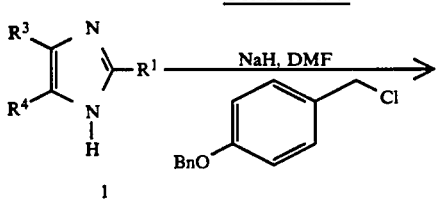

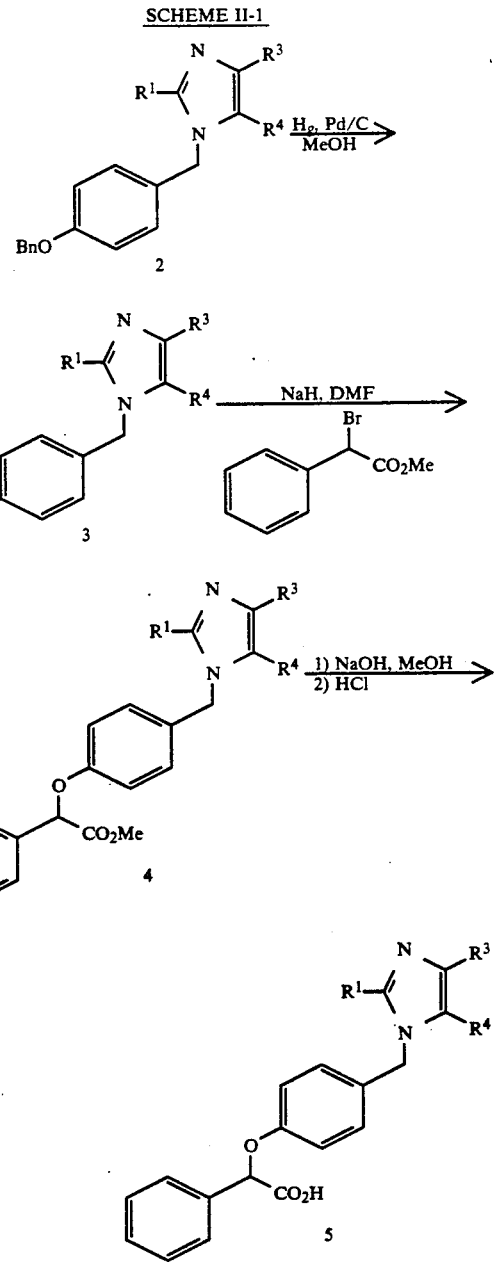

The synthesis of compound 10 of Formula I wherein: E=a single bond, $R^9$, $R^{10}$ and $R^{11}$ are H, X=O, Y=a single bond, Z=CO$_2$H and $R^{12}$=phenyl is presented in Scheme II-2. Deprotonation of a substituted imidazole (6) with sodium hydride in DMF, followed by treatment with 4-benzyloxybenzyl chloride gives compound 7. The benzyl ether is removed by hydrogenolysis to give the phenol 8, which is then deprotonated with potassium hydride and 18-crown-6 in DMF and alkylated with methyl 2-bromophenylacetate to give the ester 9. Basic hydrolysis of 9 gives the free acid 10. Alkylation of the phenol 8 with substituted 2-bromophenylacetic esters, followed by ester hydrolysis leads to compounds of Formula I where $R^{12}$ is a substituted phenyl group.

SCHEME II-2

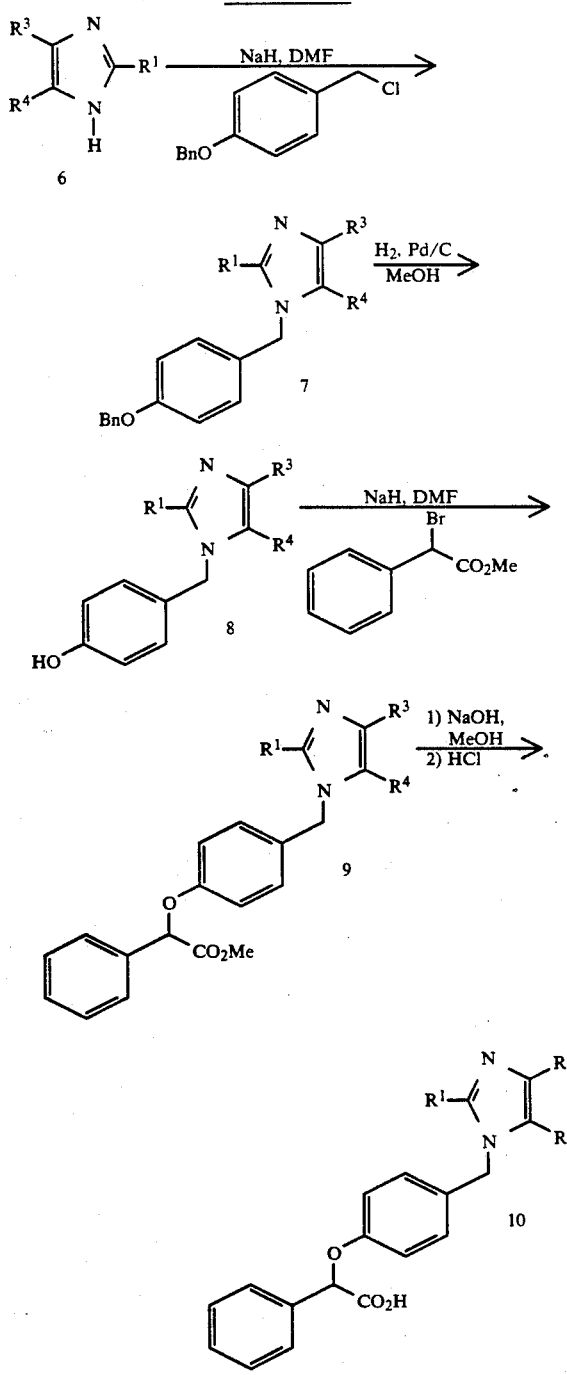

SCHEME II-3

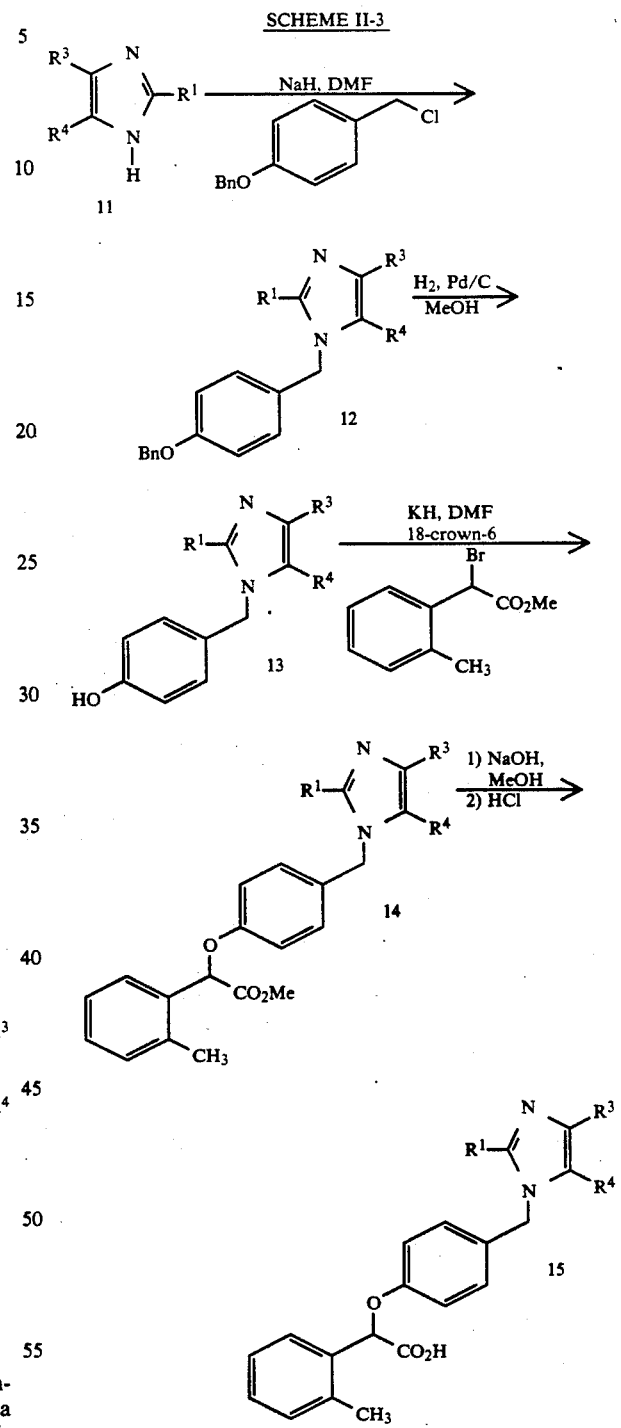

followed by alkaline hydrolysis leads to additional derivatives in this imidazole series.

The synthesis of compound 15 of Formula I wherein :E=a single bond, $R^9$, $R^{10}$ and $R^{11}$ are H, X=O, Y=a single bond, Z=CO$_2$H and $R^{12}$=2-methylphenyl is shown in Scheme II-3. Deprotonation of imidazole (11) with a strong base such as sodium hydride in DMF, followed by treatment with 4-benzyloxybenzyl chloride produces the ether 12. The benzyl ether is removed by hydrogenolysis to give the phenol 13, which is then deprotonated with potassium hydride and 18-crown-6 in DMF and alkylated with methyl 2-bromo-2′-methylphenylacetate to give the ester 14. Alkaline hydrolysis of 14 gives the free acid 15. Reaction of the phenol 13 with other substituted alpha-bromophenylacetic esters Substituted 2-bromophenylacetic esters are typically employed in the synthesis of compounds of general Formula I when it is desired that $R^{12}$ be a substituted phenyl group, $R^{11}$ is hydrogen, Y is a single bond and Z is a carboxylic acid. These substituted 2-bromophenylacetic esters are readily prepared from substituted phenyl acetic acids (16) by a Hell-Volhard-Zelinsky reaction as shown in Scheme II-4. Alternatively, substituted 2-bromophenylacetic esters may also be obtained from benzaldehydes (18) as shown in Scheme II-5. Reaction of the substituted benzaldehydes (18) with trimethylsilyl cyanide affords the trimethylsilyl-cyanohydrins 19. Treatment of 19 with acidic ethanol produces the hydroxy esters 20, and subsequent reaction with carbon tetrabromide and triphenylphosphine provides the substituted 2-bromophenylacetic esters 17.

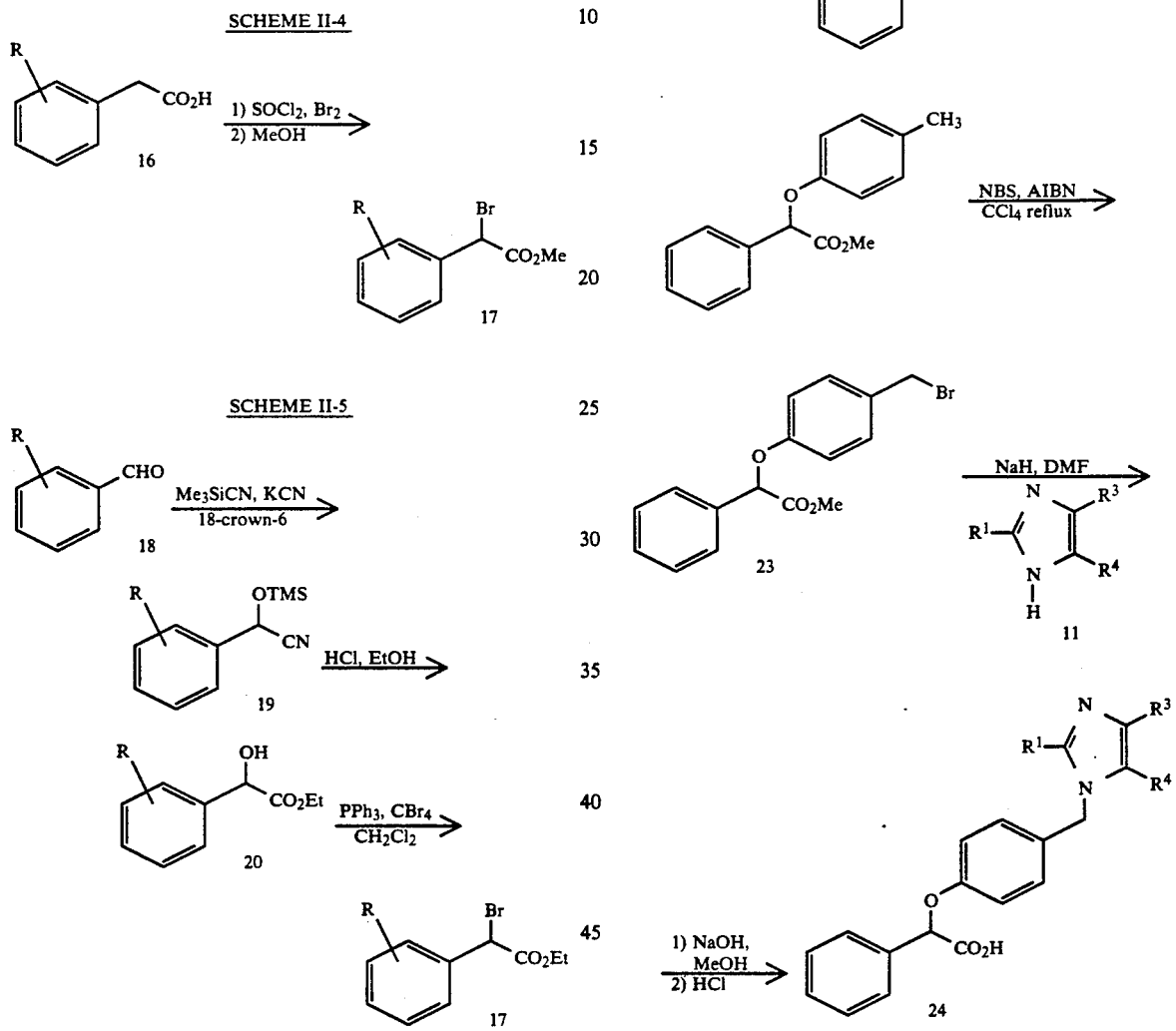

The synthesis of Angiotensin II Antagonists incorporating a substituted benzyl element defined by Formula I may also be accomplished by the alkylation reaction of an imidazole with a benzylic intermediate bearing a good leaving group, and with all of the appropriate substituents $R^9$, $R^{10}$, $R^{11}$, $R^{12}$, X, Y and Z in place. This approach, which is generally preferred when either $R^9$ or $R^{10}$ are non-hydrogen, is illustrated in Scheme II-6. Deprotonation of p-cresol (21) with strong bases such as potassium hydride or potassium tert-butoxide in DMF and alkylation with methyl 2-bromo-2-phenylacetate gives the ether 22. Bromination of 22 at the benzylic methyl group with N-bromosuccinimide gives the alkylating agent 23. Deprotonation of imidazole (11) with sodium hydride in DMF, followed by reaction with bromide 23, and subsequent ester hydrolysis provides the acid 24.

A strategy similar to that of Scheme II-6 is applied when substitution at $R^{11}$ is desired as shown in Scheme II-7. Intermediate ethers such as 22 in Scheme II-6 are deprotonated with strong bases such as lithium bis(trimethylsilyl)amide in THF and can then be reacted with an alkylating agent such as an alkyl halide or mesylate. In this case, reaction of the anion derived from ether 22 with methyl iodide affords the alkylated product 25. Reaction of 25 with N-bromosuccinimide gives bromide 26, which is in turn used for alkylation of the imidazole. Scheme II-7 illustrates the alkylation of imidazole 6 with bromide 26 which after ester hydrolysis affords acid 27.

SCHEME II-7

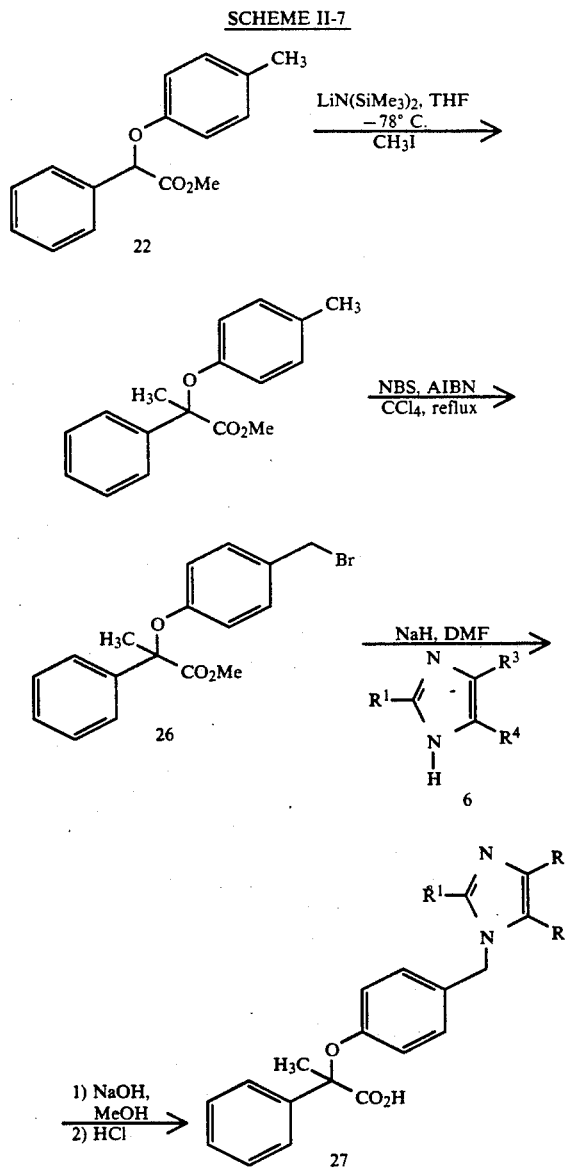

SCHEME II-8

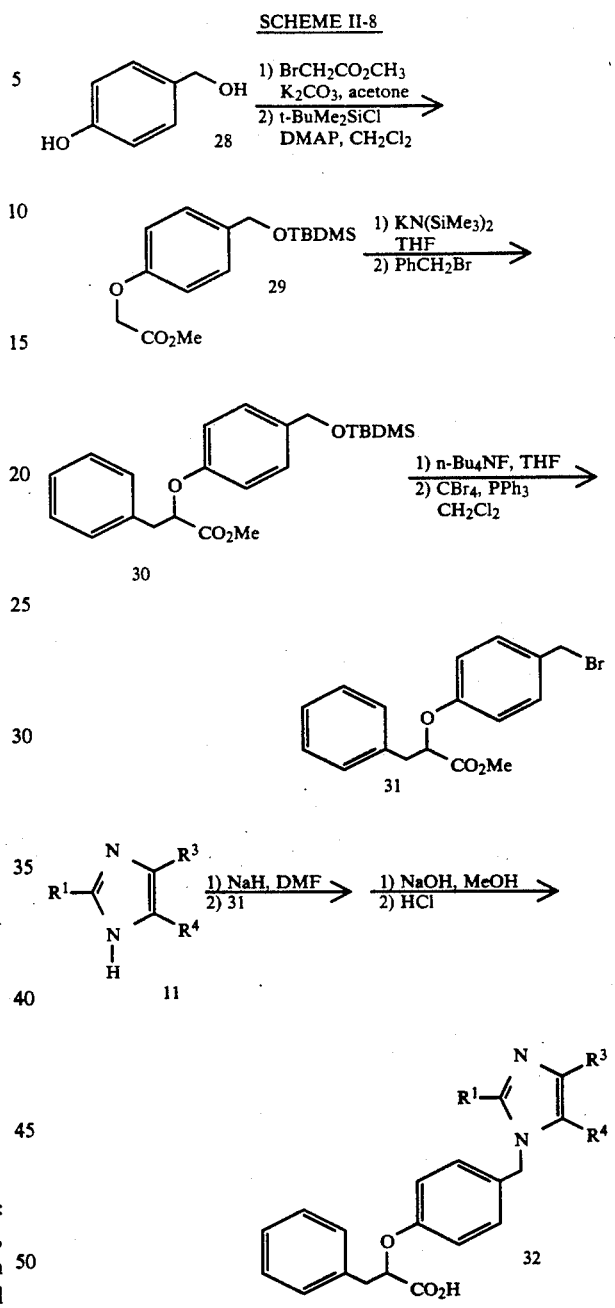

The synthesis of compound 32 of Formula I wherein: E=a single bond, $R^9$, $R^{10}$ and $R^{11}$ are H, X=O, Y=$CH_2$, Z=$CO_2H$ and $R^{12}$=phenyl is shown in Scheme II-8. In this example, p-hydroxybenzyl alcohol (28) is selectively alkylated at the phenolic hydroxyl group with methyl bromoacetate when they are refluxed with potassium carbonate in acetone. After the remaining hydroxyl group is protected as a tert-butyldimethylsilylether, this ether (29) may then be deprotonated with a strong base such as potassium bis(trimethylsilyl)amide and reacted with an alkylating agent in a manner similar to that shown for intermediate 22 in Scheme II-7. Alkylation of ether 29 with benzyl bromide provides 30. Silylether hydrolysis of 30 and bromination of the resulting alcohol affords an alkylating agent (31) which is then used to alkylate the imidazole. Alkylation of the anion derived from imidazole 11, followed by ester hydrolysis affords the acid 32 shown in Scheme II-8.

Scheme II-9 illustrates the preparation of an antagonist of Formula I wherein: E=a single bond, $R^9$, $R^{10}$ and $R^{11}$ are H, X is a single bond, Y=O, Z=$CO_2H$ and, $R^{12}$=phenyl. In this example, the Hell-Volhard-Zelinsky reaction converts 4'-methylphenylacetic acid (33) to the alpha-bromoester 34, which is in turn reacted with the potassium salt of phenol to yield 35. Benzylic bromination of 35 provides alkylating agent 36 which is then reacted with an imidazole. When the sodium salt of imidazole 6 is alkylated with the bromide 36 in DMF, ester 37 is obtained. Alkaline hydrolysis of ester 37 then provides acid 38.

SCHEME II-9

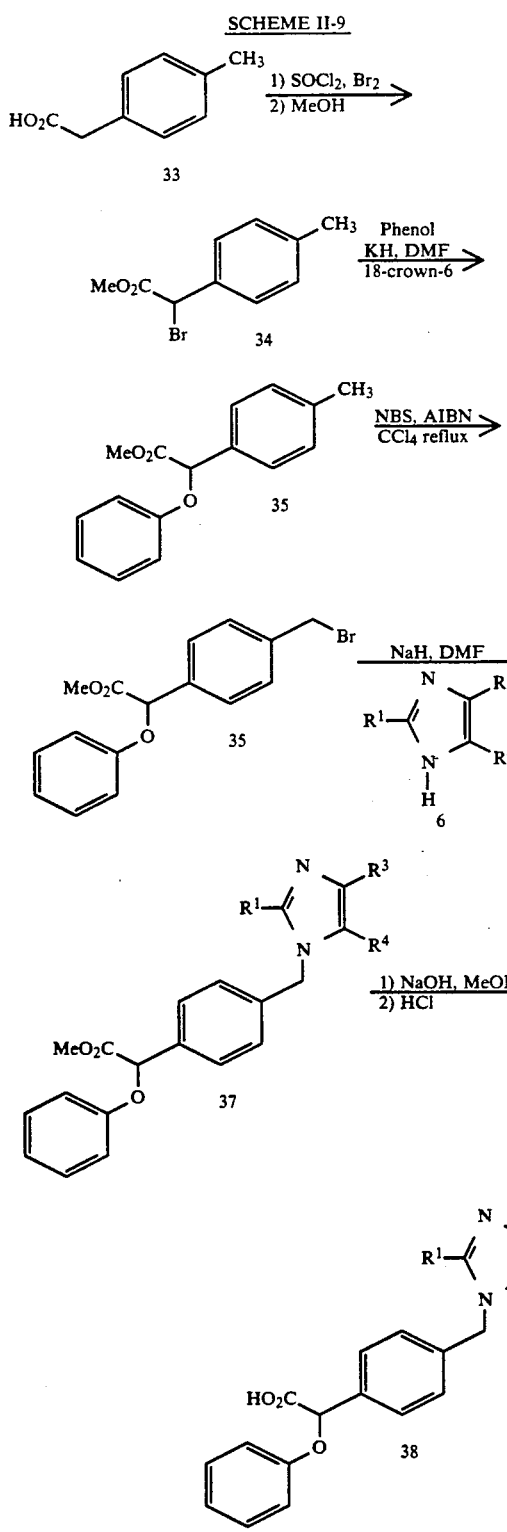

dehydrated to the trans-stilbene derivative 40, and then benzylic bromination of 40 gives the alkylating agent 41. Deprotonation of heterocycle 6 with sodium hydride in DMF and treatment with 41 gives ester 42. Alkaline hydrolysis of 42 affords the product 43, in which X is a methyne group ($R^{11}$ is absent) doubly bonded to the carbon atom bearing substituents $R^{12}$ and Z as shown in Scheme II-11. Catalytic hydrogenation of 43 gives the derivative 44 where X is a methylene group and $R^{11}$ is a hydrogen atom (Scheme II-11).

SCHEME II-10

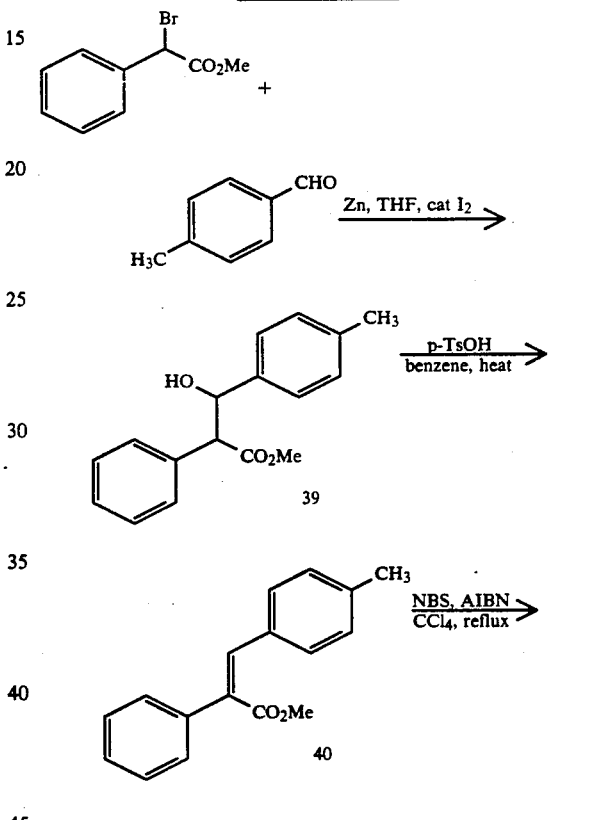

Schemes II-10 and II-11 illustrate the preparation of analogs where E=a single bond, $R^9$ and $R^{10}$ are H, Y=a single bond, $R^{12}$ is phenyl, Z=CO2H and X is either methyne or methylene. A Reformatsky reaction is first employed to prepare methyl 3-hydroxy-3-(4-methylphenyl)-2-phenylpropanoate (39) from the starting materials shown in Scheme II-10. When heated in the presence of p-toluenesulfonic acid in benzene 39 is

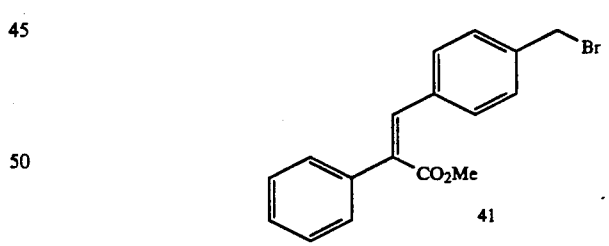

SCHEME II-11

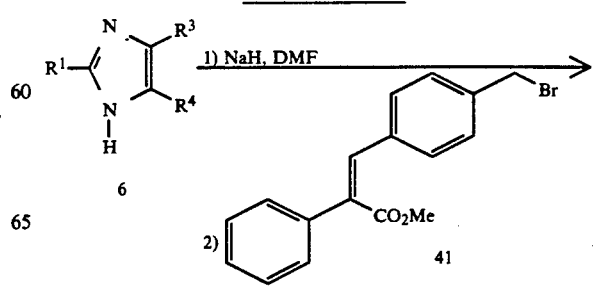

-continued
SCHEME II-11

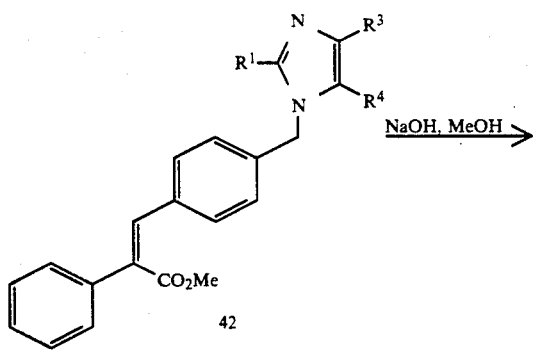

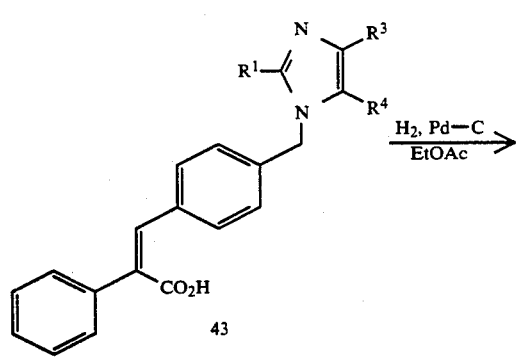

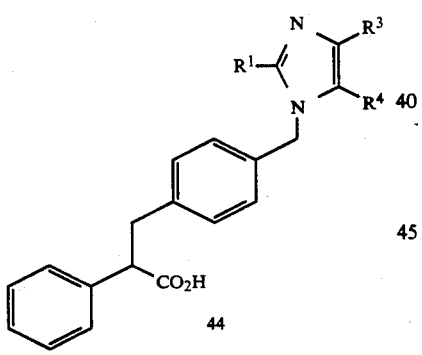

The synthesis of compound 47 of Formula I which has the same substituents as compound 10 (Scheme II-2) with the exception that Z is a tetrazol-5-yl group, is illustrated in Scheme II-12. Exposure of ester 9 to excess ammonia in methanol produces the corresponding amide which is then dehydrated with phosphorous oxychloride and triethylamine to give the nitrile 45. Reaction of the nitrile 45 with trimethylstannyl azide in refluxing toluene provides the tetrazole derivative 46.

SCHEME II-12

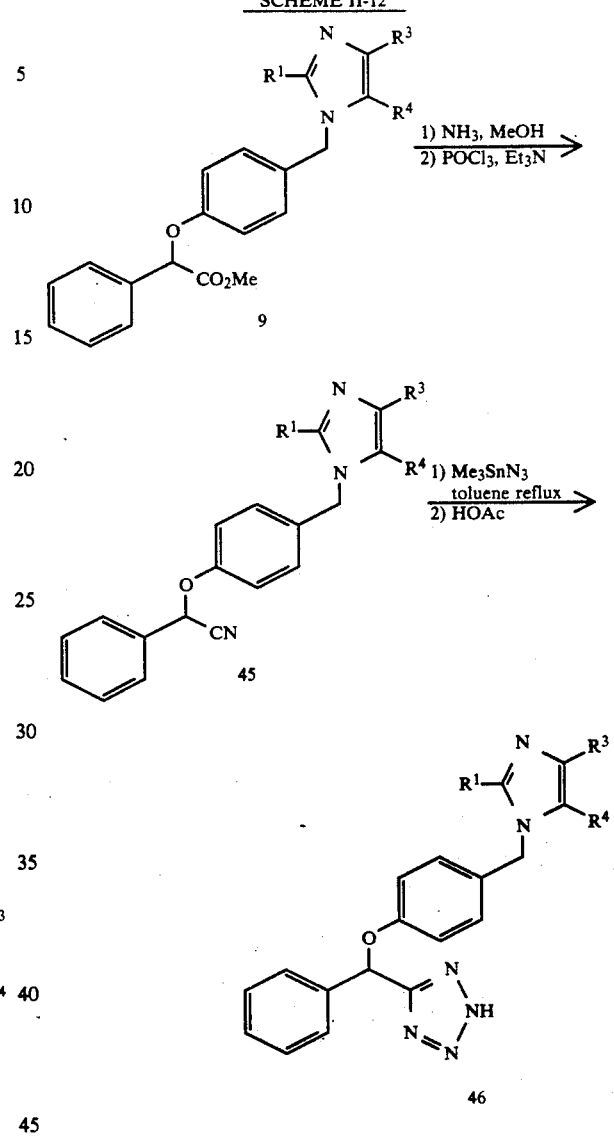

Scheme II-13 illustrates the preparation of a tetrazole analog (52) similar to structure 46 wherein $R^{12}$ is a 2-chlorophenyl group. In this synthesis, the ester group of intermediate 47 is converted to a nitrile prior to alkylating a substituted imidazole (Part I) with this substituted benzyl element. Thus, reaction of ester 47 with ammonia in methanol, followed by dehydration of amide 48 produces nitrile 49. Benzylic bromination affords 50, which is then reacted with the sodium salt of heterocycle 6 in DMF to give intermediate 51. Finally, reaction of nitrile 51 with trimethylstannyl azide in refluxing toluene gives the tetrazole 52 shown in Scheme II-13.

SCHEME II-13

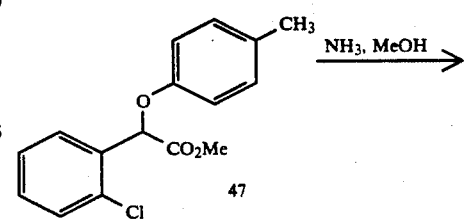

SCHEME II-13

-continued

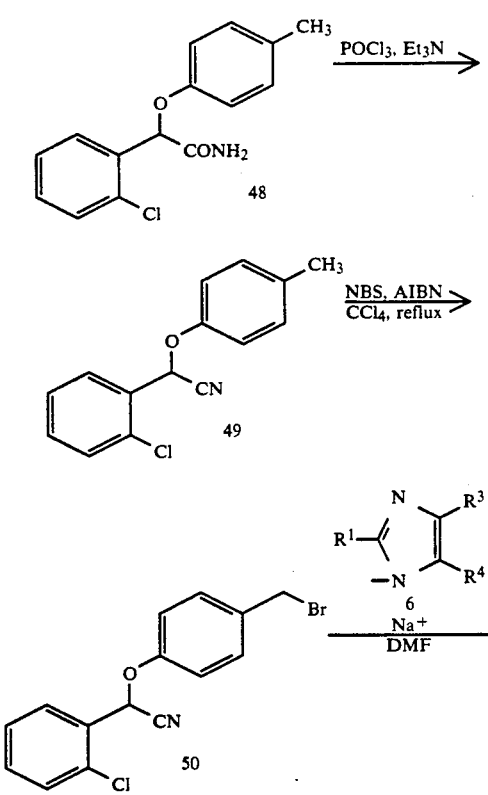

then alkylated with bromide 53 (preparation of bromide 53 is shown in Scheme II-14) to yield nitrile 54. The silylether group in compound 54 is directly converted to the bromide 55 by treatment with carbon tetrabromide, triphenylphosphine and acetone in dichloromethane (Mattes, H.; Benezra, C. Tetrahedron Lett., 1987, 1697). Alkylation of the sodium salt of imidazole 6 with bromide 55, followed by reaction of 56 with trimethylstannyl azide in refluxing toluene, yields the tetrazole 57.

SCHEME II-14

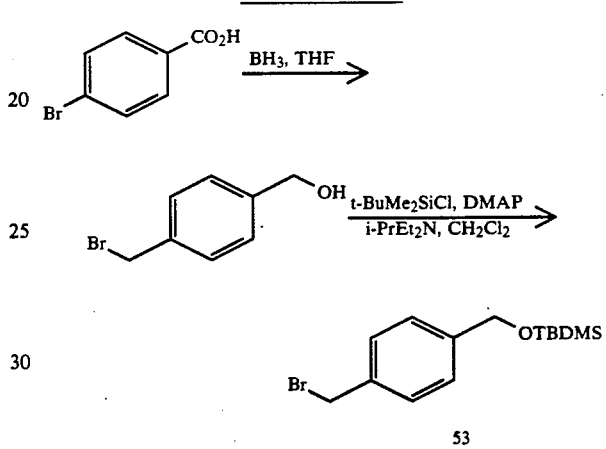

SCHEME II-15

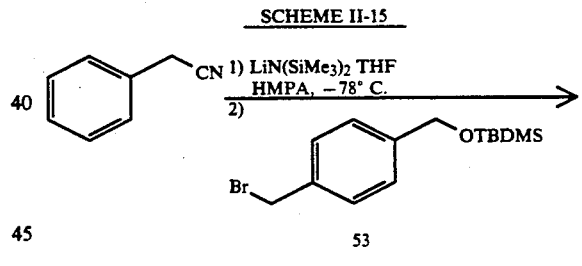

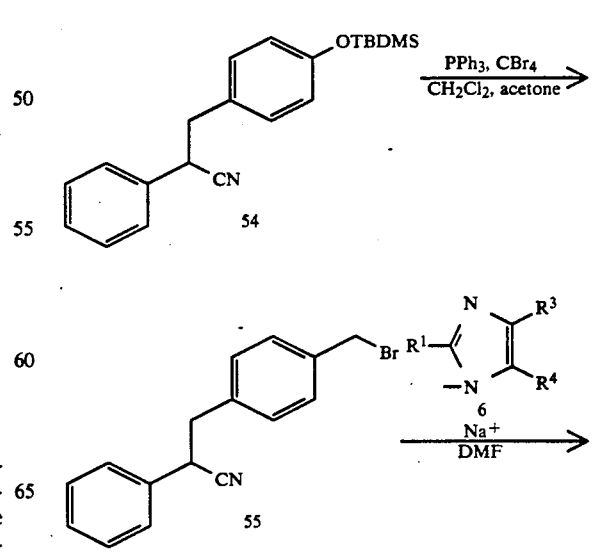

The preparation of a derivative of Formula I analogous to tetrazole 47 (Scheme II-12) which has a methylene group for the X substituent, is shown in Scheme II-15. In this synthesis, phenylacetonitrile is deprotonated with lithium bis(trimethylsilyl)amide and

29
-continued
SCHEME II-15

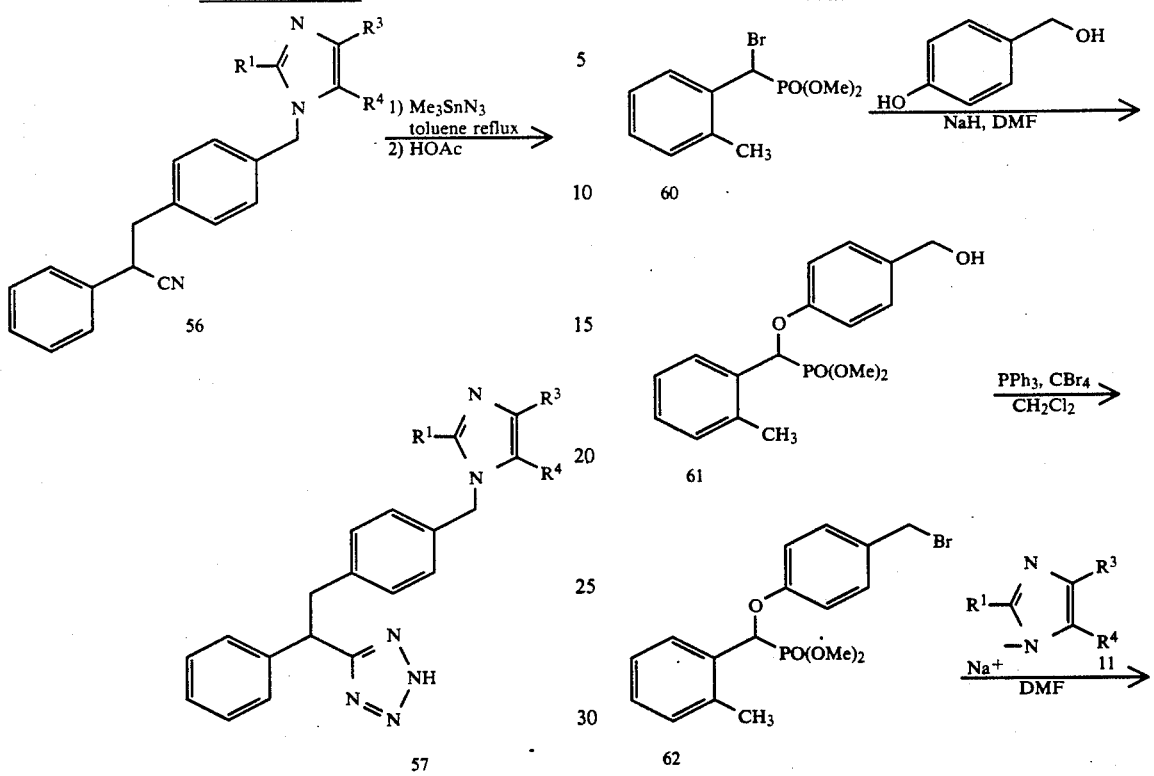

Scheme II-16 illustrates the preparation of a derivative of Formula I where E is a single bond, $R^9$, $R^{10}$ and $R^{11}$ are H, X=O, Y=a single bond, $R^{12}$ is 2-methylphenyl, and Z is a phosphonic acid group. Reaction of o-tolualdehyde (58) with dimethylphosphite in the presence of triethylamine affords the phosphonate ester 59. Bromination of the hydroxyl group of 59 with carbon tetrabromide and triphenylphosphine in dichloromethane gives bromide 60. Deprotonation of p-hydroxybenzyl alcohol with sodium hydride in DMF followed by addition of bromide 60 affords intermediate 61. A second bromination reaction (CBr4, PPh3, CH2Cl2) converts alcohol 61 to the bromide 62 which is then used to alkylate the imidazole. Scheme II-16 illustrates the case where the anion of imidazole 11 is reacted with bromide 62 to give upon workup, the phosphonate mono-ester 63. Phosphonic acid 64 may be obtained by treatment of ester 63 with trimethylsilyl bromide.

SCHEME II-16

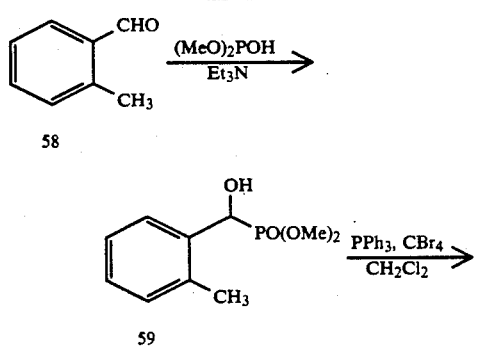

The synthesis of a derivative of Formula I where Z is an acyl-sulfonamide group is illustrated in Scheme II-17. Alkylation of the anion derived from heterocycle 11 with bromide 65 (synthesis described in Example 28 of the experimental section) and alkaline hydrolysis of the resulting ester (66) affords the acid 67. Reaction of acid 67 with 1,1'-carbonyldiimidazole in THF at elevated temperatures gives an acylimidazolide which may be reacted with a sulfonamide (benzenesulfonamide in this example) and DBU in THF to provide the target compound (68) where Z is the acyl-sulfonamide group.

substituents $R^9$ or $R^{10}$ are non-hydrogen include substituted p-cresols (Scheme II-6), 4-hydroxybenzyl alcohols, 4-hydroxybenzaldehydes, 4-hydroxybenzoic acids and their esters as shown in Schemes II-18 thru II-20.

Commercially available benzyl alcohols such as 3-chloro-4-hydroxy-5-methoxybenzyl alcohol may be selectively alkylated by alpha-bromophenylacetic esters when they are refluxed together in the presence of bases such as anhydrous potassium carbonate, giving 2-phenoxyesters like 69 shown in Scheme II-18. Conversion of the benzyl alcohol group in 69 to a bromide ($CBr_4$, $PPh_3$, $CH_2Cl_2$) affords an alkylating agent (70). An imidazole is then alkylated with bromide 70; hydrolysis of the intermediate ester affords 71. Alternatively, the imidazole may be directly coupled with benzyl alcohols like 69 using Mitsunobu reaction conditions (diethyl azodicarboxylate, $PPh_3$, THF). Again, hydrolysis of the resulting ester completes the synthesis.

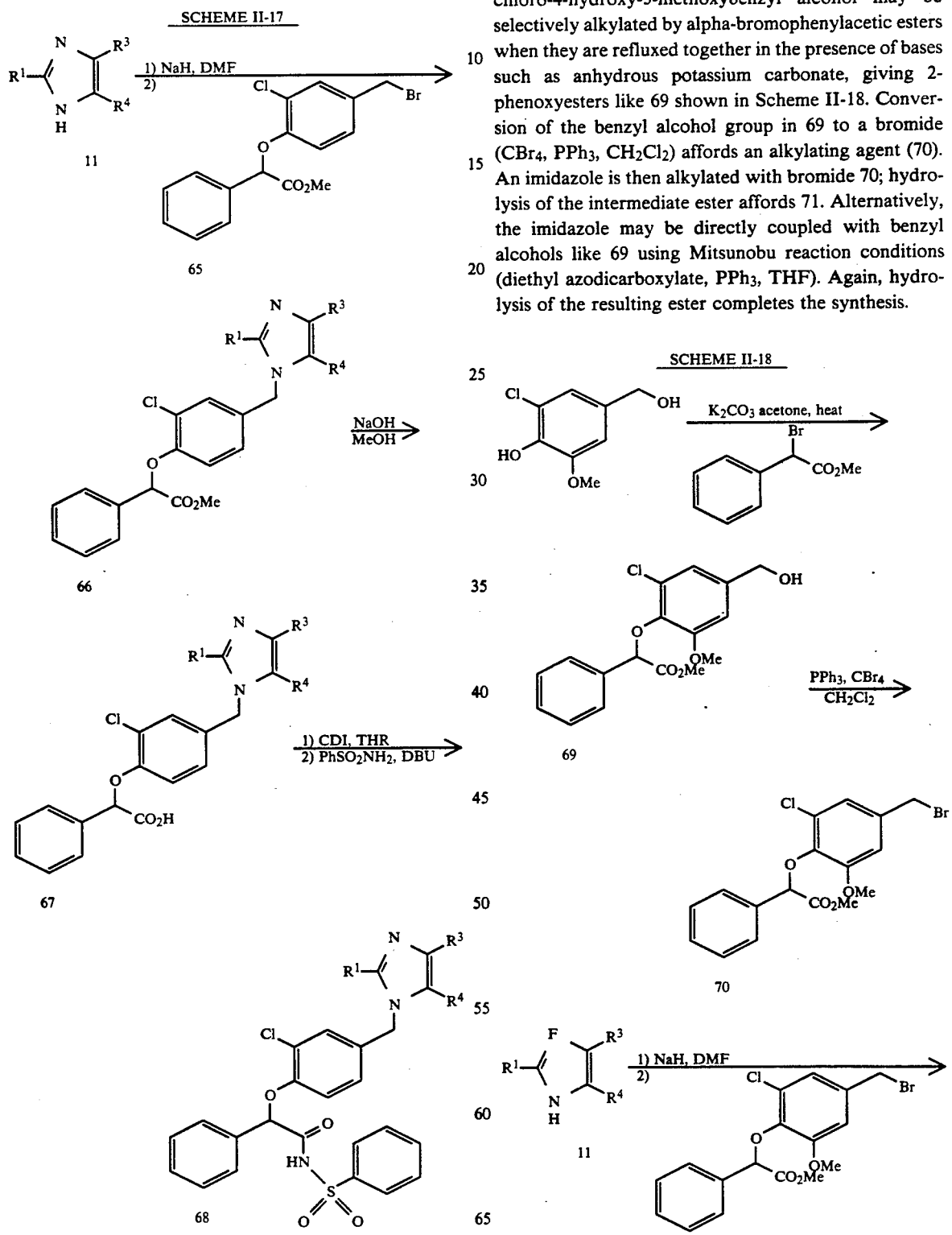

Precursors for the synthesis of AII Antagonists incorporating a substituted benzyl element wherein either

-continued
SCHEME II-18

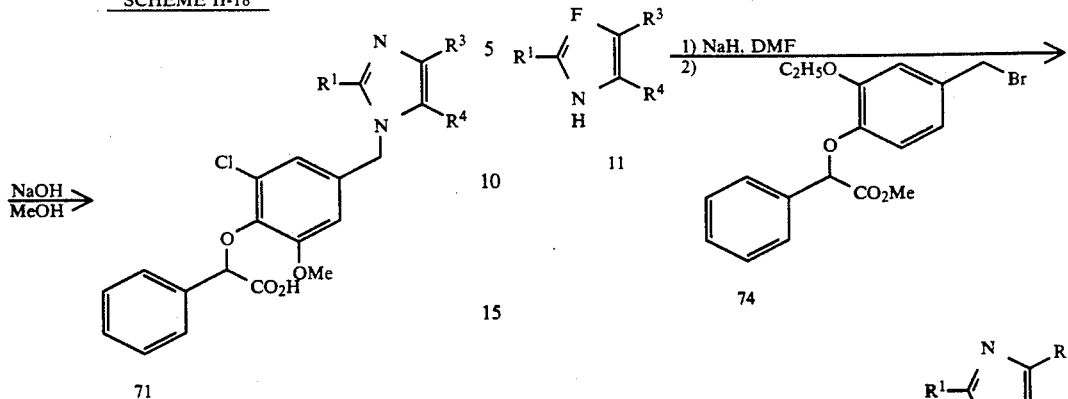

71

SCHEME II-19

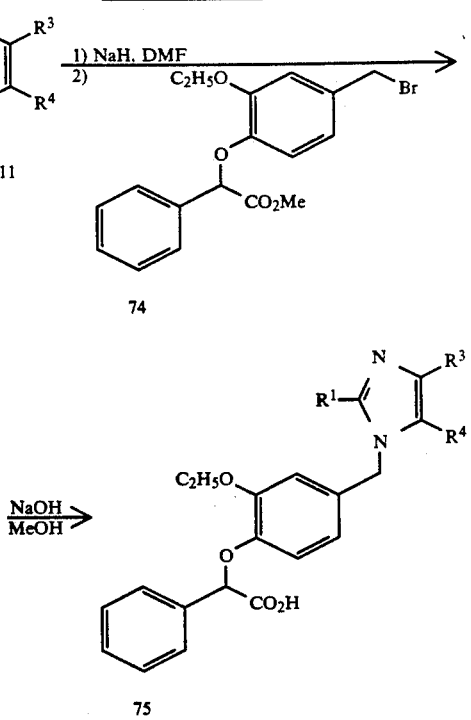

74

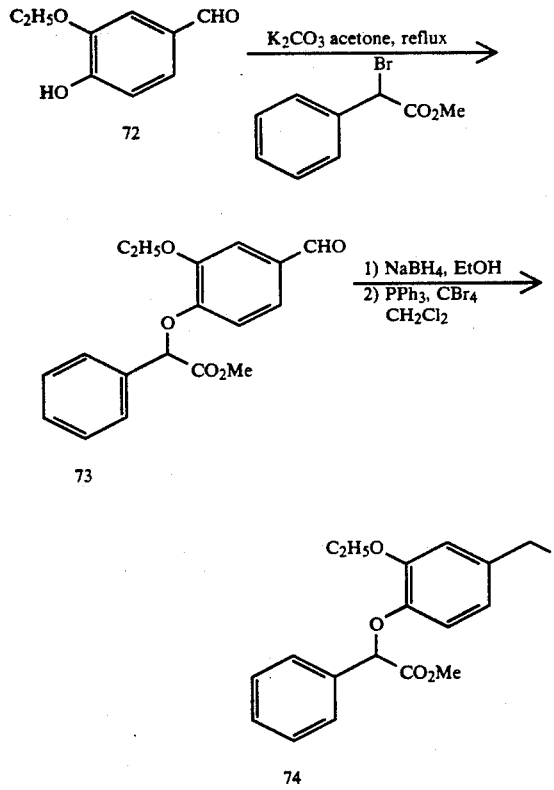

Scheme II-19 illustrates the use of commerically available 3-ethoxy-4-hydroxybenzaldehyde (72) to prepare an AII Antagonist of Formula I bearing a 3-ethoxy group ($R^9$) on the substituted benzyl element. Alkylation of the phenolic group of 72 with methyl 2-bromophenylacetate gives the aldehyde 73 which is then reduced to a benzyl alcohol with sodium borohydride in methanol or ethanol. The alcohol is converted to the bromide 74, and the synthesis of product 75 is completed as previously described.

75

Substituted 4-hydroxybenzoic esters are also convenient precursors for the synthesis of the substituted benzyl element defined in AII Antagonists of Formula I. In this approach, the phenolic hydroxyl group is usually first protected with a suitable protecting group, the ester is then reduced to a hydroxymethyl group, and deprotection affords a 4-hydroxybenzyl alcohol derivative. Scheme II-20 illustrates the preparation of derivative 80 using this sequence starting from methyl 3,5-dichloro-4-hydroxybenzoate (76). Silylation of phenol 76 followed in turn by lithium aluminum hydride reduction of the ester and silylether deprotection affords 3,5-dichloro-4-hydroxybenzyl alcohol (77). Phenol 77 was then selectively alkylated with methyl 2-bromophenylacetate, and the synthesis of derivative 80 was completed using the previously described methods.

SCHEME II-20

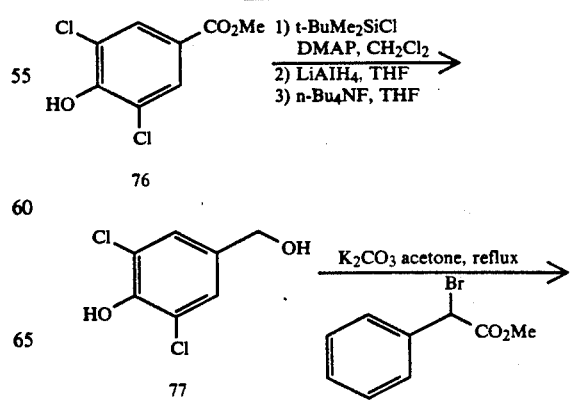

-continued
SCHEME II-20

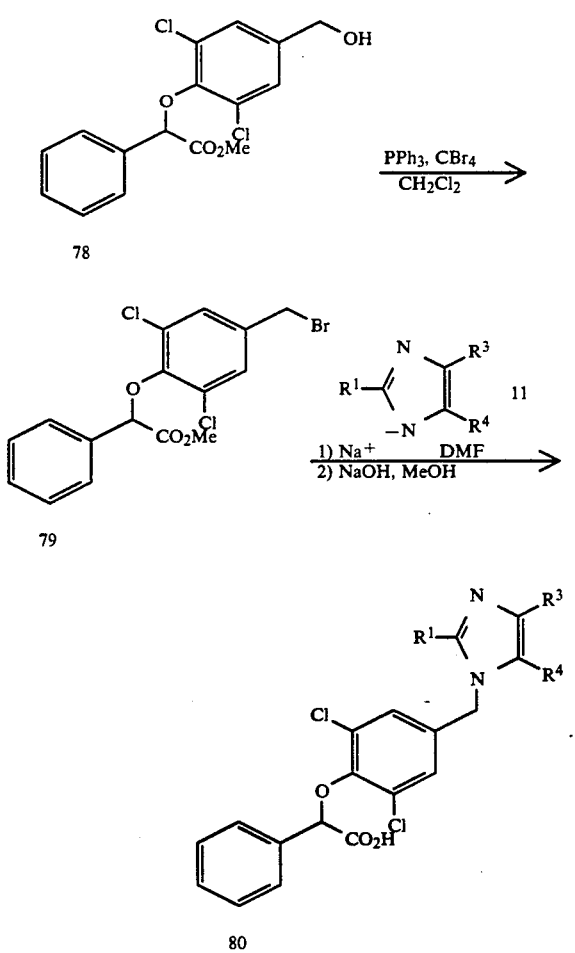

-continued
SCHEME II-21

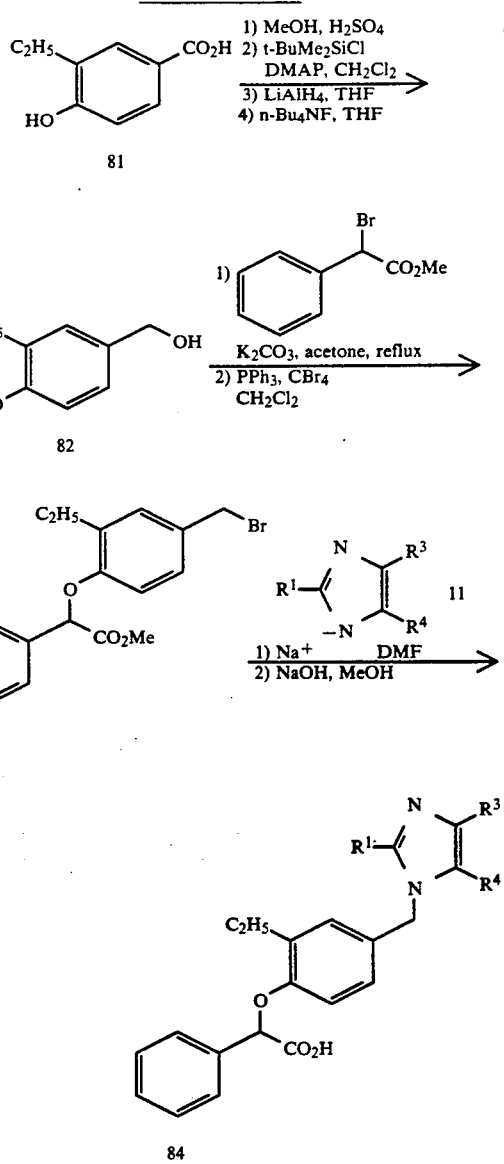

A variety of 2-substituted phenols are selectively carboxylated when refluxed with carbon tetrachloride, 50% aqueous sodium hydroxide and powdered copper (European Patent Application #193,853, Sep. 10, 1986) to afford the corresponding substituted 4-hydroxybenzoic acids. This reaction may be added to the synthetic sequence when it is convenient to derive the desired substituent on the benzyl portion of the target AII Antagonist from a readily available 2-substituted phenol. This strategy is illustrated for the preparation of derivative 84 shown in Scheme II-21. Carboxylation of 2-ethylphenol provides 3-ethyl-4-hydroxybenzoic acid (81). Acid 81 is then esterified, silylated, reduced and desilylated to give the 3-ethyl-4-hydroxybenzyl alcohol 82. Alcohol 82 may then be used to complete the synthesis of AII Antagonist 84 shown in Scheme II-21 using the previously discussed methodology.

SCHEME II-21

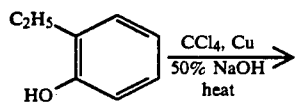

The Claisen rearrangement of phenyl-allylethers offers another useful technique for the introduction of alkyl substitutents ($R^9$ or $R^{10}$) at the meta position of the substituted benzyl element. In Scheme II-22, Claisen rearrangement at 185° C. of allyl ether 85 provides the allylphenol 86. Silylation of this phenol (86), followed by reduction of the ester group and bromination leads to the benzyl bromide 87. Alkylation of the imidazole 11, followed by silylether removal gives intermediates related to 88. Alkylation of 88 with methyl 2-bromophenylacetate followed by alkaline hydrolysis gives a derivative of Formula I (89) wherein $R^9$ is a meta-allyl group. Hydrogenation of intermediate 88 followed by the same sequence provides derivative 90 where $R^9$ is the meta-propyl group as shown in Scheme II-22.

SCHEME II-22

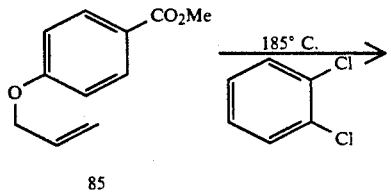
85

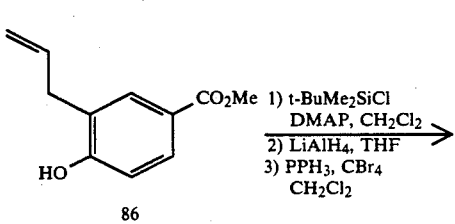
86

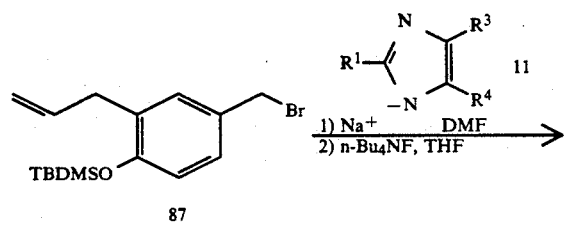
87

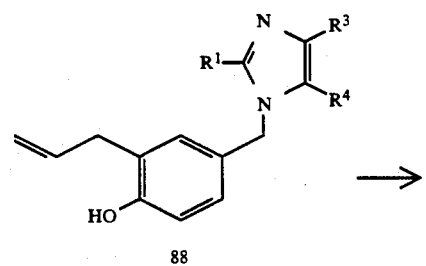
88

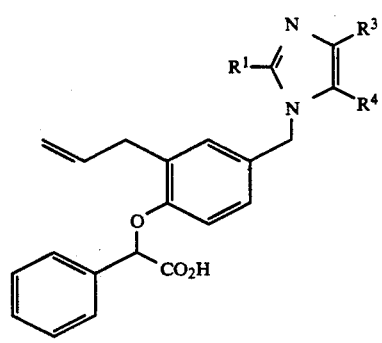
89

-continued
SCHEME II-22

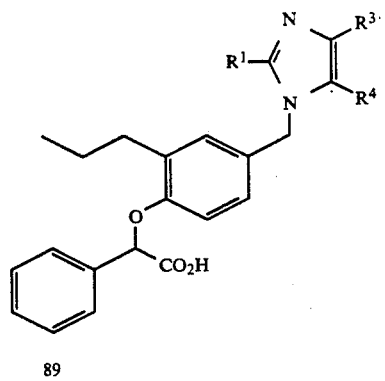
89

The Claisen rearrangement strategy for the introduction of a meta-alkyl substituent onto the substituted benzyl element of an AII Antagonist of Formula I may be exercised twice when it is desired that both $R^9$ and $R^{10}$ be meta-alkyl substituents. Thus, allyl phenol 86 may be converted to its O-allylether and subjected to a second Claisen rearrangement to provide the phenol (91) shown in Scheme II-23. Silylation of phenol 91, followed by catalytic hydrogenation and reduction of the ester group with lithium aluminum hydride gives the benzyl alcohol 92. A Mitsunobu reaction of the benzyl alcohol 92 with a heterocyle (11) described in Part I, followed by silylether deprotection gives an intermediate related to 93. The phenolic hydroxyl group of 93 may then be alkylated with a substituted alpha-bromoester and the ester hydrolyzed to yield the acid 94 in which $R^9$ and $R^{10}$ are meta-propyl groups as shown in Scheme II-23 and Example 52.

SCHEME II-23

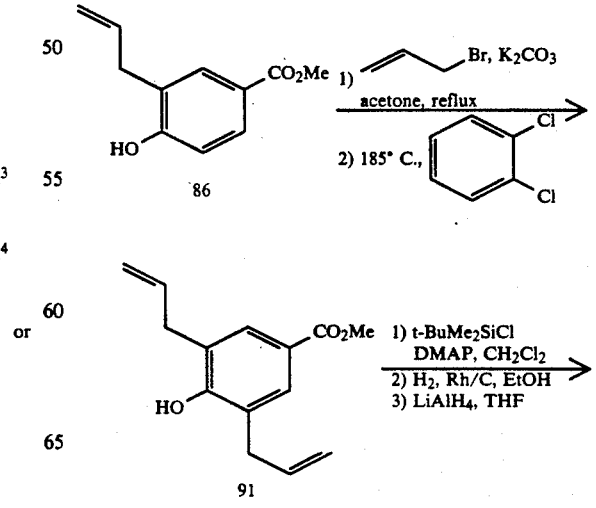
91

-continued
SCHEME II-23

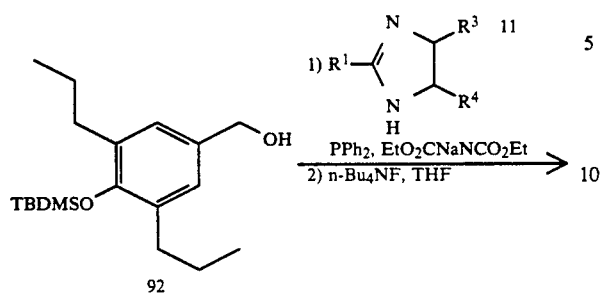

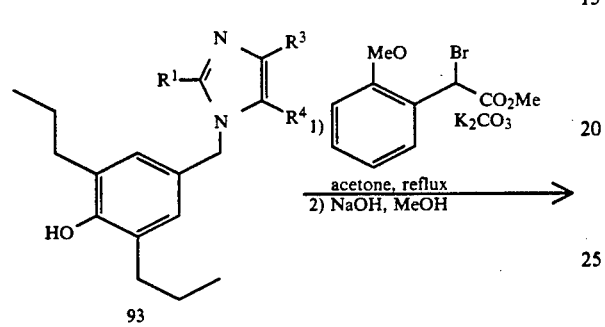

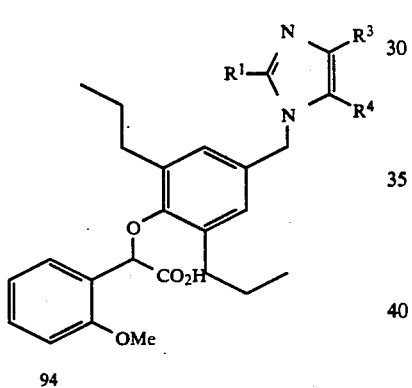

The synthesis of compounds of Formula I wherein: E=a single bond, $R^9$, $R^{10}$ and $R^{11}$ are H, Y=a single bond, Z=CO$_2$H $R^{12}$=phenyl, and X=NR$^{13}$, are presented in the following two Schemes. To access these analogs, an imidazole (ie. 11) defined in Part I is alkylated with p-nitrobenzyl bromide to yield nitro compounds such as 95 in Scheme II-24. Catalytic hydrogenation of the nitro group provides an aniline derivative (96) which is then alkylated by an alpha-bromoester. The ester 97 is subsequently hydrolyzed to afford a derivative of Formula I (98) where X=NH.

SCHEME II-24

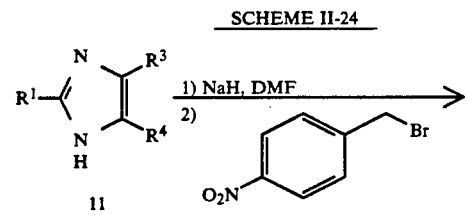

-continued
SCHEME II-24

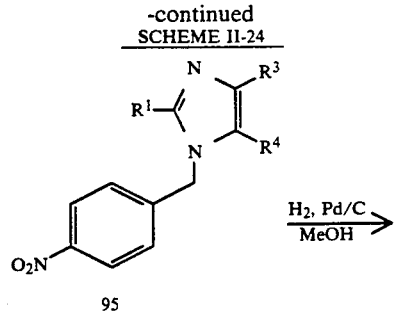

The preparation of AII Antagonists of Formula I similar to 98 in Scheme II-24 but having X=NR may be accomplished by methodology shown in Scheme II-25. The substituted aniline (96) presented above, is readily converted to the N-tert-butylcarbamate (BOC) 99. Carbamates such as 99 may be deprotonated at the amide nitrogen atom when reacted with bases such as sodium hydride in DMF, and then reacted with an alkyl halide. Subsequent treatment of the intermediate with trifluoroacetic acid removes the BOC group providing the mono-alkylated aniline derivative 100. The aniline nitrogen in 100 may be deprotonated again with sodium hydride in DMF and alkylated a second time with a substituted alpha-bromoester to provide esters such as afford the targeted AII Antagonists (102) of Formula I where X=NR.

SCHEME II-25

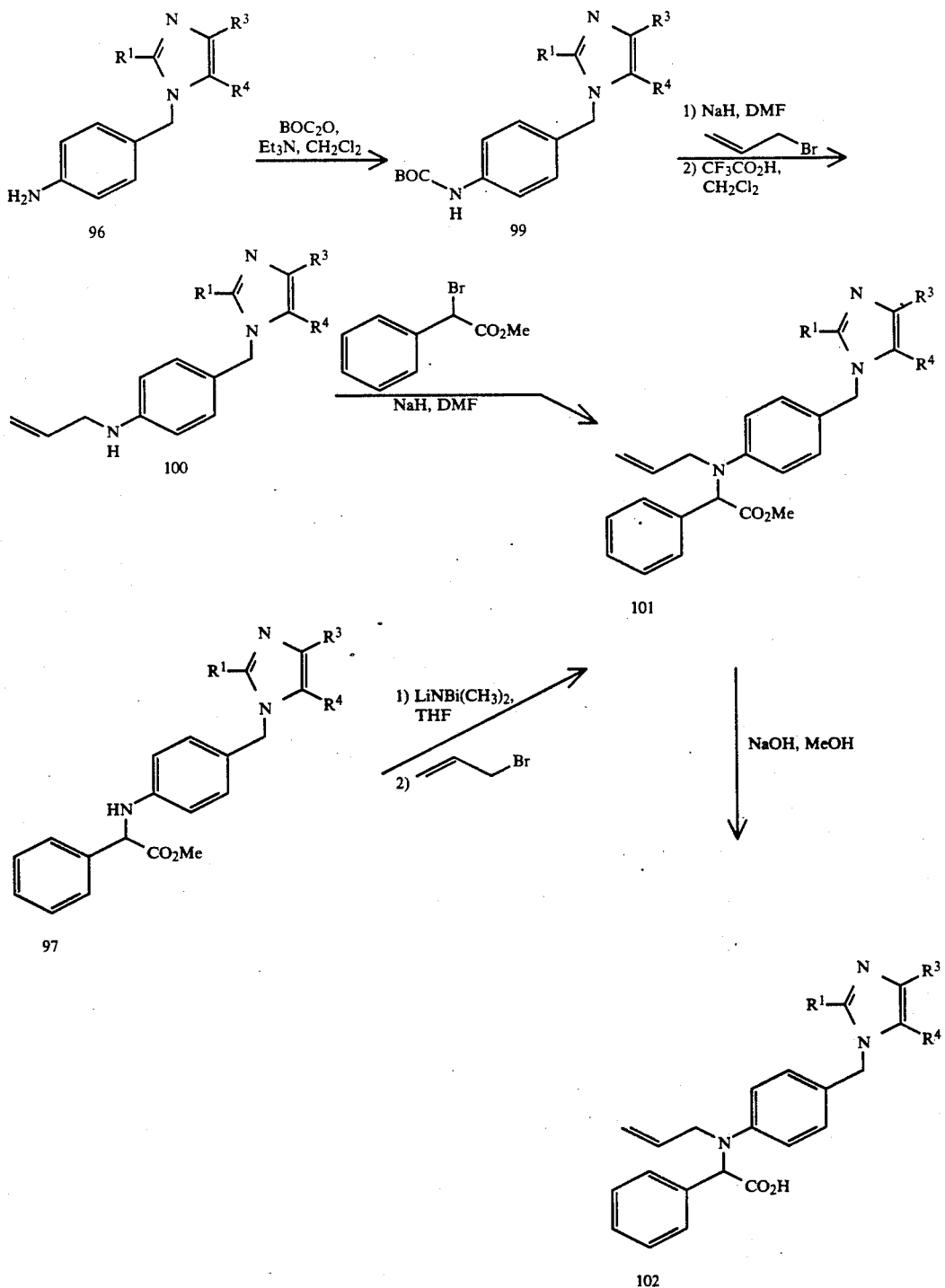

101. Alternatively, the order of introduction of the substituents on the nitrogen atom may be reversed. Intermediate 97 (Scheme II-24) may also be deprotonated by strong bases such as lithium bis(trimethylsilyl)amide in THF and then reacted with an alkyl halide to yield similar products (101). Ester 101 prepared by either synthetic route, is then hydrolyzed to Scheme II-26 describes the preparation of the intermediate aldehyde 104. The synthetic routes to 2,4,5-trisubstituted imidazoles are described in DuPont applications (EPO 0324377 and 0253310) and Merck application EPO 0401030 and are hereby incorporated by reference. The imidazole substituents are suitably protected as exemplified by the use of the t-butyldimethylsilyl group. The deprotonation of the protected imidazole with sodium hydride and alkylation of the salt with the appropriate methyl 4-bromomethylbenzoate gives the tetrasubstituted imidazole 103. An alkyl metal hydride reduction gives the benzylalcohol which undergoes a Swern oxidation to aldehyde 104.
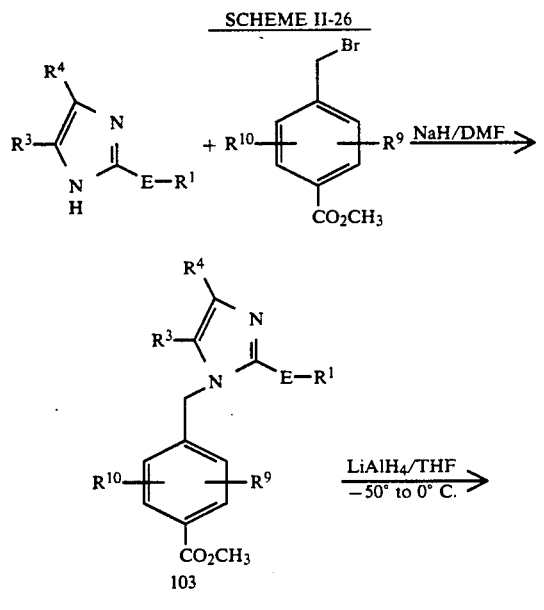
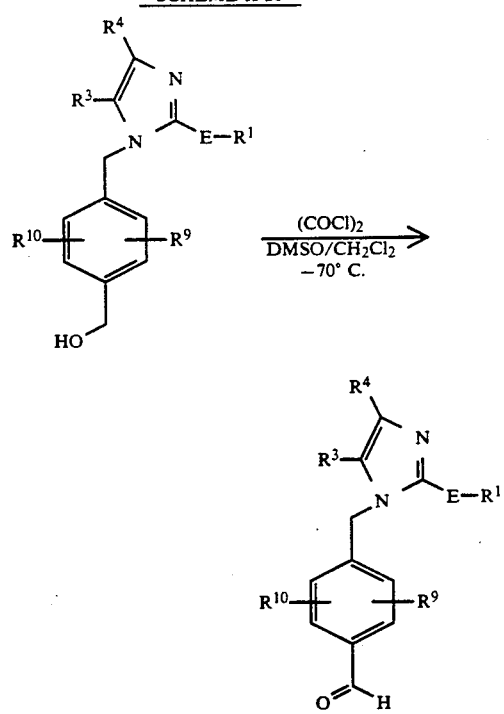
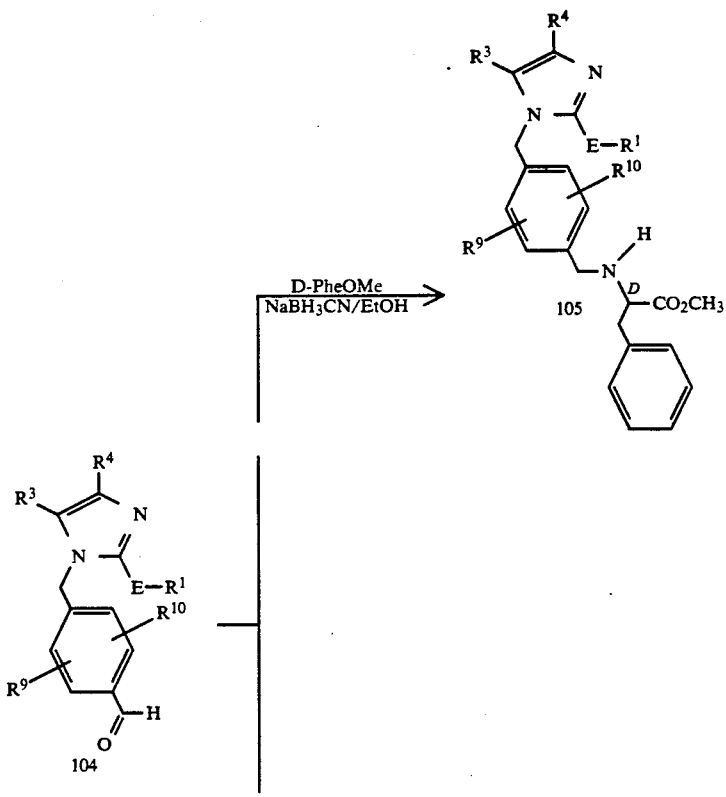

SCHEME II-27

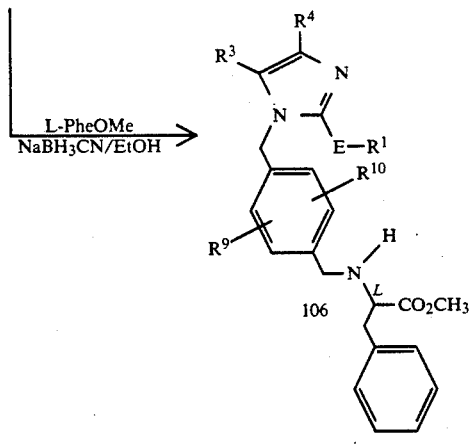

R[1] is n-butyl
E is a single bond
R[3] is CH$_2$O-TBDMS
R[4] is Cl
R[9] and R[10] are hydrogen
TBDMS is a t-butyldimethylsilyl group Scheme II-27 describes the reductive amination of the aldehyde with both the D- and L-phenylalanine methyl ester to give adducts 105 and 106 respectively. Further elaboration of adduct 105 by acylation with valeroyl chloride, dihydrocinnamoyl chloride and phenylacetyl chloride is described in Scheme II-28. The acylation of adduct 105 with valeroyl chloride is also shown. The amides formed were desilylated and hydrolyzed to the acids.

SCHEME II-28

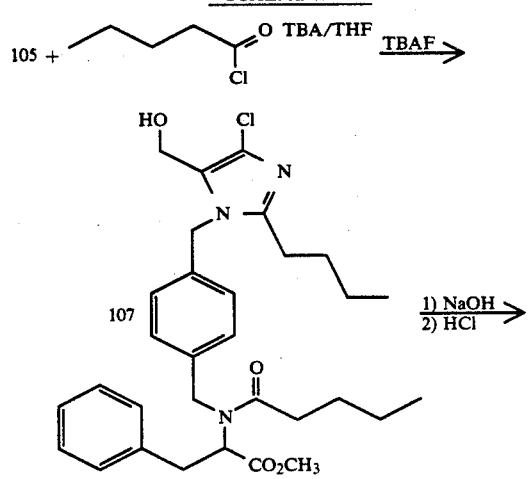

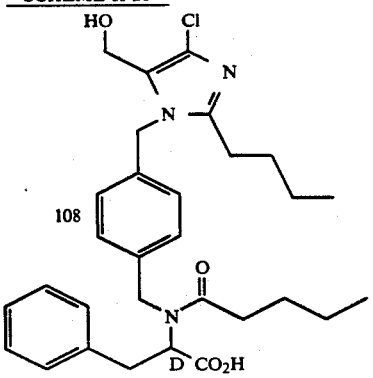

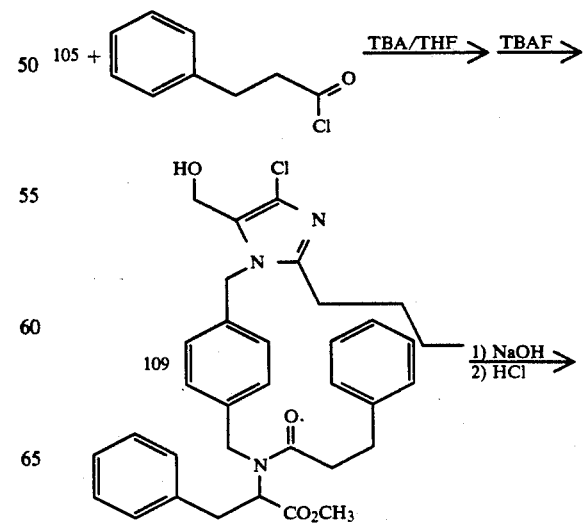

-continued
SCHEME II-28

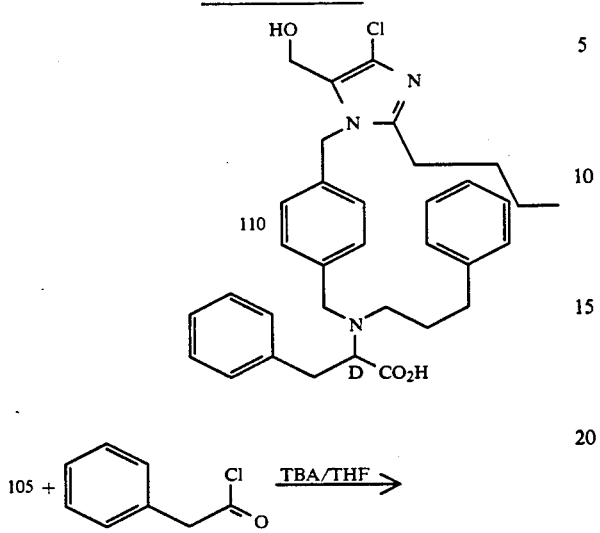

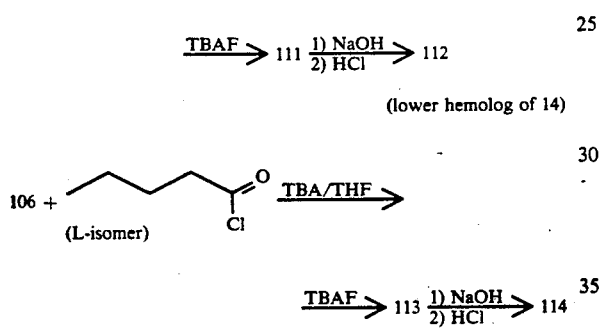

(lower hemolog of 14)

The synthesis of the benzylphenylalanine methyl ester is described in Scheme II-29. The imine is formed by treating phenylalanine methyl ester with benzaldehyde followed by deprotonation with lithium hexamethyldisilazide to generate the anion and alkylation with benzylbromide to give 1-benzylphenylalanine methyl ester 115.

SCHEME II-29

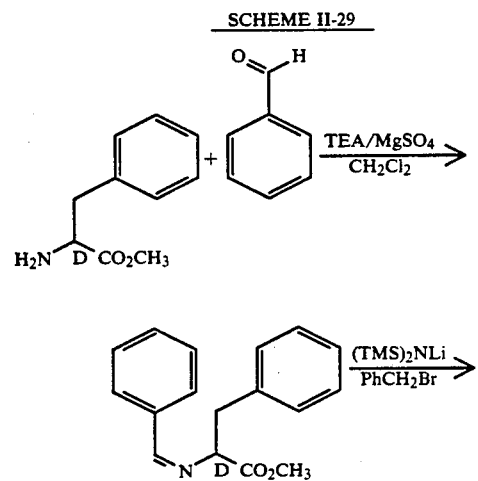

-continued
SCHEME II-29

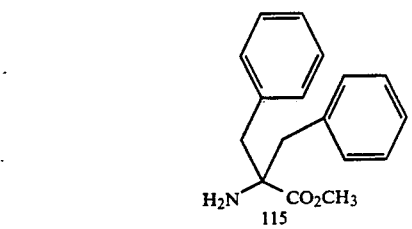

Scheme II-30 describes the reductive amination of the aldehyde 104 with the amino acid 115 using sodium cyanoborohydride in ethanol. The adduct formed compound 116 was desilylated using tetrabutylammonium fluoride and hydrolyzed to the acid with base to give the free acid 118.

SCHEME II-30

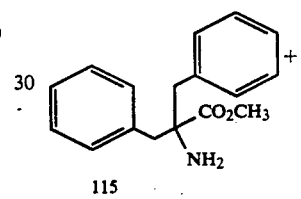

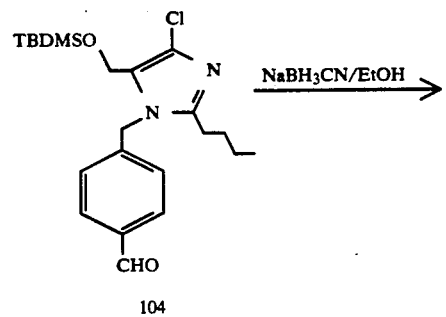

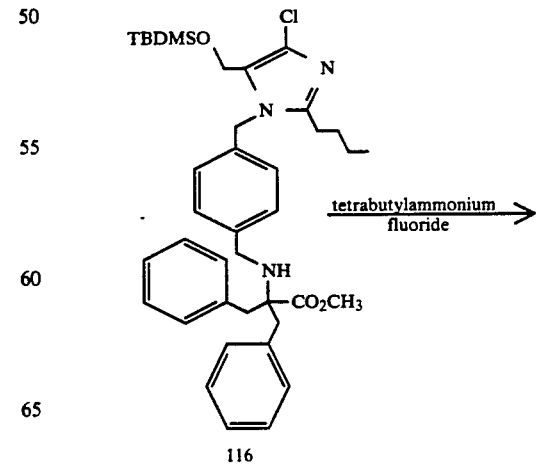

SCHEME II-30

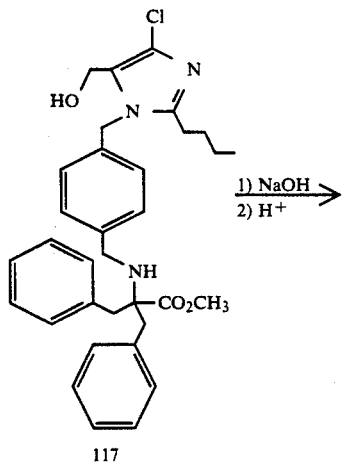

117

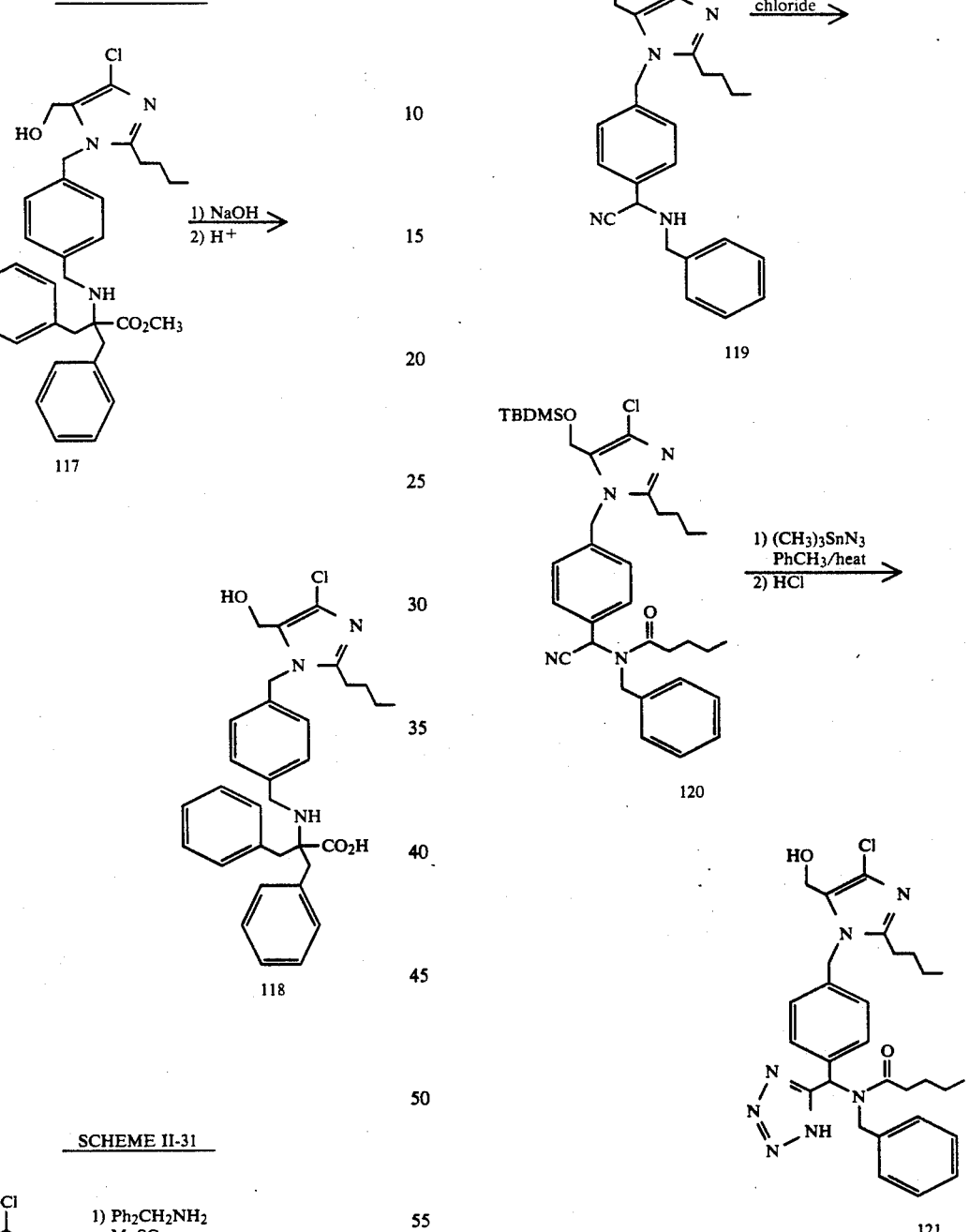

118

SCHEME II-31

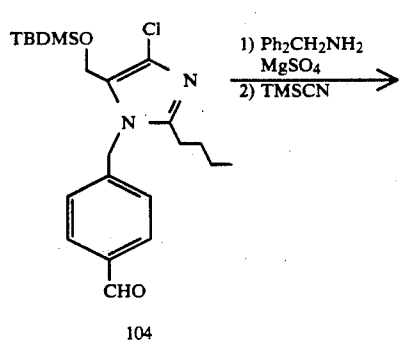

104

-continued
SCHEME II-31

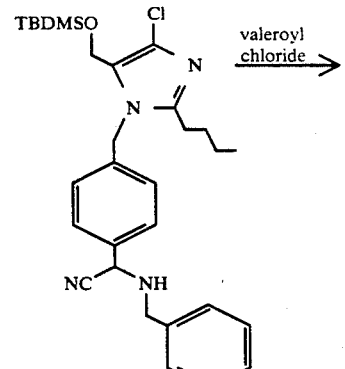

119

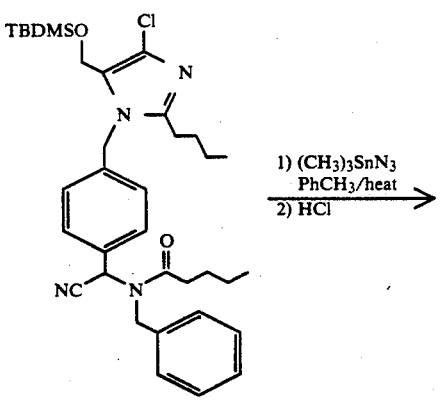

120

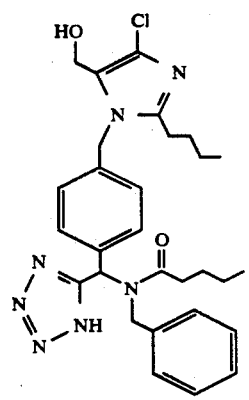

121

The synthesis of a tetrazole containing hybrid described in Scheme II-31 was accomplished using the intermediate aldehyde 104. The imine is formed with benzylamine and addition of trimethyl silyl cyanide to give the cyano-benzylamine adduct 119. Acylation of 119 with valeroyl chloride to give the amide 120. A 1,3-dipolar addition of trimethylstannyl azide to the cyano group followed by the treatment with HCl gives the tetrazole adduct 121.

SCHEME II-32

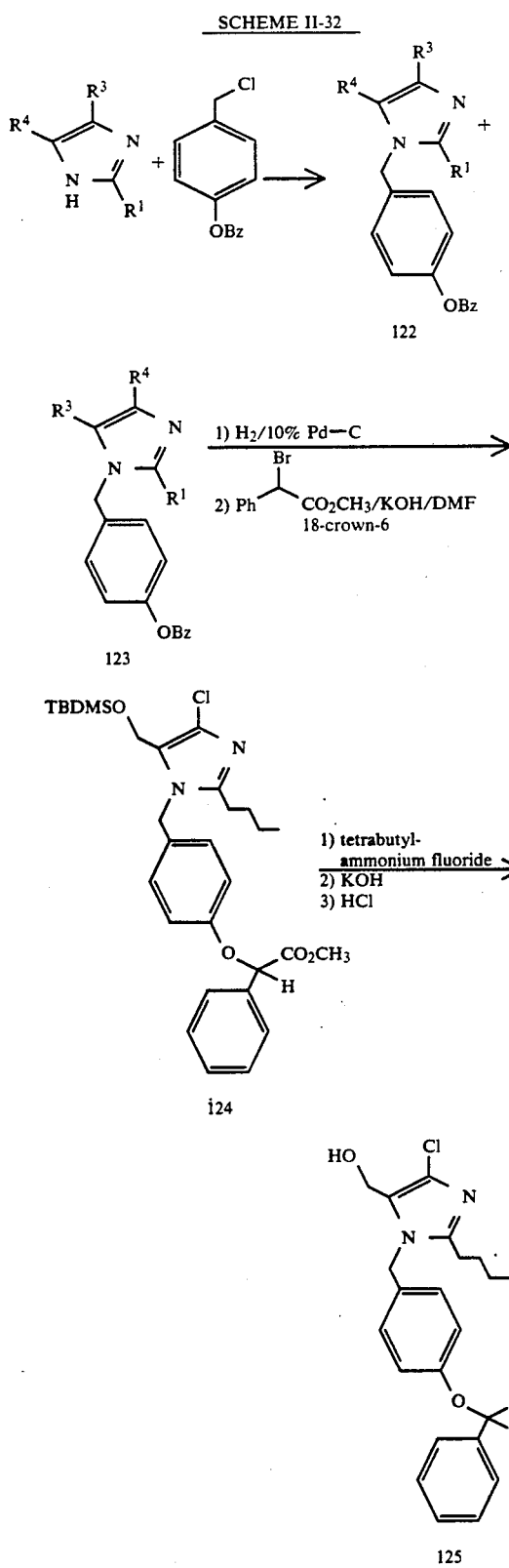

imidazole was hydrogenolyzed to the free hydroxyl, which is deprotonated and alkylated with methyl 2-bromo-2-phenylacetate to give the ether 124. The silyl ether was removed with fluoride and hydrolysis of the ester group with base and protonation of the salt with acid to give the desired inhibitor compound 125.

SCHEME II-33

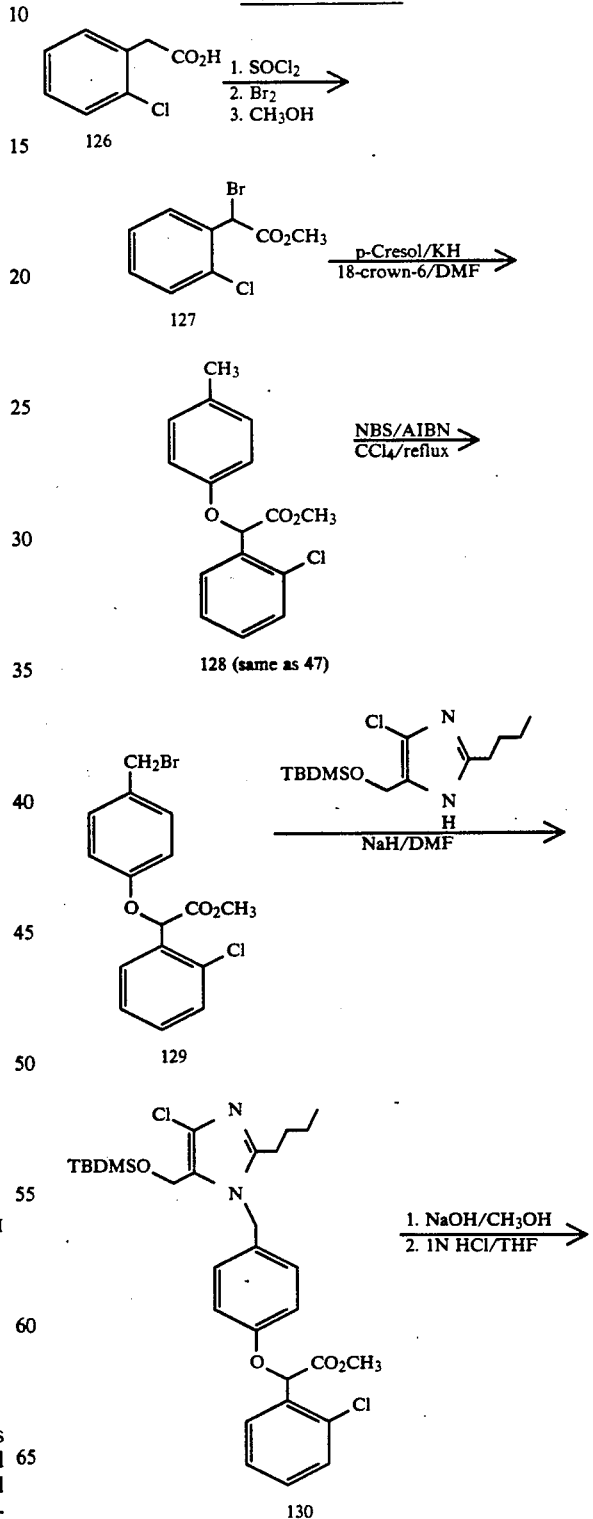

The synthesis of a substituted benzyl phenyl ester is described in Scheme II-32. The protected substituted imidazole was deprotonated with NaH and alkylated with 4-benzyloxybenzyl chloride to give the 1-substituted and 3-substituted imidazole. The 3-substituted -continued
SCHEME II-33

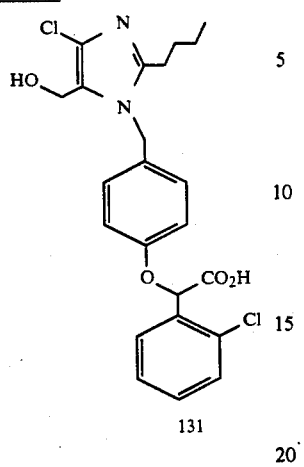

131

The o-chloro analog was prepared using similar synthetic procedures and is shown in Scheme II-33. The order of those steps were altered. The substituted phenyl benzyl ether was prepared first and then used to alkylate the substituted imidazole. 2-[1-(2-chlorophenyl)] acetic acid 126 was treated with thionyl chloride to generate the acid chloride, bromination to prepare the 2-bromo 2-[1-2-chlorophenyl]acetylchloride and esterification with methanol to generate methyl 2-bromo-2[1-(2'-chlorophenyl)]acetate 128. Deprotonation of p-cresol and alkylation with the bromide 127 gave the phenyl benzyl ether 127. The bromination of 128 gave the benzylbromide 129. The deprotonation of the imidazole and alkylation with 129 gives the protected inhibitor 130. Hydrolysis of 130 with base is KOH and acidification with HCl gives the desired inhibitor 131.

Scheme II-34 describes the preparation of the benzophenone derivative 137. 4-Methylbenzophenone 132 is halogenated with N-bromosuccinimide and a catalytic amount of AIBN to give the 4-bromomethyl derivative 133. Deprotonation of the imidazole with sodium hydride in DMF alkylation with the bromide 133 gives the imidazole substituted benzophenone 134. Treatment of 134 with trimethylsilylcyanide and potassium cyanide in methylene chloride with a catalytic amount of 18-crown-6 gives the cyano silyloxy adduct 135. The cyano group undergoes a 1,3- dipolar cycloaddition of the azide to give the methylene substituted with tertiary alcohol and tetrazole 136. The deprotection of the t-butyldimethylsilyoxy group with 6N HCl in THF to give the compound 137.

SCHEME II-34

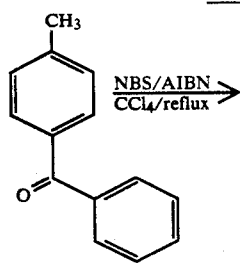

132

-continued
SCHEME II-34

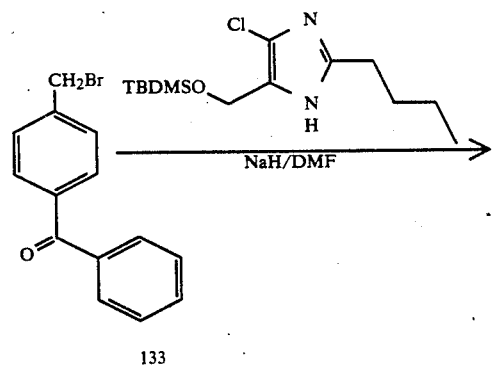

133

134

135

-continued
SCHEME II-34
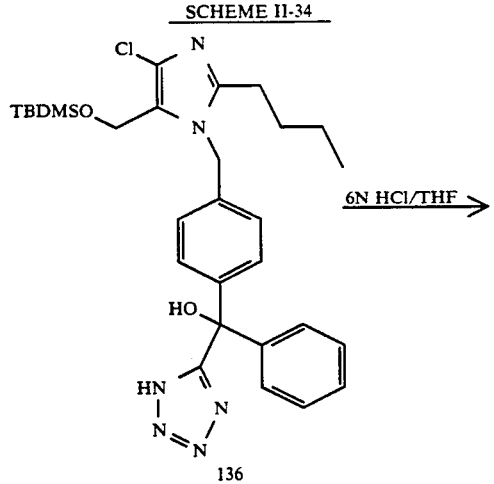
-continued
SCHEME II-35
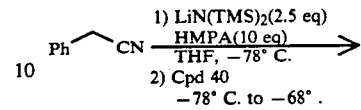
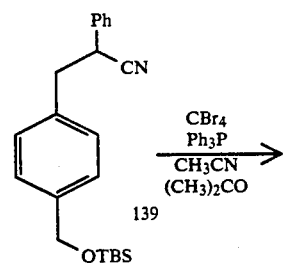
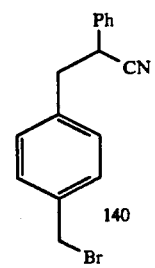
SCHEME II-35
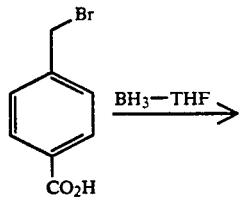
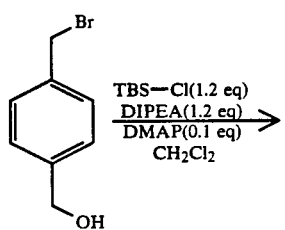
SCHEME II-36
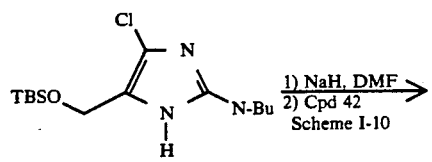
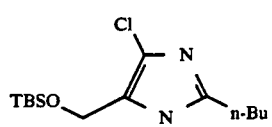
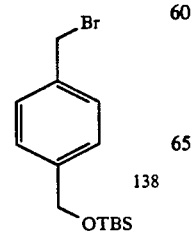
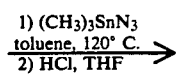

-continued
SCHEME II-36

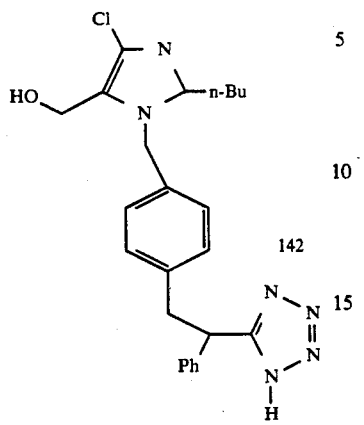

142

Compounds of Formula I where Z is —CONHSO$_2$R$^{20}$ (where R$^{20}$ is alkyl, aryl, or heteroaryl) may be prepared from the corresponding carboxylic acid derivatives of Formula I can be converted into the corresponding acid chloride by treatment with refluxing thionyl chloride or preferably with oxalyl chloride and a catalytic amount of dimethylformamide at low temperature (A. W. Burgstahler, L. O. Weigel, and C. G. Shaefer, *Synthesis*, 767, (1976)). The acid chloride then can be treated with the alkali metal salt of R$^{20}$SO$_2$NH$_2$ to form the desired acylsulfonamide 143. Alternatively, these acylsulfonamides may be also prepared from the carboxylic acids using N,N-diphenylcarbamoyl anhydride intermediates (F. J. Brown, et. al., *European Patent Application*, EP 199,543, K. L. Shepard and W. Halczenko, *J. Het. Chem.*, 16, 321 (1979). Preferably the carboxylic acids can be converted into acylimidazole intermediates, which then can be treated with an appropriate aryl or alkylsulfonamide and diazabicycloundecane (DBU) to give the desired acylsulfonamide 45 (J. T. Drummond and G. Johnson, *Tetrahedron Lett.*, 29, 1653 (1988)).

SCHEME II-37

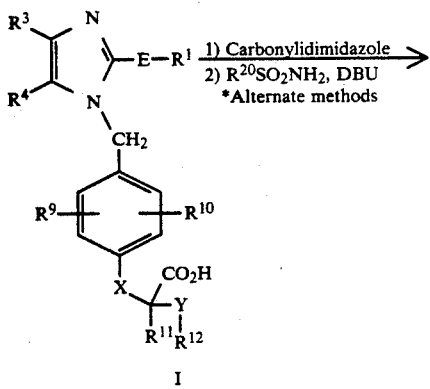

I

-continued
SCHEME II-37

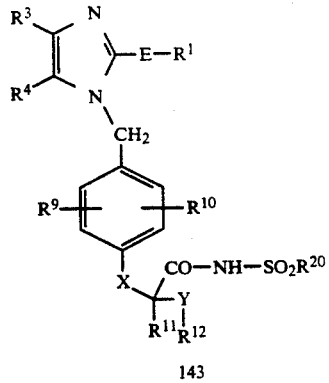

143

*Alternate Mehtods:
a) (i) SOCl$_2$, reflux (ii) R$^{20}$SO$_2$NH$^-$M$^+$ (where M is Na or Li)
b) (i) (COCl)$_2$, DMF, −20 °C.; (ii) R$^{20}$SO$_2$NH$^-$M$^+$
c) (i) N—(N,N-Diphenylcarbamoyl)pyridinium chloride, aq. NaOH; (ii) R$^{20}$SO$_2$NH$^-$M$^+$ It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306-326), H. Ferres, *Drugs of Today*, Vol. 19, 499-538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antagonists.

Using the methodology described above, representative compounds of the invention were evaluated and were found to exhibit an activity of at least IC$_{50}$<50 mM thereby demostrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

CONGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), level presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended hereto.

EXAMPLE 1

2-Butyl-1-[4-(N-(1(R)-carbomethoxy-1-benzyl)methyl)aminomethylphenyl]methyl-4-chloro-5-hydroxymethylimidazole (Scheme II-2, Compound 3)

Step A: Preparation of Methyl 4-(bromomethyl)benzoate

To a solution of 1.0 eq of 4-(bromomethyl)benzoic acid in 20 ml of methanol and 50 ml of toluene; was added dropwise 2.05 eq of trimethylsilyldiazomethane while stirring at room temperature. The reaction was titrated until a persistant pale yellow color existed from the addition of excess trimethylsilyldiazomethane. Let stir at room temperature for 1 hr to insure the complete evolution of $N_2$. Thin layer chromatography in 1:1 hexane:ethyl acetate indicated the disappearance of starting material and the appearance of desired ester with an Rf of 0.7.

FAB-MS M+H=230, 228.

$^1$H NMR (300 mHz, CDCl$_3$, ppm) δ8.02 (d, 2H); 7.46 (d, 2H); 4.50 (s, 2H); 3.93 (s, 3H).

Step B: Preparation of 2-Butyl-5-t-butyldimethylsilyloxymethyl-1-(4-carbomethoxyphenyl) methyl-4-chloroimidazole To a suspension of 1.2 eq NaH in 5 ml DMF was added dropwise a solution of the product of Example 1, Step A (2.0 g, 6.57 mmol) at 0° C. causing immediate reaction, as evidenced by the evolution of H$_2$ gas. The reaction mixture turned pale yellow and was stirred at 0° C. until the gas evolution ceased. At 0° C., 1.1 eq of methyl 4-(bromomethyl)benzoate was added, the reaction was warmed to room temperature and followed by TLC in 4:1 hexane: ethyl acetate. After 2.5 hours, the reaction appeared to be complete. The DMF was removed in vacuo and the residue dissolved in 100 ml ethyl acetate and washed with 0.5N citric acid (the aqueous wash was back washed with saturated NaHCO$_3$ solution) and brine, dried over MgSO$_4$, filtered and removed the solvent. The viscous yellow oil which was isolated (3.12 g) contained two spots. The crude material was dissolved in CH$_2$Cl$_2$, treated with 0.5 eq of dimethylaminopyridine (DMAP), cooled to 0° C. under N$_2$ and then 0.33 eq t-butyldimethylsilyl chloride (0.33 g) was added. When the suspension dissolved, the solution was warmed to room temperature and stirred for 2 hours. The CH$_2$Cl$_2$ was evaporated off and the residue, a slush, was dissolved in ethyl acetate and the DMAP.HCl was filtered off. Some DMAP.HCl remained and was removed by filtering through a silica plug. The residue was chromatographed on a silica gel column using a medium pressure liquid chromatography (MPLC) setup, eluting with a 4:1 hexane: ethyl acetate, Isomer a, 2-butyl-5-t-butyldimethylsilyloxymethyl-1-(4-carbomethoxyphenyl)methyl-4-chloroimidazole isolated in 80% yield (2.34 g) and isomer b, 2-butyl-4-t-butyl-dimethylsilyloxymethyl-1-(4-carbomethoxyphenyl)methyl-5-chloroimidazole, isolated in 12.8% yield (0.38 g).

FAB-MS: isomer a M+1=451; isomer b M+1=451.

$^1$H NMR isomer a: (300 mHz, CDCl$_3$, ppm) δ8.00 (d, 2H); 7.06 (d, 2H); 5.25 (s, 2H); 4.50 (s, 2H); 3.90 (s, 3H); 2.50 (t, 2H); 1.70-1.55 (m, 2H); 1.37-1.23 (m, 2H); 0.8-0.76 (m, 12H); 0.02 (s, 6H). isomer b: (300 mHz, CDCl$_3$, ppm) δ8.00 (d, 2H); 7.08 (d, 2H); 5.14 (s, 2H); 4.65 (s, 2H); 3.90 (s, 3H); 2.55 (t, 2H); 1.68-1.55 (m, 2H); 1.32 (m, 2H); 0.92 (s, 9H); 0.85 (t, 3H); 0.10 (s, 6H).

Step C: Preparation of 2-Butyl-5-t-butyldimethylsilyloxymethyl-4-chloro-1-(4-hydroxyphenyl)methyl imidazole The product of Example 1, Step B, isomer a (2.22 g, 4.93 mmol) was dissolved in ethyl acetate, dried over MgSO$_4$, filtered and the solvent evaporated in vacuo. To a 35 ml dry THF solution of isomer a, a pale yellow oil, cooled under N$_2$ to −50° C., was added dropwise 1.2 eq of a 1.0M THF solution of LiAlH$_4$. The reaction was allowed to warm to −25° C. After 30 minutes, 243 μl of H$_2$O was added dropwise at −25° C. causing H$_2$ evolution and was followed by the addition of 243 μl 15% NaOH and 243 μl H$_2$O, gradually warming to room temperature. The reaction was continually stirred until the gelatinous precipitate became granular. The solid aluminum salts were removed by filtration rinsing with THF. The filtrate was dried over MgSO$_4$, filtered, and stripped of solvent to give a colorless oil in 100% yield (2.11 g).

FAB-MS: M+H=423.

$^1$H NMR: (300 mHz, CDCl$_3$, ppm) δ7.33 (d, 2H); 7.00 (d, 2H); 5.20 (s, 2H); 4.68 (d, 2H); 4.50 (s, 2H); 2.50 (t, 2H); 1.70-1.55 (m, 3H); 1.30 (m, 2H); 0.90-0.72 (m, 12H); 0.02 (s, 6H).

Step D: Preparation of 2-Butyl-5-t-butyldimethylsilyloxymethyl-1-(4-carboxaldehydophenyl)methyl-4-chloroimidazole To a solution of 636 μl of oxalyl chloride in 30 ml of dichloromethane (CH$_2$Cl$_2$), cooled to −78° C., was added dropwise a solution of 1.03 ml dimethylsulfoxide in 5.0 ml CH$_2$Cl$_2$. After 15 minutes at −70° C., a solution of the product of Example 1, Step C (2.2 g, 5.21 mmol) in 30 ml of CH$_2$Cl$_2$ was added dropwise. After stirring at −70° C. for 45 min, 3.19 ml of triethylamine was added, and the reaction was warmed to room temperature. The reaction was diluted with 100 ml of H$_2$O, the layers separated and the organic layer was washed with H$_2$O and brine, and dried over MgSO$_4$. Removal of solvent in vacuo gave a viscous pale yellow oil, which became a crystalline solid when refrigerated. The desired aldehyde had an R$_f$ of 0.35 in 3:2 hexane:ethyl acetate.

FAB-MS: M+1 of 421.

$^1$H NMR: (300 mHz, CDCl$_3$, ppm) δ10.0 (s, 1H+); 7.85 (d, 2H); 7.15 (d, 2H); 5.26 (s, 2H); 4.50 (s, 2H); 2.50 (t, 2H); 1.70-1.50 (m, 2H): 1.40-1.20 (m, 2H); 0.80-0.68 (m, 12H); 0.02 (s, 6H).

Step E: Preparation of 2-Butyl-5-t-butyldimethylsilyloxymethyl-1-[4-(N-(1(R)-carbomethoxy-1-benzyl)methyl)aminomethylphenyl]methyl-4-chloroimidazole To a solution of 1.1 eg of HCl.D-phenylalanine methyl ester (0.46 g, 2.11 mmol) in 10 ml of dry ethanol over 3 A powdered molecular sieves was added a solution of the product of Example 1, Step D (0.81 g, 1.92 mmol) in 10 ml ethanol. After stirring for 35 minutes, 3 eq of 1.0M NaBH$_3$CN in THF (5.8 ml, 5.77 mmol) was added, and the reaction stirred overnight at room temperature under N$_2$ atmosphere. The reaction solvent was removed in vacuo and the residue chromatographed on an LH-20 column eluting with CH₃OH. This failed to remove all the TEA.HCl and NaBH₃CN and was rechromatographed on a silica gel column eluting with 30% ethyl acetate in hexane. The product was isolated in 78% yield (0.88 g)

FAB-MS: M+1 at 584.

$^1$H NMR: (300 mHz, CDCl₃, ppm) δ7.35–7.1 (m, 7H); 5.15 (s, 2H), 4.50 (s, 2H); 3.80 (d, 1H); 3.65 (s, 3H); 3.60 (d, 1H); 3.50 (t, 1H); 2.95 (m, 2H) 2.50 (t, 2H); 1.70–1.55 (m, 2H); 1.40–1.22 (m, 2H); 0.95–0.80 (m, 12H); 0.02 (s, 6H).

Step F: Preparation of 2-Butyl-1-[4-(N-(1(R)-carbomethoxy-1-benzyl)methyl)aminomethylphenyl]-methyl-4-chloro-5-hydroxymethylimidazole (Scheme II-2. Compound 3)

To a solution of the product of Example 1, Step E (53 mg, 91 μmol) in 1.0 ml THF was added 0.11 ml of a 1.0M THF solution of tetrabutylammonium fluoride and the reaction was stirred overnight at room temperature under N₂. The reaction was then filtered through a silica gel plug eluting with ethyl acetate to remove the baseline tetrabutylammonium fluoride. The pale yellow oil was chromatographed on silica gel eluting with 3:2 hexane:ethyl acetate and the product was isolated in a 76% yield (32 mg).

FAB-MS: M+1 of 470.

$^1$H NMR: (300 mHz, CDCl₃, ppm) δ7.30–7.10 (m, 7H); 6.90 (d, 2H); 5.17 (s, 2H) 4.46 (s, 2H); 3.80 (d, 1H); 3.64 (s, 3H); 3.60 (d, 1H); 3.50 (t, 1H) 2.95 (m, 2H) 2.55 (t, 2H); 1.65 (m, 2H); 1.35 (m, 2H), 0.90 (t, 3H).

EXAMPLE 2

2-Butyl-1-[4-(N-(1(R)-carboxy-1-benzyl)methyl)aminomethylphenyl]methyl-4-chloro-5-hydroxymethylimidazole sodium salt To a solution of the product of Example 1, Step F (37 mg, 78 μmol) in 3:1 CH₃OH:H₂O was added 47 μl of 2.0N NaOH and the reaction was stirred at room temperature overnight. The solvent was removed in vacuo and the residue was dissolved in 1.5 ml CH₃OH filtered and chromatographed on a Sephadex column (LH-20) eluting with CH₃OH. Two overlapping peaks were observed which by mass spectrometry were found to be the sodium salt and the free acid, and were combined and isolated in a ~100% yield (35 mg).

FAB-MS: M+1 is 456 (free acid) and M+Na (Na salt).

$^1$H NMR: (300 mHz, CD₃OD, ppm) δ7.30–7.10 (m, 7H); 6.98 (d, 2H); 5.30 (s, 2H); 4.45 (s, 2H); 3.85–3.70 (m, 1H); 3.63–3.50 (m, 1H); 3.35 (m, 1H); 3.10–2.93 (m, 1H); 2.92–2.78 (m, 1H); 2.55 (t, 2H); 1.53 (m, 2H); 1.30 (m, 2H); 0.88 (t, 3H).

EXAMPLE 3

2-Butyl-1-[4-(N-(1(R)-carbomethoxy-1-benzyl)methyl-methyl-N-pentanoyl)aminomethylphenyl]-4-chloro-5-hydroxymethylimidazole Step A: Preparation of 2-Butyl-5-t-butyldimethylsilyloxymethyl-1-[4-(N-(1(R)-carbomethoxy-1-benzyl)-methyl-N-pentanoyl)aminomethylphenyl]-4-chloroimidazole To a 2.0 ml THF solution of the product of Example 1, Step E (0.12 g, 0.20 mmol) under N₂ was added 1.5 eq of TEA followed by the addition of 1.2 eq of valeroyl chloride, which resulted in the precipitation of TEA.HCl. The reaction was warmed, and when checked by TLC after 1 hr it was complete. The TEA.HCl was filtered from the reaction and the filtrate was evaporated down to give a yellow oil. The residue contained two spots which were presumed to be the silylated and unsilylated products. The residue was chromatographed on silica gel eluting with 30% ethyl acetate in hexane and the product isolated in 92% yield (124 mg).

FAB-MS: M+1 of 668.

$^1$H NMR: (300 mHz, CDCl₃, ppm) δ7.30–7.05); (m, 7H); 6.90 (d, 2H); 5.15 (s, 2H); 4.50 (s, 2H); 4.40 (d, 1H); 4.30 (m, 1H) 3.73 (d, 1H) 3.64 (s, 3H); 3.4–3.2 (m, 2H); 2.5 (t, 2H); 2.24 (m, 2H); 1.6 (m, 4H); 1.3 (m, 4H); 0.85 (m, 15H); 0.02 (s, 6H).

Step B: Preparation of 2-Butyl-1-[4-(N-(1(R)-carbomethoxy-1-benzyl)methyl)methyl-N-pentanoyl)aminomethylphenyl]-4-chloro-5-hydroxymethylimidazole To a solution of the product of Example 3, Step A (0.11 g, 0.16 mmol) in 2 ml THF under N₂ at room temperature was added 1.2 eq of a 1.0M solution of tetrabutylammonium fluoride and followed the procedure of Example 1, Step F. The product was isolated in a 73% yield (63 mg).

FAB-MS: M+1 at 554.

$^1$H NMR: (300 mHz, CDCl₃, ppm) δ7.30–7.02 (m, 7H); 6.90 (d, 2H); 5.15 (s, 2H); 4.44 (s, 2H); 4.48 (d, 1H); 4.26 (m, 1H); 3.74 (d, 1H); 3.63 (s, 3H); 3.4–3.17 (m, 2H); 2.50 (t, 2H); 2.2 (m, 2H); 1.6 (m, 4H), 1.28 (m, 4H); 0.85 (m, 6H)

EXAMPLE 4

2-Butyl-1-[4-(N-(1(R)-carboxy-1-benzyl)methyl-N-pentanoyl)aminomethylphenyl]methyl-4-chloro-5-hydroxym ethylimidazole sodium salt (Scheme II-3, Compound 11)

Following the procedure of Example 2, Step A the product of Example 3, Step B was hydrolyzed to give the sodium salt in 58% yield (24.5 mg).

FAB-MS: M+1 at 562 and M+Na at 584.

$^1$H NMR: (300 mHz, CD₃OD, ppm) 7.3–6.82 (m, 9H); 5.25 (d, 2H), 5.00 (d, 1H); 4.6 (m, 1H); 4.44 (s, 2H); 4.30 (d, 1H); 3.4–2.8 (m, 2H); 2.1 (m, 2H); 2.4–2 (m, 2H); 1.6–1.1 (m, 8H); 0.9–0.75 (m, 6H).

EXAMPLE 5

2-Butyl-1-[4-(N-(1(R)carbomethoxy-1-benzyl)methyl-N-(3-phenyl)propionyl)aminomethylphenyl]methyl-4-chloro-5-hydroxymethylimidazole (Scheme I-3, Compound 13)

Step A: Preparation of 2-Butyl-5-t-butyldimethylsilyloxymethyl-1-[4-(N-(1(R)-carbomethoxy-1-benzyl)-methyl-N-(3-phenyl)propionyl)aminomethylphenyl]-methyl-4-chloroimidazole Following the procedure of Example 3, Step A, the product of Example 1, Step E (0.11 g, 0.195 mmol) was treated with hydrocinnamoyl chloride and the product was isolated in a 78% yield (110 mg).

FAB-MS: M+1 at 716.

$^1$H NMR: (300 mHz, CDCl₃, ppm) δ7.30–6.8 (m, 14H); 5.13 (s, 2H); 4.48 (d, 2H); 4.35 (d, 1H); 4.27 (m, 1H); 3.7 (d, 1H); 3.62 (s, 3H); 3.4–3.1 (m, 2H); 2.93 (m, 2H+) 2.5 (m, 4H) 1.6 (m, 2H); 1.3 (m, 2H); 1.83 (m, 3H).

Step B: Preparation of 2-Butyl-1-[4-(N-(1(R)-carbomethoxy-1-benzyl)methyl-N-(3-phenyl)propionyl)aminomethylphenyl]methyl-4-chloroimidazole Following the procedure of Example 1, Step F and using the product of Example 5, Step A as the substrate, the desired product was isolated in a 61% yield (55 mg).

FAB-MS: M+1 at 602, M-18 at 584 (loss of $H_2O$) and M-188 at 414 (loss of imidazole fragment).

$^1$H NMR: (300 mHz, CDCl$_3$, ppm) δ7.30–6.8 (m, 14H); 5.15 (s, 2H); 4.43 (d, 2H); 4.32 (d, 1H); 4.27 (m, 1H); 3.7 (d, 1H); 3.62 (s, 3H); 3.4–3.1 (m, 2H); 2.93 (m, 2H+) 2.5 (m, 3H) 2.28 (m, 1H); 1.64 (m, 2H); 1.40 (m, 2H) 0.88 (t, 3H).

EXAMPLE 6

2-Butyl-1-[4-(N-(1(R)-carboxy-1-benzyl)methyl-N-(3-phenyl)propionyl)aminomethylphenyl]methyl-4-chloroimidazole Following the procedure of Example 2, Step A and using the product of Example 5, Step B in two products of slightly different R$_f$s resulted which were combined and treated with HCl in THF to obtain the free acid/HCl salt.

FAB-MS: M+1 at 588 and M-18 at 570.

$^1$H NMR: (300 mHz, CD$_3$OD, ppm) δ7.3–7.0 (m, 14H); 5.5 (s, 2H); 4.53 (s, 2H); 4.45–4.3 (m, 2H); 3.9 (d, 1H); 3.25–3.1 (m, 1H); 2.95–2.75 (m, 4H); 2.7–2.4 (m, 2H); 1.6–1.4 (m, 2H); 1.38–1.2 (m, 2H) 0.92–0.78 (m, 3H).

EXAMPLE 7

2-Butyl-1-[4-(N-(1(R)-carbomethoxy-1-benzyl)methyl-N-phenylacetyl)aminomethylphenyl]methyl-4-chloro-5-hydroxymethylimidazole- Step A: 2-Butyl-5-t-butyldimethylsilyloxymethyl-1-[4-(N-(1(R)-carbomethoxy-1-benzyl)methyl-N-(phenylacetyl)aminomethylphenyl]methyl-4-chloroimidazole Following the procedure of Example 3, Step A the product of Example 1, Step E (0.12 g, 0.209 mmol) was treated with phenylacetyl chloride and the product was isolated in a 57% yield (60 mg) based on recovered starting material.

FAB-MS: M+1 at 702.

$^1$H NMR: (300 mHz, CDCl$_3$, ppm) δ7.38–7.15 (m, 9H); 7.0–6.95 (m, 5H); 5.15 (s, 2H); 4.48 (s, 2H); 4.44 (d, 1H); 4.15 (m, 1H); 3.67 (s, 3H); 3.63 (s, 2H); 3.60 (d, 1H); 3.38–3.13 (m, 2H); 2.5 (t, 2H); 1.6 (m, 2H); 1.3 (m, 2H); 0.85 (m, 12H); 0.02 (s, 6H).

Step B: Preparation of 2-Butyl-1-[4-N-(1(R)-carbomethoxy-1-benzyl)methyl-N-(phenylacetyl)aminomethylphenyl]methyl-4-chloro-5-hydroxymethylimidazole Following the procedure of Example 1, Step F and using the product of Example 7, Step A as the substrate, the desired product was isolated in a 50% yield (24 mg).

FAB-MS: M+1 at 588, M-18 at 570 (loss of $H_2O$) and M-188 at 400 (loss of imidazole fragment).

$^1$H NMR: (300 mHz, CDCl$_3$, ppm) δ7.37–6.8 (m, 14H); 5.15 (s, 2H); 4.45 (d, 2H); 4.43 (d, 1H); 4.15 (m, 1H); 3.6 (m, 6H); 3.4–3.15 (m, 2H); 2.52 (t, 2H); 1.65 (m, 2H); 1.3 (m, 2H); 0.8 (t, 3H).

EXAMPLE 8

2-Butyl-1-[4-(N-(1(R)-carboxy-1-benzyl)methyl-N-(phenylacetyl)aminomethylphenyl]methyl-4-chloro-5-hydroxymethylimidazole (Scheme I-3, Compound 16)

Following the procedure of Example 6, Step A and using the product of Example 7, Step B the desired product was isolated in a 61% yield (16 mg).

FAB-MS: M+1 at 574, M-18 at 556 and 2M+1 at 1148.

$^1$H NMR: (300 mHz, CD$_3$OD, ppm) δ7.3–6.7 (m, 14H); 5.25 (d, 2H); 5.00 (d, 0.6H); 4.9–4.8 (m, 0.4H) 4.7–4.6 (m, 1H); 4.45 (s, 2H); 4.45–4.3 (m, 1H); 3.72–3.48 (m, 2H); 3.38–3.05 (m, 1.4H); 2.70 (m, 0.6H); 2.55 (m, 2H); 1.50 (m, 2H); 1.26 (dt, 2H); 0.85 (t, 3H).

EXAMPLE 9

2-Butyl-1-[4-(N-(1(S)-carbomethoxy-1-benzyl)aminomethylphenyl]methyl-4-chloro-5-hydroxymethylimidazole Step A: Preparation of 2-Butyl-5-t-butyldimethylsilyloxymethyl-1-[4-(N-(1(S)-carbomethoxy-1-benzyl)aminomethylphenyl]methyl-4-chlorimidazole Following the procedure of Example 1, Step E but using 1.1 eq L-phenylalanine methyl ester.HCl (116 mg, 0.538 mmol) and 1.0 eq of the aldehyde prepared in Example 1, Step D in 2–3 ml ethanol over 3A molecular sieves, the product was isolated in a 59% yield (168 mg).

FAB-MS: M+1 at 584.

$^1$H NMR: (300 mHz, CDCl$_3$, ppm) δ7.32–7.22 (m, 7H); 6.90 (d, 2H), 5.15 (s, 2H); 4.50 (s, 2H); 3.80 (d, 1H); 3.65 (s, 3H); 3.60 (d, 1H); 3.50 (t, 1H); 2.95 (m, 2H); 2.50 (t, 2H); 1.6 (m, 2H); 1.30 (dt, 2H) 0.85 (t,s, 12H); 0.02 (s, 6H).

Step B: Preparation of 2-Butyl-1-[4-(N-(1(S)-carbomethoxy-1-benzyl)aminomethylphenyl]methyl-4-chloro-5-hydroxymethylimidazole Following the procedure of Example 1, Step F, and using the product of Example 9, Step A, the desilylated product was obtained in a 65% yield (13 mg).

FAB-MS: M+1 at 470.

$^1$H NMR: (300 mHz, CDCl$_3$, ppm): δ7.30–7.10 (m, 7H); 6.90 (d, 2H), 5.17 (s, 2H); 4.46 (s, 2H); 3.80 (d, 1H); 3.64 (s, 3H); 3.60 (d, 1H); 3.50 (t, 1H); 2.95 (m, 2H); 2.55 (t, 2H); 1.65 (m, 2H); 1.35 (dt, 2H) 0.90 (t, 3H).

EXAMPLE 10

2-Butyl-1-[4-(N-(1(S)-carboxy-1-benzyl)aminomethylphenyl]methyl-4-chloro-5-hydroxymethylimidazole Following the hydrolysis procedure described in Example 2, Step A, but using the product of Example 9, Step B, the free acid was isolated in a 82% yield (12 mg).

FAB-MS: M+1 at 456, trace amount of ester at 470 and M+NA at 478.

$^1$H NMR: (300 mHz, CD$_3$OD, ppm) δ7.3–7.1 (m, 7H); 7.00 (d, 2H); 5.27; (s, 2H); 4.45 (s, 2H); 3.75 (d, 1H); 3.53 (d, 1H); 3.02–2.90 (m, 1H); 2.87–2.77 (m, 1H); 2.55 (t, 2H); 1.53 (m, 2H); 1.27 (dt, 2H); 0.85 (t, 3H).

EXAMPLE 11

2-Butyl-1-[4-(N-(1(S)-carbomethoxy-1-benzyl)-N-pentanoyl)aminomethylphenyl]methyl-4-chloro-5-hydroxymethylimidazole (Scheme I-3, Compound 10)

Step A: Preparation of 2-Butyl-5-t-butyldimethylsilyloxymethyl-1-[4-(N-(1(S)-carbomethoxy-1-benzyl-N-pentanoyl)aminomethylphenyl]methyl-4-chloroimidazole Following the procedure of Example 3, Step A but using the product of Example 9, Step A and acylating with valeryl chloride gave the desired product in a 90% yield (97 mg).

FAB-MS: M+1 at 668.

$^1$H NMR: (300 mHz, CDCl$_3$, ppm) δ7.3-7.0 (m, 7H); 6.90 (d, 2H); 5.13; (s, 2H); 4.48 (s, 2H); 4.40 (d, 1H); 4.26 (t, 1H); 3.75 (d, 1H); 3.65 (s, 3H); 3.4-3.15 (m, 2H); 2.48 (t, 2H); 2.20 (m, 2H); 1.68-1.46 (m, 4H); 1.38-1.18 (m, 4H); 0.93-0.73 (m, 15H); 0.02 (s, 6H).

Step B: Preparation of 2-Butyl-1-[4-(N-(1(S)-carbomethoxy-1-benzyl-N-pentanoyl)aminomethylphenyl]methyl-4-chloro-5-hydroxymethylimidazole To a solution of Example 11, Step A (94 mg, 0.14 mmol) in THF was added 0.17 ml of 1.0M tetrabutylammonium fluoride and following the procedure of Example 1, Step F the product was isolated in a 52% yield (40.5 mg).

FAB-MS: M+1 at 554 and M-18 at 536.

$^1$H NMR: (300 mHz, CDCl$_3$, ppm) δ7.3-7.02 (m, 7H); 6.90 (d, 2H); 5.18; (s, 2H); 4.45 (s, 2H); 4.38 (d, 1H); 4.27 (m, 1H); 3.73 (d, 1H); 3.62 (s, 3H); 3.4-3.15 (m, 2H); 2.53 (t, 2H); 2.3-2.1 (m, 2H); 1.75-1.5 (m, 4H); 1.4-1.2 (m, 4H); 0.85 (m, 6H).

EXAMPLE 12

2-Butyl-1-[4-(N-(1(S)-carboxy-1-benzyl)methyl-N-pentanoyl)aminomethylphenyl]methyl-4-chloro-5-hydroxymethylimidazole sodium salt (Scheme I-3, Compound 12)

Following the procedure of Example 2, Step A the methyl ester of Example 11, Step B was hydrolyzed to give a 73% yield (23 mg) of the sodium salt.

FAB-MS: M+1 at 562, M+Na at 584, 2M+1 at 1124 and 2M+Na at 1145.

$^1$H NMR: (300 mHz, CD$_3$OD, ppm) δ7.28-6.82 (m, 9H); 5.25 (d, 2H); 5.00 (d, 1H); 4.6 (m, 4.45 (s, 2H); 4.28 (d, 1H); 3.4-3.2 (m, 1H); 3.10-2.98 (m, 0.4H); 2.85-2.75 (m, 0.6H); 2.55 (m, 2H); 2.38-1.95 (m, 2H); 1.6-1.1 (m, 8H); 0.90-0.73 (m, 6H).

EXAMPLE 13

2-Butyl-5-t-butyldimethylsilyloxymethyl-1-[4-(1-carbomethoxy-1,1-dibenzyl)methyl)aminomethylphenyl]-methyl-4-chlorimidazole (Scheme I-5, Compound 18)

Step A: Preparation of N-benzylidene-D-phenylalanine methyl ester

To a suspension of 1.0 eq D-phenylalanine HCl (1.6 g, 7.4 mmol) was added 1.0 eq triethylamine to dissolve the D-phenylalanine. To this solution was added 1 equiv. of MgSO$_4$ followed by the addition of 1.0 eq benzaldehyde, the reaction was stirred overnight at room temperature under N$_2$ atmosphere. The reaction mixture was stripped of solvent and pumped on the residue contained a good deal of triethylamine hydrochloride which was removed by dissolving the product in THF and filtering out the TEA.HCl. The crude benzylidene looked fine by NMR and was all taken on in the next step.

$^1$H NMR: (300 mHz, CDCl$_3$, ppm) 7.90 (s, 1H); 7.68 (d, 2H); 7.4 (m, 3H); 7.26-7.12 (m, 5H); 4.17 (m, 1H); 3.72 (s, 3H); 3.38 (dd, 1H), 3.15 (dd, 1H).

Step B: Preparation of Methyl-2-amino-3-phenyl-2-phenylmethypropionate (Scheme I-4, Compound 17)

To a solution of the benzylidene, Example 13, Step A, in 25 ml dry THF at −78° C. was added 1.05 eq of 1.0M lithium hexamethyldisilylazide in THF (7.8 ml) over 10 minutes. After 30 minutes, a solution of 1.05 eq benzyl bromide in 15 ml THF was added over 15 minutes. The reaction mixture was stirred at −70° C. for 15 min. and then gradually warmed to −40° to −35° C. and stirred at this temperature for 1.5 hours, after which the reaction appeared to be complete. The reaction mixture was quenched at −35° C. by the addition of 50 ml of 1.0 N HCl and it was then allowed to warm to room temperature with stirring. The reaction mixture was then extracted twice with hexane to remove the bezaldehyde which had been formed. The aqueous layer was then extracted three times with ethyl acetate, and the combined extracts were washed with saturated NaHCO$_3$ and brine, then dried over MgSO$_4$. The solvent was removed in vacuo to give 324 mg of a yellow crystalline solid. The pH of the aqueous layer was adjusted from 1.4 to 11.8 using 3N NaOH producing a milky white solution, which became clear upon addition of ethyl acetate. The basic aqueous layer was extracted twice more with ethyl acetate, and the combined extracts were washed with brine and dried over MgSO$_4$. The solvent was removed in vacuo to give a colorless oil (1.37 g) giving a total yield of 85%.

FAB-MS: M+H=270. 3, ppm); δ7.3-7.15 (m, 10H); 3.65 (s, 3H); 3.37 (d, 2H); 2.74 (d, 2H).

Step C: Preparation of 2-Butyl-5-t-butyldimethylsilyoxymethyl-1-[4-(1-carbomethoxy-1,1-dibenzyl)methyl)aminomethylphenyl]methyl-4-chloroimidazole (Scheme I-5, Compound 18)

To a solution of 1.1 eq of the product of Example 13, Step B (0.32 g, 1.2 mmol) in 15 ml CH$_2$Cl$_2$ over MgSO$_4$ after 15 min was added 1.0 eq of the aldehyde of Example 1, Step D (0.46 g, 1.09 mmol) and the reaction mixture was allowed to stir at room temperature under N$_2$ over the weekend. The reaction mixture was then filtered and concentrated in vacuo. The reaction mixture was dissolved in toluene and warmed to reflux under a Dean-Stark trap for 3 hrs. The reaction mixture was then cooled to room temperature under N$_2$ and 3.0 eq of 1.0M NaCNBH$_3$ was added. The reaction mixture was stirred at room temperature overnight, then the solvent was removed in vacuo. The residue was dissolved in ethyl acetate and water, and the layers separated slowly and the organic layer washed with brine, dried over MgSO$_4$, filtered and stripped of solvent. The residue was chromatographed on silica gel eluting with 4:1 hexane:ethyl acetate and two fractions were isolated. The first fraction contained a mixture of the Schiff's base and the desired product (378 mg, 51%) and the second fraction contained the product (43mg). The mixture was rechromatographed eluting with 15% ethyl acetate and hexane and the product (108 mg) was isolated in the first fraction to give a total yield of 20.5% (153 mg). The second fraction contained 90 mg of a mixture of the Schiff's base and the desired product.

FAB-MS: M+H=674.

$^1$H NMR: (300 mHz, CDCl$_3$, ppm) δ7.3-7.15 (m, 12H); 6.95 (d, 2H); 5.17 (s, 2H); 4.53 (s, 2H); 3.87 (s, 2H); 3.63 (s, 3H); 3.23 (d, 2H); 3.07 (d, 2H); 2.54 (t, 2H); 1.66 (m, 2H); 1.34 (dt, 2H); 0.86 (m, 12H); 0.04 (s, 6H).

EXAMPLE 14

2-Butyl-1-[4-(N-(1-carbomethoxy-1,1-dibenzyl)methyl)aminomethylphenyl]methyl-4-chloro-5-hydroxymethylimidazole (Scheme I-5, Compound 19)

To a solution of the product of Example 13, Step C (67 mg, 0.10 mmol) in 2.0 ml of THF, was added 1.2 eq of 1.0M tetrabutylammonium fluoride in THF and the procedure of Example 1, Step F was followed. The desilylated product was isolated (65 mg; 100%).

FAB-MS: M+H=560. $^1$H NMR: (300 mHz, CDCl$_3$ ppm) δ7.35-7.15 (m, 12H); 6.90 (d, 2H); 5.20 (s, 2H); 4.45 (s, 2H); 3.87 (s, 2H); 3.64 (s, 3H); 3.20 (d, 2H); 3.05 (d, 2H); 2.55 (t, 2H); 1.67 (m, 2H); 1.35 (m, 2H); 0.88 (t, 3H).

EXAMPLE 15

2-Butyl-1-[4-(N-(1-carboxy-1,1-dibenzyl)methyl)aminomethylphenyl]phenyl]methyl-4-chloro-5-hydroxymethylimidazole (Scheme I-5, Compound 20)

The hydrolysis procedure of Example 2, Step A was follwed using the product of Example 14, Step B. The reaction was run overnight, but appeared to be incomplete, and was refluxed at 100° C. for 4 hrs. An additional 2 eq of 2.0N NaOH (0.1 ml) was added and the reaction mixture was allowed to reflux for two days. The reaction mixture became cloudy on cooling to room temperature and was filtered. The filtrate was acidified with concentrated HCl and stirred for 1 hr. The solvent was removed in vacuo and the water azeotroped off with toluene and acetonitrile. The residue was chromatographed on a sephadex column, eluting with methanol yielding both the acid and ester. This fraction was chromatographed on silica gel eluting with 11:1 CH$_2$Cl$_2$:CH$_3$OH to elute the ester and then 11:1:0.5 CH$_2$Cl$_2$:CH$_3$OH:HOAc to elute the acid in a 44% yield (27 mg).

FAB-MS: M+1 at 546 and M−19 at 528.

$^1$H NMR: (300 mHz, CD$_3$OD, ppm) δ7.5-7.12 (m, 12H); 7.00 (d, 2H); 5.30 (s, 2H); 4.45 (s, 2H); 4.06 (s, 2H); 3.43 (s, 2H); 3.18 (d, 2H); 2.52 (t, 2H); 1.2 (t, 2H); 1.28 (m, 2H); 0.85 (m, 3H).

EXAMPLE 16

1-[4-(1-(N-benzyl-N-pentanoyl)amino-1-(tetrazol-5-yl)methylphenyl]methyl-2-butyl-5-t-butyldimethylsilyloxymethyl-4-chloroimidazole (Scheme I-6, Compound 23)

Step A: Preparation of 1-[4-(1-(N-benzyl)amino-1-cyano)methylphenyl]methyl-2-butyl-5-t-butyldimethylsilyloxymethyl-4-chloroimidazole To a solution of the product of Example 1, Step D in 2-3 ml of CH$_2$Cl$_2$ over MgSO$_4$ was added 1.7 eq of benzylamine and the reaction mixture was allowed to stir for 2 days. The Schiff base formation was not complete, as indicated by TLC. Trimethylsilylcyanide (1.1 eq) was added and the reaction mixture was allowed to stir overnight at room temperature. The reaction mixture was filtered and the filtrate was stripped of CH$_2$Cl$_2$, dissolved in ethyl acetate, washed twice with water and once with brine, and then dried over MgSO$_4$. The solvent was removed in vacuo, and the residue was acylated in the next step.

FAB-MS: M+1 at 537.

$^1$H NMR: (300 mHz, CDCl$_3$, ppm) δ7.50 (d, 2H); 7.3-7.2 (m, 5H); 7.03 (d, 2H); 5.20 (s, 2H); 4.73 (s, 1H); 4.50 (s, 2H); 4.05 (d, 1H); 3.95 (d, 1H); 2.50 (t, 2H); 1.65 (m, 2H); 1.30 (dt, 2H); 0.85 (m, 12H); 0.02 (s, 6H).

Step B: Preparation of 1-[4-(1-(N-benzyl-N-pentanoylamino-1-cyano)methylphenyl]methyl-2-butyl-5-t-butyldimethylsilyloxymethyl-4-chloroimidazole Following the acylation procedure of Example 3, Step A but using the product of Example 16, Step A (132 mg, 0.246 mmol) and 1.2 eq of valeroyl chloride (35 ul, 0.295 mmol) and 1.5 eq of triethylamine (51 μl, 0.368 mmol). The reaction appeared to be incomplete after stirring for a few hours and was allowed to continue overnight. The reaction mixture was filtered and the filtrate was stripped of solvent. The residue was chromatographed on silica gel eluting with 4:1 hexane:ethyl acetate. The two fractions isolated were mixtures, containing both the acylated product and starting materials. These two fractions were combined and acylated again using 1.6 eq valeroyl chloride and 1.9 eq triethylamine in THF, stirring at room temperature overnight. The same workup procedure as described above was used, and the material was chromatographed on silica gel eluting with 4:1 hexane:ethyl acetate. The product was isolated in a 33% yield (50 mg).

FAB-MS: M+1 at 621.

$^1$H NMR: (300 mHz, CDCl$_3$, ppm) δ7.4-6.96 (m, 9H); 5.15 (s, 2H); 4.55-4.4 (m, 5H); 2.48 (t, 2H); 2.28 (t, 2H); 1.63 (m, 4H); 1.3 (m, 4H); 0.85 (m, 12H); 0.02 (s, 6H).

Step C: Preparation of 1-[4-(1-(N-benzyl-N-pentanoyl)amino-1-(N-trimethylstannyltetrazol-5-yl))methylphenyl]methyl-2-butyl-5-t-butyldimethylsilyloxymethyl-4-chloroimidazole To a solution of 1.0 eq of the product of Example 16, Step B in 2 ml of dry toluene was added 1.2 eq trimethylstannylazide and the mixture was gradually warmed to reflux in toluene overnight. The TLC and crude 1H NMR indicated the disappearance of starting material, and the crude material was carried on to the next step.

$^1$H NMR: (300 mHz, CDCl$_3$, ppm) δ7.6-6.6 (m, 9H); 5.12 (s, 2H); 4.95 (d, 1H); 4.75 (d, 1H); 4.55-4.37 (m, 3H); 2.6-2.4 (m, 2H); 2.4-2.1 (m, 2H); 1.7-1.5 (m, 4H); 1.4-1.2 (m, 4H); 1.00-0.8 (m, 12H); 0.70 (s, 6H) 0.02 (s, 6H).

Step D: Preparation of 1-[4-(1-(N-Benzyl-N-pentanoyl)amino-1-(tetrazol-5-yl))methylphenyl]methyl-2-butyl-4-chloro-5-hydroxymethylimidazole To a 2 ml solution of the product of Example 16, Step C (theoretically 66 mg, 0.08 mmol) at room temperature was added 5 drops of concentrated HCl. The reaction mixture became hot, was cooled with an ice bath and stirred, and was then allowed to warm to room temperature. The reaction mixture was stirred for about an hour at room temperature and appeared to be complete. The solvent was removed in vacuo and the residue chromatographed on silica gel eluting with 40:10:1 CHCl$_3$:CH$_3$OH:NH$_4$OH and the product isolated in a 25% yield (10 mg).

FAB-MS: M+1 at 550, M+Na at 572 and M−18 at 532.

$^1$H NMR: (300 mHz, CD$_3$OD, ppm) δ7.5-6.7 (m, 9H); 5.25 (s, 2H); 5.0-4.7 (m, 2H); 4.35 (s, 2H); 2.63 (m, 0.5H); 2.52 (t, 2H); 2.30 (t, 1.5H); 1.68-1.45 (m, 4H); 1.4-1.15 (m, 4H); 0.95-0.75 (m, 6H).

EXAMPLE 17

2-Butyl-4-chloro-5-hydroxymethyl-3-[4-(1-hydroxy-1-phenyl-1-(tetrazol-5-yl))methylphenyl]methylimidazole (Scheme I-9, Compound 39

Step A: Preparation of 4-bromomethylbenzophenone

1 To a solution of 4-methylbenzophenone (3.0 g, 15.3 mmol) in 60 ml $CCl_4$ was added N-bromosuccinimide (3.0 g, 1.1 eq) and AIBN (30 mg). The solution was refluxed for 4.5 h, then cooled to room temperature. The succinimide were removed by filtration, and the filtrate was concentrated to dryness. Recrystallization required large amounts of solvent and chromatography appeared a better alternative. The residue was chromatographed on silica gel eluting with 5% Ethyl Acetate/Hexane (3.44 g; 82% yield).

$^1$NMR (300 MHz, $CDCl_3$, ppm): δ4.55 (s, 2H); 7.5 (m, 4H, 7.6 (m, 1H); 7.8 (m, 4H).

Step B: Preparation of 1-(4-benzoyl)phenylmethyl-2-butyl-5-t-butyldimethylsilyloxymethyl-4-chloroimidazole To a suspension of NaH (0.21 g, 6.97 mmol) in 15 ml of DMF was added 2-butyl-5-t-butyldimethylsilyloxymethyl-4-chloroimidazole (2.0 g, 6.62 mmol) and the solution was stirred for 45 min. under $N_2$. To this solution was added 4-bromomethylbenzophenone (1.82 g, 6.62 mmol) and the mixture was stirred for 4.5 hrs. The reaction mixture was quenched with saturated ammonium chloride, and the solvent was removed in vacuo. The residue was dissolved in ethyl acetate, washed with $H_2O$ and brine, dried over $MgSO_4$ filtered and concentrated in vacuo. The crude product was chromatographed on silica gel (170 mm × 50 mm) in two batches, eluting with 15% ethyl acetate in hexane. The product was isolated in a 71% yield (2.36 g).

$^1$H NMR (300 MHz, $CDCl_3$, ppm); δ0.1 (s, 6H), 0.80–1.0 (m, 12H), 1.3–1.45 (m, 2H), 1.6–1.75 (m, 2H), 2.5–2.6 (t, 2H), 4.55 (s, 2H, 7.1 (d, 2H), 7.5 (d, 2H, 7.6 (m, 1H), 7:7–7.8 (m, 4H).

Step C: Preparation of 2-butyl-5-t-butyldimethylsilyloxymethyl-4-chloro-1-[4-(1-cyano-1-phenyl-1-trimethylsilyloxy)methylphenyl]methylimidazole To a 2 ml $CH_2Cl_2$ solution of the ketone of Example 17, Step B (0.50 g, 1.0 mmol) under $N_2$ was added trimethylsilylcyanide (TMSCN) (85 mg, 1.2 mmol), followed by the addition of KCN (10 mg) and 18-crown-6 (10 mg). The reaction was followed by TLC, and was complete in 3 hrs. The solution was diluted with diethyl ether (~30 ml and washed with dilute $NaHCO_3$. and brine then organic extract was dried over $MgSO_4$., filtered and the solvent removed invacuo. The product was isolated in a 67% yield (0.40 g)

$^1$H NMR (300 MH, $CDCl_3$, ppm): δ0.05 (s, 9H), 0.10 (s, 6H), 0.8–0.9 (m, 12H), 1.3–1.45(m, 2H), 1.55–1.65(M, 2H), 2.4–2.5(t, 3H), 4.5(s, 2H), 5.2 (s, 2H) 7.0(d, 2H), 7.3–7.4(M, 3H), 7.4–7.5(m, 4H)

Step D: Preparation of 2-butyl-5-t-butyldimethylsilyloxymethyl-4-chloro-1-[4-(1-hydroxy-1-phenyl-1-(tetrazol-5-yl))methylphenyl]methylimidazole To a solution of Example 17, Step C (0.1 g, 0.17 mmol) in 500 ml of toluene was added trimethylstannyl azide (41 mg, 0.20 mmol) at room temperature and the reaction was then heated to reflux for 24 hrs. The reaction was followed by TLC and after 7 days was 60% complete. The residue was chromatographed on silica gel (120×15 mm), eluting with 15% ethyl acetate in hexane containing a few drops of $CH_3OH$. The product was isolated in a 15% yield (20 mg).

$^1$H NMR (300 MHz, $CDCl_3$, ppm): δ0.1 (s, 6H), 0.8–0.9 (m, 12H, 1.25–1.40 (m, 2H), 1.6–1.7(m, 2H), 2.5(t, 2H), 4.5(s, 2H), 5.25(s, 2H), 7.1(d, 2H), 7.4–7.6(m, 3H), 7.7–7.8(m, 4H).

EXAMPLE 18

2-Butyl-1-[4-(1-carboxy-1-(2-chloro)phenyl)methoxyphenyl]methyl-4-chloro-5-hydroxymethylimidazole (Scheme I-8, Compound 33)

Step A: Preparation of Methyl 2-bromo-2'-chlorophenylacetate o-Chlorophenylacetic acid (5.00 g, 29.3 mmol) and thionyl chloride (2.67 ml, 36.6 mmol) are heated to reflux. Bromine (1.51 ml, 29.3 mmol) was added dropwise over 10 minutes and continued to reflux for 17 hrs. The reaction was cooled to room temperature and 30 ml of $CH_3OH$ was added slowly. The solvent was removed in vacuo and the residue chromatographed on silica gel eluting with 5% ethyl acetate in hexane. The product was isolated in a 28% yield (2.13 g).

$^1$H NMR (300 MHz, $CDCl_3$, ppm): 3.8 (s, 3H); 5.95 (s, 1H); 7.25–7.45 (m, 3H); 7.7–7.8 (m, 1H).

Step B: Preparation of Methyl 2-(4-methylphenoxy)-2-(2'-chlorophenyl)acetate

To a suspension of KH (0.53 g, 4.63 mmol) in 5 ml of DMF under $N_2$ at 0° C. was added p-cresol (0.5 g, 4.63 mmol). The reaction mixture was stirred until the evolution of $H_2$ was complete. Then 50 mg of 18-crown-6 ether was added, followed by the product of Example 18, Step A (1.22 g, 4.63 mmol) in 5 ml DMF. The reaction mixture was stirred at 0° C. for 30 minutes and then allowed to warm to room temperature. The reaction mixture was concentrated in vacuo and chromatographed on silica gel (130 mm×30 min) eluting with 5% ethyl acetate in hexane. The product was isolated in a 77% yield (1.03 g).

FAB-MS: 290,292.

$^1$H NMR (300 MHz, $CDCl_3$, ppm): δ2.25 (S, 3HO 3.8 (S, 3H) 6.15 (S, 1H) 6.8–6.9 (d, 2H) 7.25–7.35 (m, 2H) 7.4–7.5 (m, 1H) 7.6–7.7 (m, 1H) 7.6–7.7 (m, 1H).

Step C: Preparation of Methyl 2-(4-bromomethylphenoxy)-2-(2'-chlorophenyl)acetate A solution of the product of Example 18, Step B (0.2 g, 0.69 mmol), N-bromosuccinimide (117 mg, 166 mmol) and a catalytic amount of AIBN in 2 ml $CCl_4$ was refluxed for 30 minutes. The reaction mixture was concentrated in vacuo and chromatographed on silica gel (125×20 mm) eluting with 5% ethyl acetate in hexane. The product was isolated in a 73% yield (186 mg).

FAB-MS: 368, 370, 372 (10:13:3 isotopic ratio due to the presence of a chlorine and a bromine).

$^1$H NMR (300 MHz, $CDCl_3$, ppm): 3.8 (s, 3H) 4.5 (S, 2H); 6.15 (s, 1H); 6.85–6.95 (d, 2H); 7.25–7.35 (m, 4H); 7.4–7.5 (m, 1H); 7.6–7.7 (m, 1H).

Step D: Preparation of 2-butyl-5-t-butyldimethylsilyloxymethyl-1-[4-(1-carbomethoxy-1-(2-chloro)phenyl)methoxyphenyl]methyl-4-chloroimidazole To a suspension of NaH (2.7 mg, 89 mmol) in 250 μl DMF was added 2-butyl-4-chloro-5-t-butyldimethylsilyloxymethylimidazole and stirred for 15 minutes. To this solution was added a solution of the product of Example 18, Step C (30 mg, 81.3 mmol) in DMF (0.25 ml) and the reaction mixture was stirred for 2 hrs at room temperature. The reaction mixture was stored over the weekend at −30° C. and then warmed to room temperature and stirred for 4 hrs. The reaction was concentrated in vacuo and chromatographed on silica gel (130×20 mm) eluting with 15% ethyl acetate in hexane. The product was isolated in a 65% yield (31 mg).

$^1$H NMR (300 MHz, CDCl$_3$, ppm): δ0.05 (s, 6H); 0.8-0.9 (m, 12H); 1.2-1.35 (m, 2H); 1.5-1.65 (m, 2H); 1.95-2.05 (t, 2H); 3.75 (s, 3H); 4.5 (s, 2H) 15.1 (s, 2H) 6.1 (s, 1H); 6.85-6.95 (m, 4H); 7.25-7.35 (m, 2H); 7.4-7.5 (m, 1H); 7.5-7.6 (m, 1H).

Step E: Preparation of 2-Butyl-1-(1-carboxy-1-(2-chloro)phenyl)methoxyphenyl]methyl-4-chloro-5-hydroxymethylimidazole To a solution of the product of Example 18, Step D (30 mg, 0.51 mmol) in CH$_3$OH (0.5 ml) was added in NaOH until the reaction became cloudy (500 μl). The reaction mixture was stirred for 24 hours and then concentrated in vacuo. The residue was dissolved in 5 ml of a 1:1 concentrated HCl:THF solution and stirred overnight. The reaction mixture was neutralized with 6N NaOH, and concentrated in vacuo. The residue was dissolved in ethyl acetate, filtered, and concentrated in vacuo. The crude product was chromatographed on silica gel (120×15 mm) eluting with 100:3:1 CHCl$_3$:CH$_3$OH:CH$_3$CO$_2$H. The product was isolated in a 38% yield (9 mg).

$^1$H NMR (300 MHz, CD$_3$OD, ppm): δ0.75-0.85 (t, 3H), 1.2-1.35 (m, 2H), 1.35-1.5 (m, 2H), 2.5-2.6 (t, 2H), 4.5 (s, 2H), 5.2 s, 2H), 6.1 (s, 1H), 6.9-7.1 (m, 4H), 7.3-7.4 (m, 2H), 7.4-7.5 (m, 1H), 7.55-7.65 (m, 1H).

EXAMPLE 19

2-Butyl-4-chloro-5-hydroxymethyl-1-[4-(1-phenyl-1-tetrazol-5-yl))methylphenyl]methylimidazole (Scheme I-11, Compound 44)

Step A: Preparation of 4-(bromomethyl)benzylalcohol

A suspension of 4-bromomethylbenzoic acid (5.04; 23.3 mmol) in THF (30 ml) was cooled to 0° C. and treated with borane/THF (35 mmol). The ice bath was removed and the mixture was allowed to warm to room temperature and stirred for 1.5 hours. The excess borane was quenched with MeOH, and then with water, and the reaction mixture was concentrated in vacuo. The residue was dissolved in ethyl acetate and washed with 4% HCl, water NaHCO$_3$, brine, dried (MgSO$_4$), filtered, concentrated in vacuo to afford 4.44 g (94%) of the title compound.

$^1$H NMR: (300 MHz, CDCl$_3$, ppm): 7.38 (q, 4H); 4.70 (s,2H); 4.51 (s,2H).

FAB MS: m/e=202 (M+H).

Step B: Preparation of 4-(bromomethyl)-t-butyldimethylsilyloxymethylbenzene

To a solution of the product of Example 19, Step A (4.44 g, 22.1 mmol) in CH$_2$Cl$_2$ was added N,N-diisopropylethyl amine (1.2 eq.) and 4-dimethylaminopyridine (0.1 eq), and t-butyldimethylsilyl chloride (1.2 eq). The mixture was stirred for 1.5 hours at room temperature, then concentrated in vacuo. The residue was dissolved in ethyl acetate and washed with water, brine, dried (MgSO$_4$), filtered, and concentrated in vacuo. The residue was chromatographed on silica (ethyl acetate/hexanes (2.5/97.5)) to afford 5.0 g (71%) of the title compound.

$^1$H NMR (300 MHz, CDCl$_3$, ppm): 7.34 (q,4H); 4.74 (s,2H); 4.59 (s,2H); 0.95 (s,9H); 0.11 (s,6HO).

Step C: Preparation of 3-(4-t-butyldimethylsilyloxymethyl)phenyl-2-phenylpropionitrile A solution of benzyl cyanide (1.5 ml, 12.7 mmol) in THF (40 ml) containing HMPA (11 ml, 63.4 mmol) was cooled to −78° C. and treated with lithium bis trimethylsilyamide (16 ml, 16 mmol of 1.0M in THF) dropwise to maintain temperature below −73° C. The reaction was stirred at −78° C. for 1.5 hours. A solution of the product of Example 19, Step B (2.0 g, 6.34 mmol) in THF (8 ml) was added dropwise while the temperature was maintained below −70° C. The reaction temperature was maintained below −68° C. for 3 hours. The reaction mixture was quenched at this temperature with 1N NaHSO$_4$. After warming to room temperature, the mixture was extracted with EtOAc, the combined organic layers were washed with water, saturated NaHCO$_3$, brine, dried (MgSO$_4$), filtered, then concentrated in vacuo. The residue was chromatographed on silica (ethyl/hexanes (5/95)) to afford 1.5 g (67%) of product.

$^1$H NMR (300 MHz, CDCl$_3$, ppm): δ7.40-7.30 (m,3H); 7.30-7.22 (m,4H); 7.10 (d,2H); 4.73 (s,2H); 3.98 (t,1H); 3.23-3.08 (m,2H); 0.94 (s,9H); 0.10 (s,6H).

FAB MS: m/e=294 (loss of t-Bu).

Step D: Preparation 3-(4-bromomethyl)phenyl-2-phenylpropionitrile

The product of Example 19, Step C (1.5 g, 4.27 mmol) was treated with CBr$_4$ (1 eq.) and Ph$_3$P (1 eq) in a 1:1 mixture of acetone and acetonitrile, affording in 575 mg (45%) of the title compound after silica chromatography (ethyl acetate/hexanes (5/95)).

$^1$H NMR (300 MHz, CDCl$_3$, ppm): δ7.48-7.10 (m,9H); 4.50 (s,2H); 4.00 (t,1H); 3.26-3.10 (m,2H).

FAB MS: m/e=299/301.

Step E: Preparation of 4-chloro-2-butyl-5-t-butyldimethylsilyloxymethyl-1-[4-(1-cyano-1-phenyl)methylphenyl]methylimidazole Sodium hydride (1.2 eq 16 mg of 80% oil dispersion) was suspended in dry DMF (1 ml) cooled at 0° C. under N$_2$, and 1.0 eq (137 mg, 0.42 mmol) of 2-butyl-4-chloro-5-t-butyldimethylsilyloxymethylimidazole in 1.5 ml DMF was added dropwise, causing vigorous bubbling and foaming. The reaction was allowed to stir at 0° C. for 45 minutes, and then a solution of bromide (Example 19, Step D) in 1.5 ml DMF was added. The ice bath was removed, and the reaction mixture was allowed to warm gradually to room temperature. A gradual color change to darker reddish was visible. The TLC (20% EtOAc/Hexane) indicated that no bromide remained. The reaction mixture was allowed to stir at room temperature overnight, and then the solvent was removed in vacuo. The residue was dissolved in EtOAc and washed with H$_2$O. The combined organic portions were extracted with H$_2$O and brine, and dried (Na$_2$SO$_4$). The crude material was chromatographed on silica gel using MPLC eluting with 15% EtOAc in hexane, giving the desired product (69 mg; 29% yield).

FAB MS: M+H=522.

Step F: Preparation of 2-butyl-4-chloro-5-hydroxymethyl-1-[4-(1-phenyl-1-(tetrazol-5-yl))methylphenyl]methylimidazole The product of Example 19, Step D (69 mg, 0.132 mmol) was dissolved in 2 ml dry toluene, 1-2 eq of trimethylstannylazide was added and the mixture was heated to reflux under a blanket of N$_2$. After refluxing for 22 hrs, the reaction was brown in color. By TLC (30% EtOAc/Hexane) a substantial amount of unreacted nitrile still remained. The solvent was removed in vacuo and the reaction checked by NMR, which confirmed that 25% unreacted nitrile remained. An additional equivalent of trimethylstannylazide was added to a toluene solution of the mixture, and the solution was heated to reflux for 5 hr, by TLC some nitrile still remained. The reaction mixture was allowed to cool slowly to room temperature and was stirred overnight. The reaction was stripped of toluene, dissolved in THF cooled in ice and concentrated HCl (3 drops) was added. The solvent was azeotroped off from toluene/$CH_3CN$. The crude material was chromatographed on silica gel in 85:15 $CHCl_3$: 10% $NH_4OH$/MeOH. The desired product was isolated in 35 mg (60% yield).

FAB MS: M+H=451.

$^1H$ NMR (300 mHz,$CD_3OD$, ppm): δ7.32–7.18 (m.5H); 7.09 (d,2H); 6.90 (d,2H); 5.21(s,2H); 4.63(t,1H); 4.42(s.2H); 3.63–3.52 (dd,1H); 3.42–3.31(dd, 1H); 2.50(t,2H); 1.52–1.39(m.2H); 1.32–1.18(m,2H); 0.82(t,3H).

EXAMPLE 20

2-Butyl-1-[4-(N-(1-carboxy-1-(2-phenyl)ethyl)aminophenyl]methyl-4-chloro-5-hydroxymethylimidazole Step A: Preparation of 2-Butyl-1-[4-(N-(1-carboxy-1-(2-phenyl)ethyl)aminophenyl]methyl-4-chloro-5-hydroxymethylimidazole A solution of 204 mg (0.500 mmol) (4-aminophenyl)-methyl-2-butyl-4-chloro-5-butyldimethylsilyloxymethylimidazole in 0.25 ml methanol was treated with 132 mg (0.575 mmol) methyl-2-phenyl-2-bromoacetate and 50 mg (0.595 mmol) sodium bicarbonate and a crystal of potassium iodide. After stirring overnight the reaction mixture was concentrated under vacuum, extracted into 5 ml methylene chloride and, after removal of the solvent under vacuum, charged with 1 ml methanol to a column of LH-20. The product-containing fractions were collected and evaporated to yield 241 mg (87%) with correct NMR and mass spectrum and single spot by TLC.

Step B: Preparation of 2-Butyl-5-t-butyldimethyl-silyloxymethyl-1-[4-(N-(1-carboxy-1-phenyl)methyl-)aminophenyl]methyl-4-chloroimidazole A solution of 186 mg of the product of Example 20, Step A and 1 ml of 1N sodium hydroxide in 2 ml of methanol was allowed to stir for 4 hrs. After addition of 5 ml ethyl acetate the solution was extracted with 2×5 ml 5% aqueous citric acid. The ethyl acetate solution was dried and concentrated to yield 221 mg (90%) citrate salt of the product which had correct mass spectrum and NMR.

Step C: Preparation of 2-Butyl-1-[4-(N-(1-phenyl-)aminophenyl]methyl-4-chloro-5-hydroxymethylimidazole A reaction mixture containing 212 mg of the product of Example 20, Step B in 420 ml 1 Molar tetrabutylammonium fluoride was allowed to stand at room temperature overnight, concentrated under vacuum to an oil which was treated with 10 ml ethyl acetate and extracted with 4×15 ml 5% aqueous citric acid. After drying and evaporation of the ethyl acetate there was obtained 143 mg (78%) of a citrate, single spot by TLC and with NMR and mass spectrum in accord with the structure.

Step D: Preparation of 2-Butyl-1-[4-N-(1-carboethoxy)-1-(2-phenyl)methyl)aminophenyl]methyl-4-chloro-5-hydroxymethylimidazole A slurry of 207 mg (0.507 mmol) the product of Example 20, Step C, 429 mg (2.081 mmol) ethyl-2-oxo-4-phenylbutanoate, and 500 mg freshly flamed 3A finely ground molecular sieves in 5 ml methanol was stirred for 6 hrs and then treated over a 1/2 hr period with 80 mg (1.27 mmol) sodium cyanoborohydride in 2 ml methanol. After stirring for 41 hr, 165 mg (1.42 mmol) pyridine hydrochloride was added and after 1 hr stirring the reaction mixture was filtered and concentrated under vacuum to a viscous oil. The oil was dissolved in 10 ml methanol and charged to 80 ml Dowex 50 (H+) set up in methanol. Neutrals and anionics were removed with 200 ml methanol and the product was eluted with 400 ml 4% pyridine in methanol. The eluent was concentrated to an oil and charged with 1 ml methanol to a LH-20 column. The product containing fractions yielded on evaporation 122.5 mg (49.9%) of product single spot TLC, correct NMR and mass spectra.

Step E: Preparation of 2-Butyl-1-[4-(N-(1-carboxy-1-(2-phenyl)ethyl)aminophenyl]methyl-4-chloro-5-hydroxymethylimidazole A solution of 118 mg (0.252 mmol) of the product of Example 20, Step D and 0.55 ml 1N sodium hydroxide in 1.5 ml of methanol were allowed to react for 5 hr at room temperature and for 16 hrs in the refrigerator. After addition of 5 ml ethyl acetate the reaction mixture was extracted with 2×5 ml 5% aqueous citric acid. The ethyl acetate was dried, and concentrated under vacuum to yield 157 mg (96%) of the product as a citrate, with NMR and mass spectra in accord with the structure.

What is claimed is:

1. A compound of Formula 1 which is

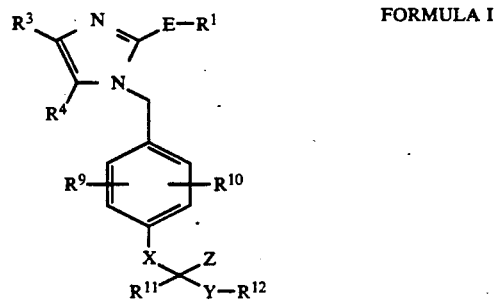

FORMULA I or a pharmaceutically acceptable salt thereof wherein: $R^1$ is:

(a) $(C_1-C_6)$-alkyl, $(C_2-C_6)$-alkenyl or $(C_2-C_6)$-alkynyl each of which is unsubstituted or substituted with a substituent selected from the group consisting of:

i) aryl as defined below,
ii) $(C_3-C_7)$-cycloalkyl,
iii) Cl, Br, I, F,
iv) $COOR^2$,
vii) $N[((C_1-C_4)-alkyl)]_2$,
viii) $NHSO_2R^2$,
ix) $CF_3$,
x) $COOR^2$, or
xi) $SO_2NHR^{2a}$; and (b) aryl, wherein aryl is defined as phenyl or naphthyl, unsubstituted or substituted with 1 or 2 substituents selected from the group consisting of:

i) Cl, Br, F, I,
ii) $(C_1-C_4)$-alkyl,
iii) $(C_1-C_4)$-alkoxy,
iv) $NO_2$ v) $CF_3$
vi) $SO_2NR^{2a}R^{2a}$,
vii) $(C_1-C_4)$-alkylthio,
viii) hydroxy,
ix) amino,
x) $(C_3-C_7)$-cycloalkyl,
xi) $(C_3-C_{10})$-alkenyl; and E is:
(a) a single bond,
(b) $-S(O)_x(CH_2)_s-$, or
(c) $-O-$; and x is 0 to 2,
s is 0 to 5;
m is 1 to 5;
p is 0 to 3;
n is 1 to 10;

$R^2$ is:
(a) H, or
(b) $(C_1-C_6)$-alkyl, and $R^{2a}$ is:
(a) $R^2$,
(b) $CH_2$-aryl, or
(c) aryl; and $R^3$ is:
(a) H,
(b) $(C_1-C_6)$-alkyl, $(C_2-C_6)$-alkenyl or $(C_2-C_6)$-alkynyl,
(c) Cl, Br, I, F,
(d) $NO_2$
(e) $(C_1-C_8)$-perfluoroalkyl,
(f) $C_6F_5$,
(g) CN,
(h) $NH_2$,
(i) $NH[(C_1-C_4)\text{-alkyl}]$,
(j) $N[(C_1-C_4)\text{-alkyl}]_2$,
(k) $NH[CO(C_1-C_4)\text{-alkyl}]$,
(l) $N[(C_1-C_4)\text{-alkyl})-(CO(C_1-C_4)\text{-alkyl})]$,
(m) $N(C_1-C_4)\text{-alkyl-COaryl}$,
(n) $N(C_1-C_4)\text{alkyl-SO}_2\text{aryl}$,
(o) $CO_2H$,
(p) $CO_2R^{2a}$,
(q) phenyl,
(r) phenyl-$(C_1-C_3)$-alkyl,
(s) phenyl and phenyl-$(C_1-C_3)$-alkyl substituted on the phenyl ring with one or two substituents selected from:
  i) $(C_1-C_4)$-alkyl,
  ii) $(C_1-C_4)$-alkoxyl,
  iii) F, Cl, Br, I,
  iv) hydroxyl,
  v) methoxyl,
  vi) $CF_3$,
  vii) $CO_2R^{2a}$, or
  viii) $NO_2$; and $R^4$ is:
(a) H,
(b) CN,
(c) $(C_1-C_8)$-alkyl,
(d) $(C_3-C_6)$-alkenyl,
(e) $(C_1-C_8)$-perfluoroalkyl,
(f) $(C_1-C_8)$-perfluoroalkenyl,
(g) $NH_2$,
(h) $NH(C_1-C_4)$-alkyl,
(i) $N[(C_1-C_4)\text{-alkyl}]_2$,
(j) $NH(C_1-C_4)$-acyl,
(k) $N[((C_1-C_4)\text{-acyl})((C_1-C_4)\text{-alkyl})]$,
(l) $CO_2H$,
(m) $CO_2R^{24}$,
(n) phenyl,
(o) phenyl-$(C_2-C_6)$-alkenyl, (p) 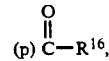 $\overset{O}{\underset{\|}{C}}-R^{16}$, (q) 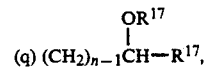 $(CH_2)_{n-1}\overset{OR^{17}}{\underset{|}{CH}}-R^{17}$, (r) 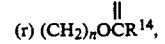 $(CH_2)_n O\overset{O}{\underset{\|}{C}}R^{14}$, (s) $(CH_2)_n SR^{15}$, (t) 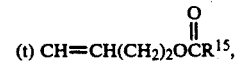 $CH=CH(CH_2)_2 O\overset{O}{\underset{\|}{C}}R^{15}$, (u) $CH=CH(CH_2)_s\overset{O}{\underset{\|}{C}}R^{17}$, (v) 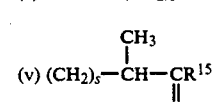 $(CH_2)_s-\overset{CH_3}{\underset{|}{CH}}-\overset{}{\underset{\overset{\|}{O}}{C}}R^{15}$, (w) $(CH_2)_n\overset{O}{\underset{\|}{C}}R^{15}$, (x) 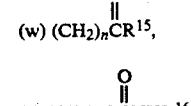 $(CH_2)_n O\overset{O}{\underset{\|}{C}}NHR^{16}$, (y) 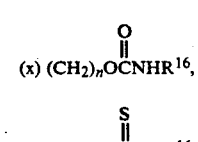 $(CH_2)_n O\overset{S}{\underset{\|}{C}}NHR^{16}$, (z) $(CH_2)_n NHSO_2 R^{16}$,
(aa) $(CH_2)_n F$,
(ab) $(CH_2)_m$-imidazol-1-yl,
(ac) tetrazol-5-yl,
(ad) $-CONH-SO_2$-aryl,
(ae) $-CONH-SO_2-(C_1-C_8)$-alkyl, wherein the alkyl group is unsubstituted or substituted with a substituent selected from the group consisting of: $-OH$, $-SH$, $-O(C_1-C_4)$-alkyl, $-S-(C_1-C_4)$-alkyl, $-CF_3$, Cl, Br, F, I, $-NO_2$, $-CO_2H$, $-CO_2-(C_1-C_4)$-alkyl, $-NH_2$, $-NH[(C_1-C_4)$-alkyl], $-N[(C_1-C_4)$-alkyl]$_2$; and
(af) $-CONH-SO_2-(C_1-C_4)$-perfluoroalkyl,
(ag) $-CONHSO_2NR^{2a}R^{2a}$; and (ah) 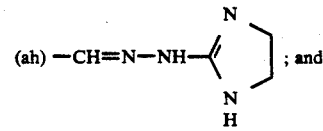 ; and $R^5$ is:
(a) CN,
(b) $NO_2$, or
(c) $CO_2R^{2a}$; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl, (e) Cl, Br, F, I,
(f) $(C_1-C_6)$-alkoxy,
(g) when $R^9$ and $R^{10}$ are on adjacent carbons, they can be joined to form an phenyl ring,
(h) $(C_1-C_6)$-perfluoroalkyl,
(i) $(C_3-C_7)$-cycloalkyl, unsubstituted or substituted with $(C_1-C_6)$-alkyl,
(j) aryl,
(k) $(C_1-C_6)$-alkyl-$S(O)_x$—$(CH_2)_n$—,
(l) hydroxy-$(C_1-C_6)$-alkyl,
(m) —$CF_3$,
(n) —$CO_2R^{2a}$,
(o) —OH,
(p) —$NR^2R^{21}$,
(q) —$[(C_1-C_6)$-alkyl$]NR^2R^{21}$,
(r) —$NO_2$,
(s) —$(CH_2)_n$—$SO_2$—$N(R^2)_2$,
(t) —$NR^2CO$—$(C_1-C_4)$-alkyl, or
(u) —$CON(R^2)_2$; and X is:
(a) —O—,
(b) —$S(O)_x$—,
(c) —$NR^{13}$—
(d) —$CH_2O$—,
(e) —$CH_2S(O)_x$,
(f) —$CH_2NR^{13}$—,
(g) —$OCH_2$—,
(h) —$NR^{13}CH_2$—,
(i) —$S(O)_xCH_2$—,
(j) —$CH_2$—,
(k) —$(CH_2)_2$—,
(l) single bond, or
(m) —CH=, wherein Y and $R^{12}$ are absent forming a —C≡C— bridge to the carbon bearing Z and $R^{11}$; and Y is:
(a) single bond,
(b) —O—,
(c) —$S(O)_x$—,
(d) —$NR^{13}$—, or
(e) —$CH_2$—; and
except that X and Y are not defined in such a way that the carbon atom to which Z is attached also simultaneously is bonded to two heteroatoms (O, N, S, SO, $SO_2$);

$R^{11}$ and $R^{12}$ are independently:
(a) H,
(b) $(C_1-C_6)$-alkyl, unsubstituted or substituted with a substituent selected from the group consisting of:
 (i) aryl,
 (ii) $(C_3-C_7)$-cycloalkyl,
 (iii) $NR^2R^{21}$,
 (iv) OH,
 (v) $CO_2R^{2a}$, or
 (vi) $CON(R^2)_2$,
(c) aryl or aryl-$(C_1-C_2)$-alkyl, unsubstituted or substituted with 1 to 3 substitutents selected from the group consisting of:
 (i) Cl, Br, I, F,
 (ii) $(C_1-C_6)$-alkyl,
 (iii) $[(C_1-C_5)$-alkenyl$]CH_2$—,
 (iv) $[(C_1-C_5)$-alkynyl$]CH_2$—,
 (v) $(C_1-C_6)$-alkyl-$S(O)_x$—$(CH_2)_x$—,
 (vi) —$CF_3$,
 (vii) —$CO_2R^{2a}$,
 (viii) —OH,
 (ix) —$NR^2R^{21}$,
 (x) —$NO_2$,
 (xi) —$NR^2COR^2$,
 (xii) —$CON(R^2)_2$,
 (xiii) —G—$[(C_1-C_6)$-alkyl$]$—$R^{23}$,
 (xiv) —$P(O)[O$—$(C_1-C_4)$-alkyl$]_2$,
 and can additionally be substituted with 1 or 2 substituents selected from the group consisting of: Br, Cl or F,
(d) $(C_3-C_7)$-cycloalkyl;

G is: a single bond, O, $S(O)_x$ or $NR^{23}$; and $R^{13}$ is:
(a) H,
(b) $(C_1-C_6)$-alkyl,
(c) aryl,
(d) aryl-$(C_1-C_6)$-alkyl—(C=O)—,
(e) $(C_1-C_6)$-alkyl—(C=O)—,
(f) $[(C_2-C_5)$-alkenyl$]CH_2$—,
(g) $[(C_2-C_5)$-alkynyl$]CH_2$—, or
(h) aryl-$CH_2$—; and Z is:
(a) —$CO_2H$,
(b) —$CO_2R^{24}$,
(c) —tetrazol-5-yl,
(d) —CO—NH(tetrazol-5-yl)
(e) —CONH—$SO_2$-aryl,
(f) —CONH—$SO_2$—$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH$[(C_1-C_4)$-alkyl$]$, —N$[(C_1-C_4)$-alkyl$]_2$; and
(g) —$CONHSO_2$—$(C_1-C_4)$-perfluoroalkyl,
(i) —$CONHSO_2NR^{2a}R^{2a}$; and
(j) —$SO_2NHCO$-aryl,
(k) —$SO_2NHCO$—$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH$[(C_1-C_4)$-alkyl$]$, —N$[(C_1-C_4)$-alkyl$]_2$; and
(l) —$SO_2NHCO$—$(C_1-C_4)$-perfluoroalkyl,
(n) —$SO_2NHCONR^{2a}R^{2a}$;
(o) —$PO(OH)_2$,
(p) —$PO(OR^2)_2$, or
(q) —$PO(OH)(OR^2)$; and $R^{14}$ is:
(a) H,
(b) $(C_1-C_8)$-alkyl,
(c) $(C_1-C_8)$-perfluoroalkyl,
(d) $(C_3-C_6)$-cycloalkyl,
(e) phenyl, or
(f) benzyl; and $R^{15}$ is:
(a) H,
(b) $(C_1-C_6)$-alkyl,
(c) $(C_3-C_6)$-cycloalkyl,
(d) $(CH_2)_p$-phenyl,
(e) $OR^{17}$,
(f) $NR^{18}R^{19}$; and $R^{16}$ is:
(a) $(C_1-C_8)$-alkyl,
(b) $(C_1-C_8)$-perfluoroalkyl,
(c) 1-adamantyl,
(d) 1-naphthyl,
(e) (1-naphthyl)ethyl, or
(f) —$(CH_2)_p$-phenyl; and $R^{17}$ is:
(a) H,
(b) ($C_1$-$C_6$)-alkyl,
(c) ($C_3$-$C_6$)-cycloalkyl,
(d) phenyl, or
(e) benzyl; and $R^{18}$ and $R^{19}$ are independently:
(a) H,
(b) ($C_1$-$C_4$)-alkyl,
(c) phenyl,
(d) benzyl, or
(e) α-methylbenzyl; and $R^{21}$ is:
(a) H, or
(b) ($C_1$-$C_4$)-alkyl, is unsubstituted or substituted with:
i) $NH_2$,
ii) $NH[(C_1$-$C_4)$-alkyl],
iii) $N[(C_1$-$C_4)$-alkyl]$_2$,
iv) $CO_2H$,
v) $CO_2(C_1$-$C_4)$-alkyl,
vi) OH,
vii) $SO_3H$, or
viii) $SO_2NH_2$; and $R^{22}$ is:
(a) H,
(b) ($C_1$-$C_4$)-alkyl,
(c) ($C_1$-$C_4$)-alkoxyl,
(d) aryl,
(e) aryl-($C_1$-$C_4$)-alkyl,
(f) $CO_2R^{2a}$,
(g) $CON(R^2)_2$,
(h) $SO_2R^{2a}$,
(i) $SO_2N(R^2)_2$,
(j) $P(O)[(C_1$-$C_4)$-alkoxyl]$_2$, or
(k) imidazol-2-yl or imidazol-4-yl, in which the imidazole can be substituted with ($C_1$-$C_4$)-alkyl; and $R^{23}$ is:
(a) OH,
(b) $NR^2R^{21}$,
(c) $CO_2R^{2a}$,
(d) $CON(R^2)_2$,
(e) $S(O)_x$—($C_1$-$C_4$)-alkyl, $R^{24}$ is:
(a) ($C_1$-$C_4$)-alkyl,
(b) $CHR^{25}$—O—$COR^{26}$,
(c) $CH_2CH_2$—$N[(C_1$-$C_2)$-alkyl]$_2$,
(d) $(CH_2CH_2O)_y$—O—$[(C_1$-$C_4)$-alkyl], wherein y is 1 or 2,
(e) aryl, or —$CH_2$-aryl, where aryl is as defined above or optionally substituted with —$CO_2$—($C_1$-$C_4$)-alkyl, (f) 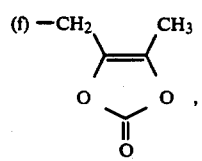

(g) 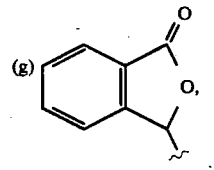

-continued (h) 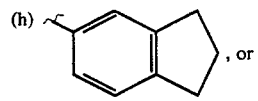, or (i) —$CH_2$ 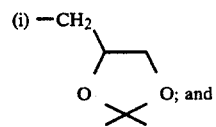; and $R^{25}$ and $R^{26}$ independently are ($C_1$-$C_6$)-alkyl or phenyl.

2. A compound which is

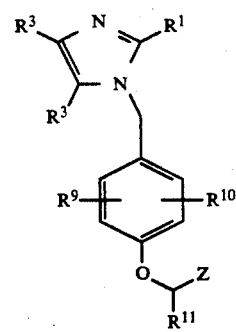

or a pharmaceutically acceptable salt thereof wherein:
$R^1$ is ($C_2$-$C_4$)-alkyl, or cyclopropyl; and
$R^3$ is H, Cl, ($C_1$-$C_4$)-perfluoroalkyl, ($C_1$-$C_4$)-alkyl, aryl, $CH_2$-aryl; and
$R^4$ is $CO_2H$, $CH_2OH$, or $CO_2(C_1$-$C_4)$-alkyl; and
$R^9$ and $R^{10}$ are independently: ($C_1$-$C_6$)-alkyl, ($C_1$-$C_6$)-alkenyl, ($C_1$-$C_6$)-alkynyl, ($C_1$-$C_4$)-alkoxyl, Cl, Br, I, F, ($C_3$-$C_8$)-cycloalkyl, or aryl, wherein aryl is defined as phenyl or naphthyl, unsubstituted or substituted with 1 or 2 substituents selected from the group consisting of: Cl, Br, F, I, ($C_1$-$C_4$)-alkyl, ($C_1$-$C_4$)-alkoxy, $NO_2$, $CF_3$, $SO_2NR^{2a}R^{2a}$, ($C_1$-$C_4$)-alkylthio, hydroxy, amino, ($C_3$-$C_7$)-cycloalkyl, ($C_3$-$C_{10}$)-alkenyl; and
$R^{11}$ is phenyl, unsubstituted or substituted with Br, Cl, F, I, ($C_1$-$C_4$)-alkyl or ($C_1$-$C_4$)-alkoxyl, ($C_1$-$C_6$)-alkyl—$S(O)_n$—$(CH_2)_n$—, hydroxy-($C_1$-$C_6$)-alkyl, —$CF_3$, —$CO_2R^{2a}$, —OH, —$NR^2R^{21}$, —$[(C_1$-$C_6)$-alkyl]$NR^2R^{21}$, —$NO_2$, —$(CH_2)_n$—$SO_2$—$N(R^2)_2$, —$NR^2CO$—($C_1$-$C_4$)-alkyl, or $CON(R^2)2$; and Z is tetrazol-5-yl, carboxyl or $CO_2(C_1$-$C_4)$-alkyl; and
$R^{21}$ is: H, or ($C_1$-$C_4$)-alkyl, wherein the alkyl is unsubstituted or substituted with a substituent selected from the group consisting of: $NH_2$, $NH[(C_1$-$C_4)$-alkyl], $N[(C_1$-$C_4)$-alkyl]$_2$, $CO_2H$, OH, $SO_3H$, $CO_2(C_1$-$C_4)$-alkyl or $SO_2NH_2$.

3. A compound which is

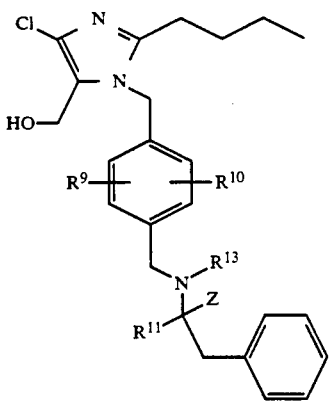

or a pharmaceutically acceptable salt thereof wherein:

Z is $CO_2H$, $CO_2$—$(C_1-C_4)$-alkyl or 1H-tetrazol-5-yl; and $R^9$ and $R^{10}$ are independently: $(C_1-C_6)$-alkyl, $(C_1-C_6)$-alkenyl or $(C_1-C_6)$-alkynyl, $(C_1-C_4)$-alkoxyl, Cl, Br, I, F, $(C_3-C_8)$-cycloalkyl, or aryl, wherein aryl is defined as phenyl or naphthyl, unsubstituted or substituted with 1 or 2 substituents selected from the group consisting of: Cl, Br, F, I, $(C_1-C_4)$-alkyl, $(C_1-C_4)$-alkoxy, $NO_2$, $CF_3$, $SO_2NR^{2a}R^{2a}$, $(C_1-C_4)$-alkylthio, hydroxy, amino, $(C_3-C_7)$-cycloalkyl, $(C_3-C_{10})$-alkenyl; and $R^{11}$ is H, or benzyl; and $R^{13}$ is H, $CH_3(CH_2)_3C(=O)$—, $C_6H_5CH_2CH_2C(=O)$—, or $C_6H_5CH_2C(=O)$—.

4. A compound which is

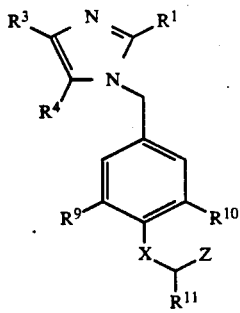

or a pharmaceutically acceptable salt thereof wherein:

$R^1$ is: $(C_1-C_4)$-alkyl and cyclopropyl; and $R^{2a}$ is: H, $(C_1-C_6)$-alkyl, benzyl, or phenyl; and $R^3$ is H, Cl, $(C_1-C_4)$-perfluoroalkyl, $(C_1-C_4)$-alkylamino, $(C_1-C_4)$-acylamino; and $R^4$ is $CO_2H$, $CH_2OH$, or $CO_2(C_1-C_4)$-alkyl; and $R^9$ and $R^{10}$ are independently: $(C_1-C_6)$-alkyl, $(C_1-C_6)$-alkenyl or $(C_1-C_6)$-alkynyl, $(C_1-C_4)$-alkoxyl, Cl, Br, I, F, $(C_3-C_8)$-cycloalkyl, or aryl; and $R^{11}$ is: aryl or aryl—$CH_2$—, wherein the aryl is unsubstituted or substituted with 1 or 2 substituents selected from the group consisting of: Br, Cl, F, I, $(C_1-C_4)$-alkyl, $(C_1-C_4)$-alkoxyl, $NO_2$, $CF_3$, $(C_1-C_4)$-alkylthio, OH, —$NR^{2a}R^{2a}$ and X is: O, $NR^{13}$, $CH_2$, or —CH=, which is double bonded to the carbon bearing Z and $R^{11}$; and $R^{13}$ is: H, $(C_1-C_6)$-alkyl, $(C_1-C_6)$-alkenyl, aryl; and Z is: $CO_2H$, $CO_2$—$(C_1-C_4)$-alkyl, 1H-tetrazol-5-yl, —$CONHSO_2$-aryl, wherein aryl is defined as phenyl or naphthyl, unsubstituted, mono- or disubstituted with substituents selected from the group consisting of: H, $(C_1-C_4)$-alkyl, $(C_1-C_4)$-alkoxy, $NO_2$, $CF_3$, $SO_2NR^{2a}R^{2a}$, $(C_1-C_4)$-alkylthio, hydroxy, amino, $(C_3-C_7)$-cycloalkyl, $(C_3-C_{10})$-alkenyl.

5. A compound which is

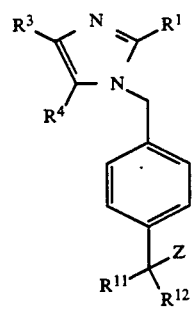

or a pharmaceutically acceptable salt thereof wherein:

$R^1$ is: $(C_1-C_4)$-alkyl and cyclopropyl; and $R^{2a}$ is: H, $(C_1-C_6)$-alkyl, benzyl, or phenyl; and $R^3$ is H, Cl, $(C_1-C_4)$-perfluoroalkyl, $(C_1-C_4)$-alkylamino, $(C_1-C_4)$-acylamino; and $R^4$ is $CO_2H$, $CH_2OH$, or $CO_2(C_1-C_4)$-alkyl; and $R^9$ and $R^{10}$ are independently: $(C_1-C_6)$-alkyl, $(C_1-C_6)$-alkenyl or $(C_1-C_6)$-alkynyl, $(C_1-C_4)$-alkoxyl, Cl, Br, I, F, $(C_3-C_8)$-cycloalkyl, or aryl; and $R^{11}$ is: aryl or aryl—$CH_2$—, wherein the aryl is unsubstituted or substituted with 1 or 2 substituents selected from the group consisting of: Br, Cl, F, I, $(C_1-C_4)$-alkyl, $(C_1-C_4)$-alkoxyl, $NO_2$, $CF_3$, $(C_1-C_4)$-alkylthio, OH, —$NR^{2a}R^{2a}$; and $R^{12}$ is H, OH, or $(C_1-C_4)$-alkyl; and Z is $CO_2H$, $CO_2$—$(C_1-C_4)$-alkyl or 1H-tetrazol-5-yl.

6. A compound or its pharmaceutically acceptable salt selected from the group consisting of:

2-Butyl-1-[4-(N-(1(R)-carbomethoxy-1-benzyl)methyl)aminomethylphenyl]methyl-4-chloro-5-hydroxymethylimidazole;

2-Butyl-1-[4-(N-(1(R)-carboxy-1-benzyl)methyl)aminomethylphenyl]methyl-4-chloro-5-hydroxymethylimidazole;

2-Butyl-1-[4-(N-(1(R)-carbomethoxy-1-benzyl)methyl-methyl-N-pentanoyl)aminomethylphenyl]-4-chloro-5-hydroxymethylimidazole;

2-Butyl-1-[4-(N-(1(R)-carboxy-1-benzyl)methyl-N-pentanoyl)aminomethyl-phenyl]methyl-4-chloro-5-hydroxymethylimidazole;

2-Butyl-1-[4-(N-(1-(R)-carboxy-1-benzyl)methyl-N-(3-phenyl)propionyl)aminomethylphenyl]methyl-4-chloroimidazole;

2-Butyl-1-[4-N-(1(R)-carbomethoxy-1-benzyl)methyl-N-(phenylacetyl)aminomethylphenyl]methyl-4-chloro-5-hydroxymethylimidazole;

2-Butyl-1-[4-(N-(1(R)-carboxy-1-benzyl-methyl-N-(phenylacetyl)aminomethylphenyl]methyl-4-chloro-5-hydroxymethylimidazole;

2-Butyl-1-[4-(N-(1(S)-carbomethoxy-1-benzyl)aminomethylphenyl]methyl-4-chloro-5-hydroxymethylimidazole;

2-Butyl-1-[4-(N-(1(S)-carboxy-1-benzyl)aminomethylphenyl]methyl-4-chloro-5-hydroxy-methylimidazole;

2-Butyl-1-[4-(N-(1(S)-carbomethoxy-1-benzyl)-N-pentanoyl)aminomethylphenyl]methyl-4-chloro-5-hydroxymethylimidazole;

2-Butyl-1-[4-(N-(1(S)-carboxy-1-benzyl)methyl-N-pentanoyl)aminomethylphenyl]methyl-4-chloro-5-hydroxymethylimidazole;

2-Butyl-5-t-butyldimethylsilyloxymethyl-1-[4-(1-carbomethoxy-1,1-dibenzyl)methyl)aminomethylphenyl]methyl-4-chlorimidazole;

2-Butyl-1-[4-(N-(1-carbomethoxy-1,1-dibenzyl)methyl)aminomethylphenyl]methyl-4-chloro-5-hydroxymethylimidazole;

2-Butyl-1-[4-(N-(1-carboxy-1,1-dibenzyl)methyl)aminomethylphenyl]phenyl]methyl-4-chloro-5-hydroxymethylimidazole;

1-[4-(1-(N-benzyl-N-pentanoyl)amino-1-(tetrazol-5-ylmethylphenyl]methyl-2-butyl-5-t-butyldimethylsilyloxymethyl-4-chloroimidazole;

2-Butyl-4-chloro-5-hydroxymethyl-3-[4-(1-(1'-hydroxy-1-phenyl-1-tetrazol-5-yl)methylphenyl]methylimidazole;

2-Butyl-1-[4-(1-carboxy-1-(2-chloro)phenyl)methoxyphenyl]methyl-4-chloro-5-hydroxymethylimidazole;

2-Butyl-1-[4-(1-carboxy-1-phenyl)methoxy-3,5-dipropylphenyl]methyl-4-chloro-5-hydroxymethylimidazole;

2-Butyl-4-chloro-5-hydroxymethyl-1-[4-(1-phenyl-1-tetrazol-5-yl))methylphenyl]methylimidazole; and 2-Butyl-1-[4-(N-(1-carboxy-1-(2-phenyl)ethyl)aminophenyl]methyl-4-chloro-5-hydroxymethylimidazole.

7. A pharmaceutical composition useful in the treatment of hypertension which comprises a pharmaceutically acceptable carrier and a therapeutically effective amount of a compound of claim 1.

8. A method of treating hypertension which comprises administering to a patient in need of such treatment a therapeutically effective amount of a compound of claim 1.

* * * * *